US011590089B2

(12) United States Patent
Sunahara et al.

(10) Patent No.: US 11,590,089 B2
(45) Date of Patent: Feb. 28, 2023

(54) BETA-2 SELECTIVE ADRENERGIC RECEPTOR AGONISTS

(71) Applicants: The Board of Trustees of the Leland Stanford Junior University, Stanford, CA (US); The Regents of the University of California, Oakland, CA (US); FRIEDRICH-ALEXANDER-UNIVERSITÄT ERLANGEN-NÜRNBERG, Erlangen (DE)

(72) Inventors: Roger Sunahara, San Diego, CA (US); Harald Huebner, Heroldsbach (DE); Jeremy Shonberg, Symonston (AU); Anne Stößel, Fürth (DE); Markus Stanek, Uttenreuth (DE); Dorothée Möller, Erlangen (DE); Mary Joyce Clark, La Jolla, CA (US); Brian K. Kobilka, Stanford, CA (US); Peter Gmeiner, Erlangen (DE); Luis Maul, Erlangen (DE)

(73) Assignees: THE BOARD OF TRUSTEES OF THE LELAND STANFORD JUNIOR UNIVERSITY, Stanford, CA (US); THE REGENTS OF THE UNIVERSITY OF CALIFORNIA, Oakland, CA (US); FRIEDRICH-ALEXANDER-UNIVERSITÄT ERLANGEN-NÜRNBERG, Erlangen (DE)

( * ) Notice: Subject to any disclaimer, the term of this patent is extended or adjusted under 35 U.S.C. 154(b) by 124 days.

(21) Appl. No.: 16/768,025

(22) PCT Filed: Nov. 30, 2018

(86) PCT No.: PCT/US2018/063480
§ 371 (c)(1),
(2) Date: May 28, 2020

(87) PCT Pub. No.: WO2019/112913
PCT Pub. Date: Jun. 13, 2019

(65) Prior Publication Data
US 2020/0360304 A1  Nov. 19, 2020

Related U.S. Application Data

(60) Provisional application No. 62/594,476, filed on Dec. 4, 2017.

(51) Int. Cl.
*A61K 31/13* (2006.01)
*A61K 31/16* (2006.01)
*A61K 31/337* (2006.01)

(52) U.S. Cl.
CPC .............. *A61K 31/13* (2013.01); *A61K 31/16* (2013.01); *A61K 31/337* (2013.01)

(58) Field of Classification Search
CPC ...... A61K 31/13; A61K 31/337; A61K 31/16; A61K 31/695
See application file for complete search history.

(56) References Cited

U.S. PATENT DOCUMENTS

| | | | |
|---|---|---|---|
| 4,010,202 A | 3/1977 | Sugihara et al. | |
| 4,035,512 A | 7/1977 | Sugihara et al. | |
| 4,041,079 A * | 8/1977 | Sugihara | C07D 311/22 564/414 |
| 4,104,402 A | 8/1978 | Sugihara et al. | |
| 5,859,044 A | 1/1999 | Dow et al. | |
| 6,518,480 B1 | 2/2003 | Conklin | |
| 2004/0192625 A1 | 9/2004 | Liggett | |
| 2004/0235749 A1 | 11/2004 | Chemtob et al. | |

FOREIGN PATENT DOCUMENTS

| WO | WO 00/18389 A2 | 4/2000 |
|---|---|---|
| WO | WO2019036678 A1 | 2/2019 |

OTHER PUBLICATIONS

Barisione et al. (Pharmaceuticals, 2010, 3, 1016-1044). (Year: 2010).*
Sugihara et al., "Stereoselective Syntheses of cis- and trans-2-Alkylamino-1,2,3,4-tetrahydro-1-naphthalenols by Acid-catalyzed Ring Opening of 1,2-N-Alkylimino-1,2,3,4-tetrahydronaphthalenes", Chemical and Pharmaceutical Bulletin, 1978, 26(2): 411-122.
Calderon et al., "Synthesis and adrenergic activity of a semi-rigid analog of 6-fluoronorepinephrine", Medicinal Chemistry Research, 1992, 2: 419-433.
Hambley et al., "Structure of methyl(1,5,6-trihydroxy-1,2,3,4-tetrahydro-2-naphthyl)ammonium bromide" Acta Cryst., 1986, 42: 1442-1444.
Itoh et al., "The syntheses and β-adrenoceptor activities of N-substituted 2-amino-5,6-dihydroxy-1,2,3,4-tetrahydro-1-naphthalenols", Chemical & Pharmaceutical Bulletin, 1977, 25(11): 2917-2928.

(Continued)

*Primary Examiner* — Umamaheswari Ramachandran
(74) *Attorney, Agent, or Firm* — James S. Keddie; Bozicevic, Field & Francis LLP

(57) ABSTRACT

Aspects of the present disclosure include conformationally restricted analogs of catecholamine type compounds (e.g., isoprenaline, adrenaline, noradrenaline) which activate β2AR with high selectivity over β1AR. The subject beta-2 selective adrenergic receptor agonist compounds may serve as bronchiodilators and find use in the treatment of a variety of bronchoconstrictive diseases and conditions. Also provided are compositions and methods for treating preterm labor. A method of treating acute asthma including administration of a subject compound to a subject in need thereof is provided. The subject method can provide for reduced undesirable side effects associated with non-selective β-adrenergic receptor agonism, such as inotropic and chronotropic effects that leads to elevated blood pressure. The compounds can also be used to prevent or treat heart failure. Kits and compositions for practicing the subject methods are also provided.

4 Claims, 1 Drawing Sheet

(56) References Cited

OTHER PUBLICATIONS

Iwasa et al., "Enzyme Immunoassay of a β-Adrenergic Agent Using β-Galactosidase as Label", Immunophamnacology, 1978,1: 3-12.
Linschoten et al., "A computer modeling study of hydrogen bonds in ligand-β-adrenoceptor complexes: its implications in the deduction of a receptor map", Journal of Molecular Structure, 1990,237: 339-354.
Motohashi et al., "Crystal Structure of (±)-trans-2-cyclobutylamino-5,6-dihydrxy-1,2,3,4-tetrahydro-1-naphthalenol nydrobromide" Chemical & Pharmaceutical Bulletin, 1980, 28(12): 3656-3661.
Motohashi et al., "Nuclear magnetic resonance studies of 2-amino- and 2-substituted amino-5,6-dihydroxy-1,2,3,4-tetrahydro-1-naphthalenols". Chemical & Pharmaceutical Bulletin, 1981, 29(6): 1501-1509.
Nishikwawa et al., "Selective β-adrenoceptor activities of tetrahydronaphthalene derivatives", Life Sciences, 1975, 16: 305-314.
Oka et al., "Syntheses of conformationally Rigid Catecholamine Derivatives", Chem. Pharm. Bull., 1977: 25(4): 632-639.

* cited by examiner

＃ BETA-2 SELECTIVE ADRENERGIC RECEPTOR AGONISTS

CROSS-REFERENCE

This application is a § 371 national phase of International Application No. PCT/US2018/063480, filed on Nov. 30, 2018, which claims the benefit of U.S. Provisional Patent Application No. 62/594,476, filed Dec. 4, 2017, which applications are incorporated herein by reference in their entireties.

STATEMENT REGARDING FEDERALLY SPONSORED RESEARCH OR DEVELOPMENT

This invention was made with Government support under contract GM106990 awarded by the National Institutes of Health. The Government has certain rights in the invention.

INTRODUCTION

G Protein-Coupled Receptors (GPCRs) are a large superfamily of receptors that span intra- and extracellular spaces with seven transmembrane helices. GPCRs serve as important drug targets with approximately 30% of drugs on the market acting via GPCRs. The adrenergic family of receptors are primary points of action of the endogenous hormones and/or neurotransmitters adrenaline and noradrenaline. They are divided into two subfamilies (α and β) which differ in ligand specificity, expression in tissues, and downstream signalling.

Stimulation of the β-adrenergic receptors (RAR), including subtypes β1, β2 and β3AR, by adrenaline and noradrenaline leads to the activation of Gs proteins, resulting in activation of adenylyl cyclase and subsequent accumulation of cAMP. Besides the activation of G proteins, recruitment of β-arrestins is known to significantly contribute to the physiological functions mediated by adrenoceptors.

For the β2AR in particular, activation induces relaxation of airway smooth muscle, and accordingly β2AR-targeting ligands have applications in the treatment of various respiratory diseases including asthma and chronic obstructive pulmonary disorder (COPD). In contrast, β1AR is highly expressed in the heart and its activation causes positive inotropic and chronotropic effects. As these lead to elevated blood pressure, co-activation of β1AR by unselective βAR agonists is a severe and unwanted side effect antiasthmatic or COPD therapy.

Bronchoconstrictive disorders affect millions worldwide. Such disorders include asthma (including bronchial asthma, allergic asthma and intrinsic asthma, e.g., late asthma and airway hyper-responsiveness), chronic bronchitis and other chronic obstructive pulmonary diseases. Compounds having β2-AR agonist activity are of interest to treat these conditions.

SUMMARY

Aspects of the present disclosure include conformationally restricted analogs of catecholamine type compounds (e.g., isoprenaline, adrenaline, noradrenaline) which activate β2AR with high selectivity over β1AR. The subject beta-2 selective adrenergic receptor agonist compounds may serve as bronchiodilators and find use in the treatment of a variety of bronchoconstrictive diseases and conditions. Also provided are compositions and methods for treating preterm labor. A method of treating acute asthma including administration of a subject compound to a subject in need thereof is provided. The subject method can provide for reduced undesirable side effects associated with non-selective β-adrenergic receptor agonism, such as inotropic and chronotropic effects that leads to elevated blood pressure. The compounds can also be used to prevent or treat heart failure. Kits and compositions for practicing the subject methods are also provided.

BRIEF DESCRIPTION OF THE DRAWINGS

The invention is best understood from the following detailed description when read in conjunction with the accompanying figures. It is emphasized that, according to common practice, the various features of the figures are not to-scale. On the contrary, the dimensions of the various features are arbitrarily expanded or reduced for clarity. Included in the drawings are the following figures. It is understood that the FIGURES, described below, are for illustration purposes only. The figures are not intended to limit the scope of the present teachings in any way.

DEFINITIONS

Figures 1A, 1B:
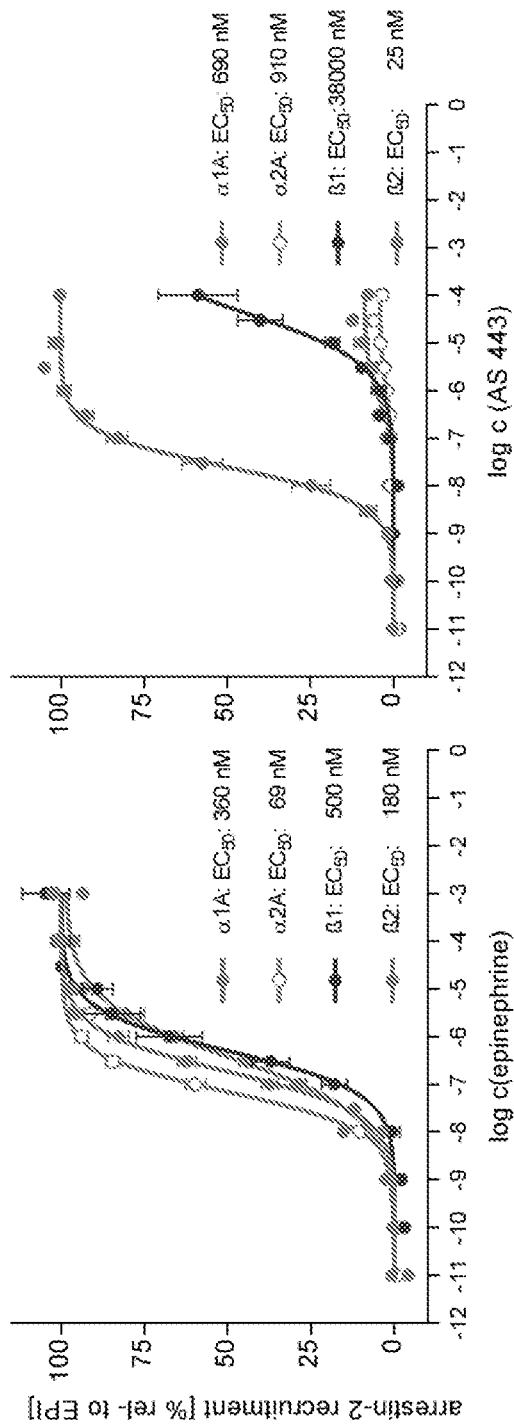
FIG. 1A-1B shows representative dose-response curves of epinephrine (FIG. 1A) and exemplary compound AS 443 (FIG. 1B) determined by an arrestin recruitment assay expressing the subtype selectivity of exemplary compounds.

Before describing exemplary embodiments in greater detail, the following definitions are set forth to illustrate and define the meaning and scope of the terms used in the description. Any undefined terms have their art recognized meanings.

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978)

Where compounds described herein contain one or more chiral centers and/or double-bond isomers (i.e., geometric isomers), enantiomers or diastereomers, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein, unless stated otherwise. Enantiomeric and stereoisomeric mixtures can be resolved into their component enantiomers or stereoisomers using separation techniques or chiral synthesis techniques. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^2$H, $^3$H, $^{11}$C, $^{13}$C, $^{14}$C, $^{15}$N, $^{18}$O, $^{17}$O, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Enantiomer" refers to one of a pair of chiral molecules that are mirror images of each other. Enantiomers can be referred to as (+) or (−) enantiomers. Enantiomers can be referred to as (S)- or (R)-enantiomers.

The term "racemic" or "racemate", and other like terms refer to generally equimolar proportions of a (+)-enantiomer and a (−)-enantiomer of a compound in a composition.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

Also of interest as active agents for use in embodiments of the methods are prodrugs. Such prodrugs are in general functional derivatives of the compounds that are readily convertible in vivo into the required compounds. Thus, in the methods of the present disclosure, the term "administering" encompasses administering the compound specifically disclosed or with a compound which may not be specifically disclosed, but which converts to the specified compound in vivo after administration to the subject in need thereof. Conventional procedures for the selection and preparation of suitable prodrug derivatives are described, e.g., in Wermuth, "Designing Prodrugs and Bioprecursors" in Wermuth, ed. The Practice of Medicinal Chemistry, 2d Ed., pp. 561-586 (Academic Press 2003). Prodrugs include esters that hydrolyze in vivo (e.g., in the human body) to produce a compound described herein suitable for the methods and compositions of the present disclosure. Suitable ester groups include, without limitation, those derived from pharmaceutically acceptable, aliphatic carboxylic acids, particularly alkanoic, alkenoic, cycloalkanoic and alkanedioic acids, in which each alkyl or alkenyl moiety has no more than 6 carbon atoms. Illustrative esters include formates, acetates, propionates, butyrates, acrylates, citrates, succinates, and ethylsuccinates.

A "therapeutically effective amount" or "efficacious amount" means the amount of a compound that, when administered to a mammal or other subject for treating a disease, condition, or disorder, is sufficient to effect such treatment for the disease, condition, or disorder. The "therapeutically effective amount" will vary depending on the compound, the disease and its severity and the age, weight, etc., of the subject to be treated.

The term "unit dosage form," as used herein, refers to physically discrete units suitable as unitary dosages for human and animal subjects, each unit containing a predetermined quantity of a compound (e.g., an aminopyrimidine compound, as described herein) calculated in an amount sufficient to produce the desired effect in association with a pharmaceutically acceptable diluent, carrier or vehicle. The specifications for unit dosage forms depend on the particular compound employed and the effect to be achieved, and the pharmacodynamics associated with each compound in the host.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal, intramuscular, subcutaneous, inhalation, and the like.

The term "sample" as used herein relates to a material or mixture of materials, typically, although not necessarily, in fluid, i.e., aqueous, form, containing one or more components of interest. Samples may be derived from a variety of sources such as from food stuffs, environmental materials, a biological sample or solid, such as tissue or fluid isolated from an individual, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components). In certain embodiments of the method, the sample includes a cell. In some instances of the method, the cell is in vitro. In some instances of the method, the cell is in vivo.

As used herein, the phrase "having the formula" or "having the structure" is not intended to be limiting and is used in the same way that the term "comprising" is commonly used. The term "independently selected from" is used herein to indicate that the recited elements, e.g., R groups or the like, can be identical or different.

As used herein, the terms "may," "optional," "optionally," or "may optionally" mean that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The term "alkyl" as used herein refers to a branched or unbranched saturated hydrocarbon group (i.e., a monoradical) typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although not necessarily, alkyl groups herein may contain 1 to about 18 carbon atoms, and such groups may contain 1 to about 12 carbon atoms. The term "lower alkyl" intends an alkyl group of 1 to 6 carbon atoms. "Substituted alkyl" refers to alkyl substituted with one or more substituent groups, and this includes instances wherein two hydrogen atoms from the same carbon atom in an alkyl substituent are replaced, such as in a carbonyl group (i.e., a substituted alkyl group may include a —C(=O)— moiety). The terms "heteroatom-containing alkyl" and "heteroalkyl" refer to an alkyl substituent in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "substituted alkyl" is meant to include an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein may contain 2 to about 18 carbon atoms, and for example may contain 2 to 12 carbon atoms. The term "lower alkenyl" intends an alkenyl group of 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein may contain 2 to about 18 carbon atoms, and such groups may further contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "C1-C6 alkoxy" or "lower alkoxy" herein may, for example, may contain 1 to 3 carbon atoms, and as a further example, such substituents may contain 1 or 2 carbon atoms (i.e., methoxy and ethoxy).

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "aryl" as used herein, and unless otherwise specified, refers to an aromatic substituent generally, although not necessarily, containing 5 to 30 carbon atoms and containing a single aromatic ring or multiple aromatic rings that are fused together, directly linked, or indirectly linked (such that the different aromatic rings are bound to a common group such as a methylene or ethylene moiety). Aryl groups may, for example, contain 5 to 20 carbon atoms, and as a further example, aryl groups may contain 5 to 12 carbon atoms. For example, aryl groups may contain one aromatic ring or two or more fused or linked aromatic rings (i.e., biaryl, aryl-substituted aryl, etc.). Examples include phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. Aryl is intended to include stable cyclic, heterocyclic, polycyclic, and polyheterocyclic unsaturated C$_3$-C$_{14}$ moieties, exemplified but not limited to phenyl, biphenyl, naphthyl, pyridyl, furyl, thiophenyl, imidazoyl, pyrimidinyl, and oxazoyl; which may further be substituted with one to five members selected from the group consisting of hydroxy, $C_1$-$C_8$ alkoxy, $C_1$-$C_8$ branched or straight-chain alkyl, acyloxy, carbamoyl, amino, N-acylamino, nitro, halogen, trifluoromethyl, cyano, and carboxyl (see e.g. Katritzky, Handbook of Heterocyclic Chemistry). If not otherwise indicated, the term "aryl" includes unsubstituted, substituted, and/or heteroatom-containing aromatic substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 30 carbon atoms. Aralkyl and alkaryl groups may, for example, contain 6 to 20 carbon atoms, and as a further example, such groups may contain 6 to 12 carbon atoms.

The term "alkylene" as used herein refers to a di-radical alkyl group. Unless otherwise indicated, such groups include saturated hydrocarbon chains containing from 1 to 24 carbon atoms, which may be substituted or unsubstituted, may contain one or more alicyclic groups, and may be heteroatom-containing. "Lower alkylene" refers to alkylene linkages containing from 1 to 6 carbon atoms. Examples include, methylene (—$CH_2$—), ethylene (—$CH_2CH_2$—), propylene (—$CH_2CH_2CH_2$—), 2-methylpropylene (—$CH_2$—$CH(CH_3)$—$CH_2$—), hexylene (—$(CH_2)_6$—) and the like.

Similarly, the terms "alkenylene," "alkynylene," "arylene," "aralkylene," and "alkarylene" as used herein refer to di-radical alkenyl, alkynyl, aryl, aralkyl, and alkaryl groups, respectively.

The term "amino" is used herein to refer to the group —NRR' wherein R and R' are independently hydrogen or nonhydrogen substituents, with nonhydrogen substituents including, for example, alkyl, aryl, alkenyl, aralkyl, and substituted and/or heteroatom-containing variants thereof.

The terms "halo" and "halogen" are used in the conventional sense to refer to a chloro, bromo, fluoro or iodo substituent.

"Carboxyl," "carboxy" or "carboxylate" refers to —$CO_2H$ or salts thereof.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the terms "heterocyclic" or "heterocycle" refer to a cyclic substituent that is heteroatom-containing, the terms "heteroaryl" and "heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, furyl, pyrimidinyl, imidazolyl, 1,2,4-triazolyl, tetrazolyl, etc., and examples of heteroatom-containing alicyclic groups are pyrrolidino, morpholino, piperazino, piperidino, tetrahydrofuranyl, etc. "Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl, and trihalomethyl.

As used herein, the terms "Heterocycle," "heterocyclic," "heterocycloalkyl," and "heterocyclyl" refer to a saturated or unsaturated group having a single ring or multiple condensed rings, including fused bridged and spiro ring systems, and having from 3 to 15 ring atoms, including 1 to 4 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —$SO_2$— moieties.

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO— heteroaryl, —SO$_2$-alkyl, —SO$_2$-substituted alkyl, —SO$_2$-aryl, —SO$_2$-heteroaryl, and fused heterocycle.

"Hydrocarbyl" refers to univalent hydrocarbyl radicals containing 1 to about 30 carbon atoms, including 1 to about 24 carbon atoms, further including 1 to about 18 carbon atoms, and further including about 1 to 12 carbon atoms, including linear, branched, cyclic, saturated and unsaturated species, such as alkyl groups, alkenyl groups, aryl groups, and the like. A hydrocarbyl may be substituted with one or more substituent groups. The term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation, functional groups, and the hydrocarbyl moieties C1-C24 alkyl (including C1-C18 alkyl, further including C1-C12 alkyl, and further including C1-C6 alkyl), C2-C24 alkenyl (including C2-C18 alkenyl, further including C2-C12 alkenyl, and further including C2-C6 alkenyl), C2-C24 alkynyl (including C2-C18 alkynyl, further including C2-C12 alkynyl, and further including C2-C6 alkynyl), C5-C30 aryl (including C5-C20 aryl, and further including C5-C12 aryl), and C6-C30 aralkyl (including C6-C20 aralkyl, and further including C6-C12 aralkyl). The above-mentioned hydrocarbyl moieties may be further substituted with one or more functional groups or additional hydrocarbyl moieties such as those specifically enumerated. Unless otherwise indicated, any of the groups described herein are to be interpreted as including substituted and/or heteroatom-containing moieties, in addition to unsubstituted groups.

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

When the term "substituted" appears prior to a list of possible substituted groups, it is intended that the term apply to every member of that group. For example, the phrase "substituted alkyl and aryl" is to be interpreted as "substituted alkyl and substituted aryl." In addition to the disclosure herein, the term "substituted," when used to modify a specified group or radical, can also mean that one or more hydrogen atoms of the specified group or radical are each, independently of one another, replaced with the same or different substituent groups as defined below. In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —O(O)R$^{70}$, —C(S)R$^{70}$, —C(NR$^{70}$)R$^{70}$, —O(O)O$^-$M$^+$, —O(O)OR$^{70}$, —C(S)OR$^{70}$, —O(O)NR$^{80}$R$^{80}$, —C(NR$^{70}$)NR$^{80}$R$^{80}$, —OC(O)R$^{70}$, —OC(S)R$^{70}$, —OC(O) O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S) OR$^{70}$, —NR$^{70}$C(O)NR$^{80}$R$^{80}$, —NR$^{70}$C(NR$^{70}$R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C1-O$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3$$^-$M$^+$, —SO$_3$R$^{70}$, —OSO$_2$R$^{70}$, —OSO$_3$$^-$M$^+$, —OSO$_3$R$^{70}$, —PO$_3$$^{-2}$ (M$^+$)$_2$, —P(O)(OR$^{70}$)O$^-$M$^+$, —P(O)(OR$^{70}$)$_2$, —O(O)R$^{70}$, —C(S)R$^{70}$, —C(NR$^{70}$)R$^{70}$, —CO$_2$$^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2$$^-$M$^+$, —OCO$_2$R$^{70}$, —OC(S)OR$^{70}$, —NR$^{70}$C(O)R$^{70}$, —NR$^{70}$C(S)

$R^{70}$, $-NR^{70}CO_2^-M^+$, $-NR^{70}CO_2R^{70}$, $-NR^{70}C(S)OR^{70}$, $-NR^{70}C(O)NR^{80}R^{80}$, $-NR^{70}C(NR^{70}R^{70}$ and $-NR^{70}C(NR^{70})NR^{80}R^{80}$, where $R^{60}$, $R^{70}$, $R^{80}$ and $M^+$ are as previously defined, provided that in case of substituted alkene or alkyne, the substituents are not $-O^-M^+$, $-OR^{70}$, $-SR^{70}$, or $-S^-M^+$.

In addition to the groups disclosed with respect to the individual terms herein, substituent groups for hydrogens on nitrogen atoms in "substituted" heteroalkyl and cycloheteroalkyl groups are, unless otherwise specified, $-R^{60}$, $-O^-M^+$, $-OR^{70}$, $-SR^{70}$, $-S^-M^+$, $-NR^{80}R^{80}$, trihalomethyl, $-CF_3$, $-CN$, $-NO$, $-NO_2$, $-S(O)_2R^{70}$, $-S(O)_2O^-M^+$, $-S(O)_2OR^{70}$, $-OS(O)_2R^{70}$, $-OS(O)_2O^-M^+$, $-OS(O)_2OR^{70}$, $-P(O)(O^-)_2(M^+)_2$, $-P(O)(OR^{70})O^-M^+$, $-P(O)(OR^{70})(OR^{70})$, $-O(O)R^{70}$, $-C(S) R^{70}$, $-C(NR^{70})R^{70}$, $-O(O)OR^{70}$, $-C(S)OR^{70}$, $-C(O)NR^{80}R^{80}$, $-C(NR^{70})NR^{80}R^{80}$, $-OC(O)R^{70}$, $-OC(S)R^{70}$, $-OC(O)OR^{70}$, $-OC(S)OR^{70}$, $-NR^{70}C(O)R^{70}$, $-NR^{70}C(S)R^{70}$, $-NR^{70}C(O)OR^{70}$, $-NR^{70}C(S) OR^{70}$, $-NR^{70}C(O)NR^{80}R^{80}$, $-NR^{70}C(NR^{70})R^{70}$ and $-NR^{70}C(NR^{70})NR^{80}R^{80}$, where $R^{60}$, $R^{70}$, $R^{80}$ and $M^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "linker" or "linkage" refers to a linking moiety that connects two groups and has a backbone of 100 atoms or less in length. A linker or linkage may be a covalent bond that connects two groups or a chain of between 1 and 100 atoms in length, for example of 1, 2, 3, 4, 5, 6, 8, 10, 12, 14, 16, 18 or 20 carbon atoms in length, where the linker may be linear, branched, cyclic or a single atom. In certain cases, one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. The linker may include one or more substituent groups, for example with an alkyl, aryl or alkenyl group. A linker may include, without limitations, one or more of poly(ethylene glycol); ethers, thioethers, tertiary amines, —NH—, —NHCO—, —NHSO$_2$—, and alkyls, which may be straight or branched, e.g., methyl, ethyl, n-propyl, 1-methylethyl (isopropyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable.

Other definitions of terms may appear throughout the specification.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

DETAILED DESCRIPTION

As summarized above, aspects of the present disclosure include agonist compounds, compositions and methods for the selective activation of β2 adrenergic receptors of interest. Aspects of the methods include contacting a sample with a beta-2 selective adrenergic receptor agonist compound to activate a β2 adrenergic receptor. Also provided are compositions and methods for treating a bronchoconstrictive disease or condition. Also provided are compositions and methods for treating preterm labor. Aspects of the methods of treating include administering to a subject an effective amount of beta-2 selective adrenergic receptor agonist compound to treat the subject for the disease or condition of interest. In some cases, administration may be achieved via nebulization and/or inhalation of the subject composition. In some embodiments, the compounds may be used to prevent or treat heart failure.

These compounds, compositions and methods find use in a variety of applications in which selective activation of a β2 adrenergic receptor is desired.

Beta-2 Selective Adrenergic Receptor Agonist Compounds

Aspects of the present disclosure include beta-2 selective adrenergic receptor agonist compounds (β2AR selective compound) and compositions including the same which find use in selectively agonizing beta-2 adrenergic receptors (β2AR) and treatment of a variety of diseases and conditions, e.g., bronchoconstrictive diseases and conditions, as well as in the prevention or treatment of heart failure.

In some cases, the subject compounds are conformationally constrained analogs of biologically active β2AR agonists that are catecholamine type compounds such as isoprenaline, noradenraline, adenraline, salbutamol, orciprenaline, fenoterol, salmeterol, and the like. Each of the parent compounds is characterized by a 2-aminoethylphenyl scaffold. In general terms, a conformational constraint is included by cyclically linking the 2-carbon atom of the ethyl to the carbon at the ortho position of the phenyl ring to provide a phenyl-fused 5, 6 or 7-membered carbocyclic or heterocyclic ring. A variety of phenyl ring substituents and 2-amino substituents can be selected for incorporation at the remaining positions to provide for a desirable biological activity. In some cases, the subject compounds have phenyl ring substituents analogous to a parent biologically active β2AR agonist. In certain embodiments, the subject compound has a particular stereochemistry (e.g., as described herein) that provides for selectivity at β2AR over β1AR.

In some instances, the compound is of formula (I):

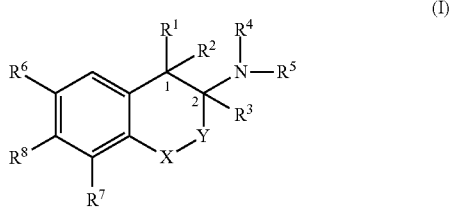

wherein:
R$^1$ and R$^2$ are independently hydrogen or hydroxyl;
R$^3$ is selected from hydrogen, alkyl and substituted alkyl;
R$^4$ and R$^5$ are independently selected from hydrogen, alkyl, substituted alkyl, aryl, substituted aryl, heteroaryl, substituted heteroaryl, heterocycle and substituted heterocycle;
R$^6$-R$^8$ are independently selected from hydrogen, hydroxyl, alkyl, substituted alkyl, halogen, alkoxy, substituted alkoxy, substituted amino and amino; and X—Y is selected from —CH$_2$—, —CH$_2$CH$_2$—, —OCH$_2$—, —CH$_2$CH$_2$CH$_2$— and CH═CH;
or a pharmaceutically acceptable salt thereof.

In certain embodiments of formula (I), R$^8$ is selected from hydroxyl and hydrogen. In certain embodiments of formula (I), when R$^8$ is hydrogen, R$^6$ and R$^7$ are not hydrogen. In certain embodiments of formula (I), when R$^8$ is hydroxyl.

The compounds of formula (I) can be diastereomeric as they have two stereocenters at the 1- and 2-positions as indicated. In general terms, the subject compounds of formula (I) are stereoisomerically enriched in a trans diastereomers. In some embodiments, the subject compounds of formula (I) are stereoisomerically enriched in a (1R,2R)-trans diastereomer. In some embodiments, the subject compounds of formula (I) are stereoisomerically enriched in a (1S,2S)-trans diastereomer. In some embodiments, the subject compounds of formula (I) are stereoisomerically enriched in trans diastereomers over cis-diastereomers (i.e., (1R,2S)-cis and/or (1S,2R)-cis diastereomers).

The diastereomer (also referred to as diasteroisomer) compound can also be referred to as a stereoisomer. Where a compound is described as a single diastereomer, it is understood that a sample of the compound may still contain some amounts of one or more of the other stereoisomers. The subject compound and compositions of the present disclosure can be enriched in the diastereomer that displays significant desirable in vitro and/or in vivo activity. By the term "enriched" is meant when the weight:weight ratio of the stereoisomers is at least approximately 1.05 or higher in favor of the diastereomer that displays significant in vitro and in vivo activity (e.g., the (R,R)-trans diastereomer) over the combined total of the other diastereomers.

In some instances, the subject compound and compositions of the present disclosure are substantially enriched in the stereoisomer that displays significant in vitro and/or in vivo activity. By the term "substantially enriched" is meant the weight:weight ratio of the diastereomers is about 1.5 or higher in favor of the diastereomer that displays significant in vitro and in vivo activity (e.g., the (R,R)-trans diastereomer) over the combined total of the other diastereomers. By the term "substantially enriched" is meant the weight:weight ratio of the diastereomers is about 1.5 or higher in favor of the diastereomer that displays significant in vitro and in vivo activity (e.g., the (R,R)-trans diastereomer) over the combined total of the other diastereomers, unless indicated otherwise. In certain instances, the term "substantially enriched" can be used to refer to a weight:weight ratio of about 1.5 or higher in favor of one trans-diastereomer over the other trans-diastereomer (e.g., (R,R)-trans over (S,S)-trans). In certain instances, the term "substantially enriched" is used to refer to a weight:weight ratio of about 1.5 or higher in favor of trans-diastereomers over the cis-diastereomers (e.g., (R,R)-trans and (S,S)-trans over (R,S)-cis and (S,R)-cis). In certain embodiments, the composition is substantially enriched in the stereoisomer by a weight:weight ratio that is about 2 or greater, about 3 or greater, about 4 or greater, such as about 5 or greater, about 6 or greater, about 7 or greater, about 8 or greater, about 9 or greater, about 10 or greater, or about 20 or greater in favor of the diastereomer that displays significant in vitro and/or in vivo activity over the combined total of the other diastereomers, unless indicated otherwise.

The terms "stereoisomerically enriched", "enriched stereoisomer", "diastereomerically enriched" and "enriched diastereomer" denote that the compound comprises 75% or more by weight of the desired stereoisomer, such as 80% or more by weight, 85% or more by weight, more than 90% or more by weight, more than 91% or more by weight, more than 92% or more by weight, more than 93% or more by weight, more than 94% or more by weight, more than 95% or more by weight, more than 96% or more by weight, or more than 97% or more by weight of the desired stereoisomer.

The term "stereoisomer enriched (R,R)-trans" refers to the compound comprising 75% or more by weight (R,R)-trans diastereomer and at most 25% by weight of other diastereoisomer(s), such as 80% or more by weight (R,R)-trans diastereomer and at most 20% by weight of other diastereoisomer(s), 90% or more by weight (R,R)-trans diastereomer and at most 10% by weight of other diastereoisomer(s), 91% or more by weight (R,R)-trans diastereomer and at most 9% by weight of other diastereoisomer(s), 92% or more by weight (R,R)-trans diastereomer and at most 8% by weight of other diastereoisomer(s), 93% or more by weight (R,R)-trans diastereomer and at most 7% by weight of other diastereoisomer(s), 94% or more by weight (R,R)-trans diastereomer and at most 6% by weight of other diastereoisomer(s), 95% or more by weight (R,R)-trans diastereomer and at most 5% by weight of other diastereoisomer(s), 96% or more by weight (R,R)-trans diastereomer and at most 4% by weight of other diastereoisomer(s), or 97% or more by weight (R,R)-trans diastereomer and at most 3% by weight of other diastereoisomer(s).

In certain embodiments, the compound is stereoisomerically pure (R,R)-trans diastereomer. In certain embodiments, the compound is stereoisomerically pure (S,S)-trans diastereomer. The term "stereoisomerically pure" refers to a compound that is present in diastereomeric excess of greater than 95%, e.g., by molar ratio. In some cases, the diastereomeric excess is greater than 96%. In some cases, the diastereomeric excess is greater than 97%. In some cases, the diastereomeric excess is greater than 98%. In certain instances, the diastereomeric excess is greater than 99%. The term "diastereomeric excess" refers to a difference between the amount of one diastereomer (e.g., (R,R)-trans diastereomer) and the amount of one or more other diastereomer (e.g., cis-diasteromers and/or (S,S)-trans diastereomer) that is present in a compound composition. Thus for example, diastereomeric excess of 96% refers to a compound composition having 98% of (R,R)-trans diastereomer and 2% of another diastereomer(s). In some embodiments of formula (I), the compound is stereoisomerically pure (R,R)-trans stereoisomer.

In some embodiments of formula (I), $R^8$ is hydroxyl and the compound is of formula (II):

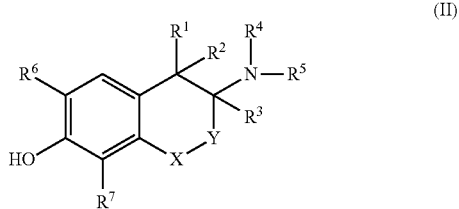

(II)

wherein:
$R^1$ and $R^2$ are independently hydrogen or hydroxyl;
$R^3$ is selected from hydrogen, alkyl and substituted alkyl;
$R^4$ and $R^5$ are independently selected from hydrogen, alkyl, substituted alkyl, cycloalkyl, substituted cycloalkyl, aryl, substituted aryl, heteroaryl, substituted heteroaryl, heterocycle and substituted heterocycle, connected via an optional linker;
$R^6$ and $R^7$ are independently selected from hydrogen, hydroxyl, alkyl, substituted alkyl, halogen, alkoxy, substituted alkoxy, substituted amino and amino; and
X—Y is selected from —CH$_2$—, —CH$_2$CH$_2$—, —CH$_2$CH$_2$CH$_2$— and CH═CH;
that is stereoisomerically enriched in a stereoisomer (e.g., a (R,R)-trans diastereomer);
or a pharmaceutically acceptable salt thereof.

In certain embodiments of formulae (I)-(II), $R^1$ is hydroxyl. In certain embodiments of formulae (I)-(II), $R^2$ is hydroxyl. In certain embodiments of formulae (I)-(II), $R^3$ is hydrogen. In certain embodiments of formulae (I)-(II), $R^3$ is alkyl, e.g., lower alkyl or unsubstituted linear lower alkyl such as methyl, ethyl or propyl. In certain embodiments of formulae (I)-(II), $R^3$ is substituted alkyl, e.g., substituted lower alkyl such as —CH$_2$OH or a branched lower alkyl such as isopropyl. In certain embodiments of formulae (I)-(II), $R^4$ is H. In certain embodiments of formulae (I)-(II), $R^5$ is H. In certain embodiments of formulae (I)-(II), $R^4$ and $R^5$ are both H. In certain embodiments of formulae (I)-(II), $R^4$ and $R^5$ are independently selected from alkyl and substituted alkyl. In certain embodiments of formulae (I)-(II), $R^4$ and/or $R^5$ is alkyl, e.g., lower alkyl or unsubstituted linear lower alkyl such as methyl, ethyl or propyl. In certain embodiments of formulae (I)-(II), $R^4$ and/or $R^5$ is substituted alkyl, e.g., substituted lower alkyl such as —CH$_2$OH or a branched lower alkyl such as isopropyl. In some cases of formula (I)-(II), $R^5$ is a substituted C1-C6-alkyl. In some cases of formula (I)-(II), $R^5$ is a substituted C1-C6alkyl including one or more substitutents selected from, halogen (e.g., fluoro), alkoxy (e.g., C1-C6-alkoxy), hydroxy and trialkylsilyl. In some embodiments of formula (I)-(II), $R^5$ is selected from H, methyl, ethyl, n-propyl, isopropyl, cyclopropyl, cyclobutyl, cyclopentyl, cyclohexyl, butyl, isobutyl, tert-butyl, 2-fluoro-ethyl, 3-fluoro-propyl, (FCH$_2$)$_2$CH—, (CH$_3$OCH$_2$)$_2$CH—, neopentyl-, (CH$_3$)$_3$Si—CH$_2$—, oxetan-3-yl, cyclobutylmethyl, 2,2-difluoro-cyclobutylmethyl. In certain embodiments of formulae (I)-(II), $R^4$ is H.

In certain embodiments of formulae (I)-(II), $R^6$ is H. In certain embodiments of formulae (I)-(II), $R^6$ is hydroxyl. In certain embodiments of formulae (I)-(II), $R^6$ is alkyl or substituted alkyl (e.g., —CH$_2$OH or —CH$_2$NH$_2$). In certain embodiments of formulae (I)-(II), $R^6$ is halogen, e.g., fluoro, chloro or bromo. In certain embodiments of formulae (I)-(II), $R^6$ is substituted amino or amino (e.g., —NRR' wherein R and R' are each independently H, alkyl or substituted alkyl). In certain embodiments of formulae (I)-(II), $R^7$ is H. In certain embodiments of formulae (I)-(II), $R^7$ is hydroxyl. In certain embodiments of formulae (I)-(II), $R^7$ is alkyl or substituted alkyl (e.g., —CH$_2$OH or —CH$_2$NH$_2$). In certain embodiments of formulae (I)-(II), $R^7$ is halogen, e.g., fluoro, chloro or bromo. In certain embodiments of formulae (I)-(II), $R^7$ is substituted amino or amino (e.g., —NRR' wherein R and R' are each independently H, alkyl or substituted alkyl).

In certain embodiments of formulae (I)-(II), X—Y is —CH$_2$— (e.g., X is a covalent bond and Y is —CH$_2$—). In certain embodiments of formulae (I)-(II), X—Y is —CH$_2$CH$_2$—.

In some embodiments of formula (II), $R^1$ is hydrogen and $R^2$ is hydroxyl; $R^3$ is hydrogen; $R^4$ and $R^5$ are independently selected from hydrogen, alkyl, substituted alkyl; $R^6$ is selected from hydrogen, hydroxyl, CH$_2$OH, halogen, substituted amino and amino; $R^7$ is selected from hydroxyl, $CH_2OH$, halogen, substituted amino and amino; and X—Y is —$CH_2CH_2$—.

In some embodiments of formula (II), $R^1$ is hydrogen and $R^2$ is hydroxyl; $R^3$ and $R^4$ are each is hydrogen; $R^5$ is alkyl or substituted alkyl; $R^6$ is selected from hydrogen, hydroxyl, $CH_2OH$, halogen, substituted amino and amino; $R^7$ is selected from hydroxyl, $CH_2OH$, halogen, substituted amino and amino; and X—Y is —$CH_2CH_2$—. In some embodiments of formula (II), $R^5$ is selected from linear lower alkyl, branched lower alkyl, cycloalkyl, substituted linear lower alkyl, substituted branched lower alkyl and substituted cycloalkyl. In some cases, $R^5$ is alkyl, e.g., lower alkyl or unsubstituted linear lower alkyl such as methyl, ethyl or propyl. In some cases, $R^5$ is substituted alkyl, e.g., substituted lower alkyl such as —$CH_2OH$ or a branched lower alkyl such as isopropyl. In some embodiments of formula (II), $R^5$ is selected from methyl, ethyl, n-propyl, isopropyl, cyclopropyl, cyclobutyl, cyclopentyl, cyclohexyl, butyl, isobutyl and tert-butyl.

In some embodiments of formula (II), $R^6$ is hydrogen. In some embodiments of formula (II), $R^7$ is hydroxyl. In some embodiments of formula (II), $R^7$ is $CH_2OH$. In some embodiments of formula (II), $R^1$ is hydrogen and $R^2$ is hydroxyl; $R^3$, $R^4$ and $R^6$ are each is hydrogen; $R^5$ is H, methyl, ethyl, isopropyl, cyclopropyl, cyclopentyl, tert-butyl; $R^7$ is selected from hydroxyl and $CH_2OH$; and X—Y is —$CH_2CH_2$—.

In some embodiments of formula (II), $R^5$ is hydrogen. In some embodiments of formula (II), $R^5$ is methyl. In some embodiments of formula (II), $R^5$ is ethyl. In some embodiments of formula (II), $R^5$ is isopropyl. In some embodiments of formula (II), $R^5$ is tert-butyl. In some embodiments of formula (II), $R^5$ is cyclopropyl. In some embodiments of formula (II), $R^5$ is cyclopentyl.

Stereoisomerically pure (R,R)-trans diastereomer of any one of the embodiments described herein are meant to be included.

In some embodiments of formulae (I)-(II), the compound is of formula (III):

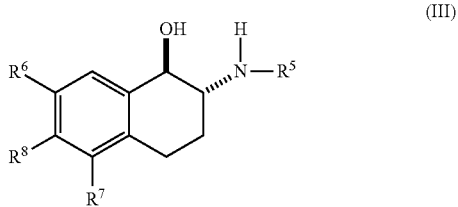

wherein $R^5$ is selected from hydrogen, alkyl, substituted alkyl, aryl, substituted aryl, heteroaryl, substituted heteroaryl, heterocycle and substituted heterocycle;

$R^6$-$R^8$ are independently selected from hydrogen, hydroxyl, alkyl, substituted alkyl, halogen, alkoxy, substituted alkoxy, substituted amino and amino, with the proviso that at least two of $R^6$-$R^8$ are not hydrogen.

In certain embodiments of formula (III), $R^5$ is selected from linear lower alkyl, branched lower alkyl, cycloalkyl, substituted linear lower alkyl, substituted branched lower alkyl and substituted cycloalkyl. In some cases of formula (III), $R^5$ is alkyl, e.g., lower alkyl or unsubstituted linear lower alkyl such as methyl, ethyl or propyl. In some cases of formula (III), $R^5$ is substituted alkyl, e.g., substituted lower alkyl such as —$CH_2OH$ or a branched lower alkyl such as isopropyl. In some cases of formula (III), $R^5$ is a substituted C1-C6-alkyl. In some cases of formula (III), $R^5$ is a substituted C1-C6alkyl including one or more substitutents selected from, halogen (e.g., fluoro), alkoxy (e.g., C1-C6-alkoxy), hydroxy and trialkylsilyl. In some embodiments of formula (III), $R^5$ is selected from methyl, ethyl, n-propyl, isopropyl, cyclopropyl, cyclobutyl, cyclopentyl, cyclohexyl, butyl, isobutyl, tert-butyl, $R^5$ is H, methyl, ethyl, isopropyl, cyclopropyl, cyclopentyl, tert-butyl, 2-fluoro-ethyl, 3-fluoro-propyl, (FCH$_2$)$_2$CH—, (CH$_3$OCH$_2$)$_2$CH—, neopentyl-, (CH$_3$)$_3$Si—CH$_2$—, oxetan-3-yl, cyclobutylmethyl, 2,2-difluoro-cyclobutylmethyl. In some embodiments of formula (III), $R^5$ is hydrogen. In some embodiments of formula (III), $R^5$ is methyl. In some embodiments of formula (III), $R^5$ is ethyl. In some embodiments of formula (III), $R^5$ is isopropyl. In some embodiments of formula (III), $R^5$ is tert-butyl. In some embodiments of formula (III), $R^5$ is cyclopropyl or substituted cyclopropyl. In some embodiments of formula (III), $R^5$ is cyclobutyl or substituted cyclobutyl. In some embodiments of formula (III), $R^5$ is cyclopentyl or substituted cyclopentyl. In certain embodiments of formula (I)-(III), $R^5$ is selected from heterocycle, e.g., a saturated heterocycle, and substituted heterocycle. Heterocycles of interest include, but are not limited to, azetidine, oxetane, tetrahydrofuran, pyrrolidine, tetrahydropyran and piperidine, which heterocycles can be unsubstituted or substituted. In certain embodiments of formula (I)-(III), $R^5$ is oxetane, e.g., oxetan-3-yl.

In certain embodiments of formula (III), $R^6$ is hydrogen. In some embodiments of formula (III), $R^6$ is hydroxyl. In some embodiments of formula (III), $R^6$ is $CH_2OH$. In certain embodiments of formula (III), $R^7$ is hydrogen. In some embodiments of formula (III), $R^7$ is hydroxyl. In some embodiments of formula (III), $R^7$ is $CH_2OH$. In certain embodiments of formula (III), $R^8$ is hydrogen. In some embodiments of formula (III), $R^8$ is hydroxyl. In some embodiments of formula (III), $R^8$ is $CH_2OH$.

In certain embodiments of formula (III), $R^6$ is hydrogen, and $R^7$ and $R^8$ are independently selected from hydroxy and $CH_2OH$. In certain embodiments of formula (III), $R^6$ is hydrogen, and $R^7$ is $CH_2OH$ and $R^8$ is hydroxy. In certain embodiments of formula (III), $R^6$ is hydrogen, and $R^7$ and $R^8$ are each hydroxy. In certain embodiments of formula (III), $R^8$ is hydrogen, and $R^6$ and $R^8$ are independently selected from hydroxy and $CH_2OH$.

In some embodiments of formulae (I)-(III), the compound is selected from one of the following compounds:

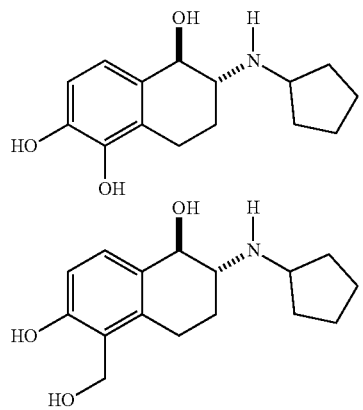

-continued

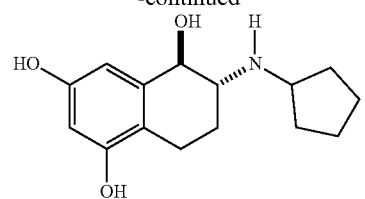
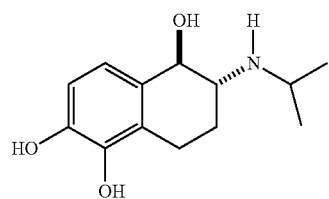
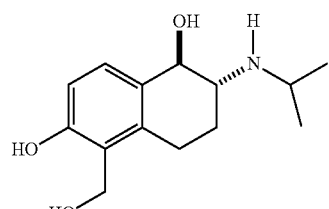
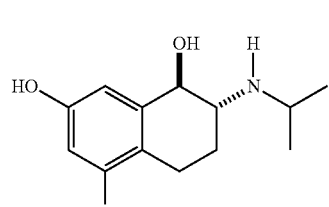
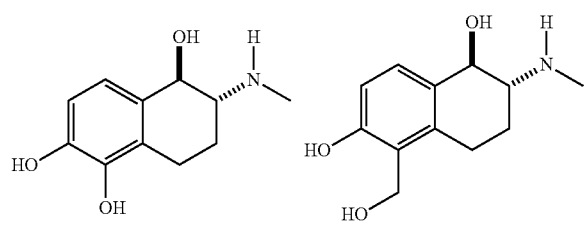
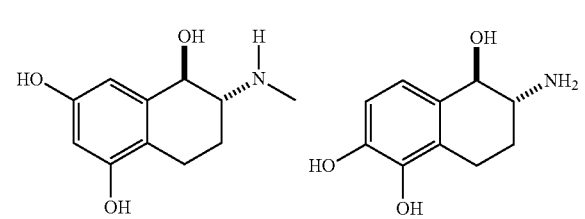
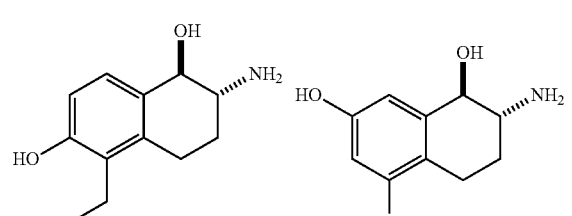

In some embodiments of formulae (I)-(III), the compound is of formula (V):

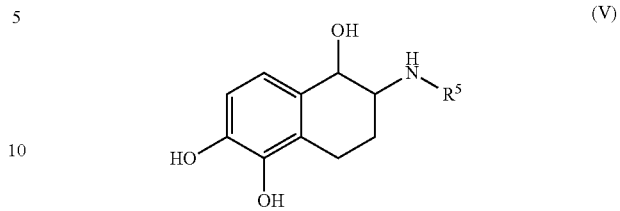

(V)

wherein $R^5$ is as defined above. In some instances of formula (V), $R^5$ is selected from aryl, heteroaryl, substituted aryl, substituted aryl, linked to the nitrogen atom via an optional linker.

In some embodiments of formulae (I)-(III), the compound is selected from one of compounds 1-13 of formula (V):

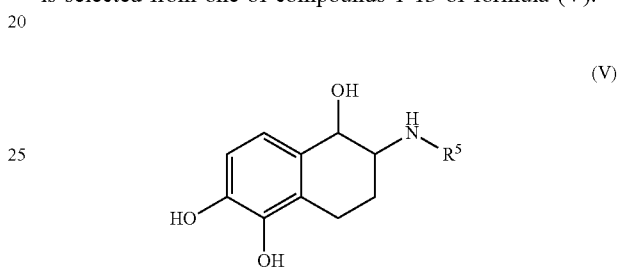

(V)

| Compounds of formula (V) | $R^5$ |
|---|---|
| 1 | $CH_3$ |
| 2 | iso-propyl |
| 3 | H |
| 4 | cyclopentyl |
| 5 | 2-fluoro-ethyl |
| 6 | 3-fluoro-propyl |
| 7 | $(FCH_2)_2CH-$ |
| 8 | $(CH_3OCH_2)_2CH-$ |
| 9 | neopentyl- |
| 10 | $(CH_3)_3Si-CH_2-$ |
| 11 | oxetan-3-yl |
| 12 | cyclobutylmethyl |
| 13 | 2,2-difluoro-cyclobutylmethyl |

In some embodiments of formulae (I)-(III), the compound is selected from one of compounds 1-10 of formula (V) as defined above where the compound is a stereoisomerically enriched or pure (5R,6R)-trans diastereomer of the formula (Va):

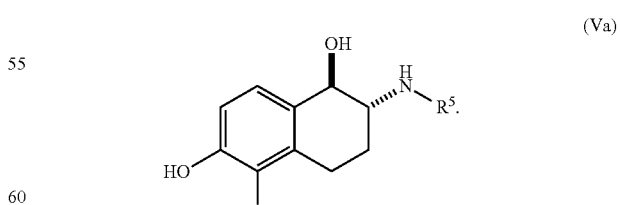

(Va)

In some embodiments of formula (Va), $R^5$ is -L-Ar, wherein L is a covalent bond or a linker, and Ar is aryl, substituted aryl, heteroaryl or substituted heteroaryl. In certain instances, L is a covalent bond. In certain cases, L is a linker having In some embodiments of formulae (V)-(Va), linker (L) is a linker having a backbone of 30 atoms or less in length, such as 20 atoms or less, 18 atoms or less, 16 atoms or less, 14 atoms or less, 12 atoms or less, 10 atoms or less, and in some cases, having 6 atoms or more, such as 8 atoms or more in length. In some embodiments of formulae (V)-(Va), linker (L) is a linker having a backbone of 6-30 atoms in length, such as 8-30 atoms, 8-20 atoms, 10-16, 10-14 or 10-12 atoms in length. In certain cases, the linker is a C6-C30 alkylene or substituted a C6-C30 alkylene, where one or more (e.g., 1, 2, 3 or 4) of the carbon atoms on the linker backbone are replaced with an oxo (—O—).

In some embodiments of formulae (V)-(Va), Ar is a phenyl or substituted phenyl. In certain instances, the substituted phenyl is a phenyl fused to a second carbocyclic or heterocyclic ring, that is itself optionally further substituted. In some embodiments of formulae (V)-(Va), Ar is a pyridyl or substituted pyridyl. In certain instances, the substituted pyridyl is a pyridyl fused to a second carbocyclic or heterocyclic ring, that is itself optionally further substituted.

In some embodiments of formulae (V)-(Va), the compound is selected from one of the following structures:

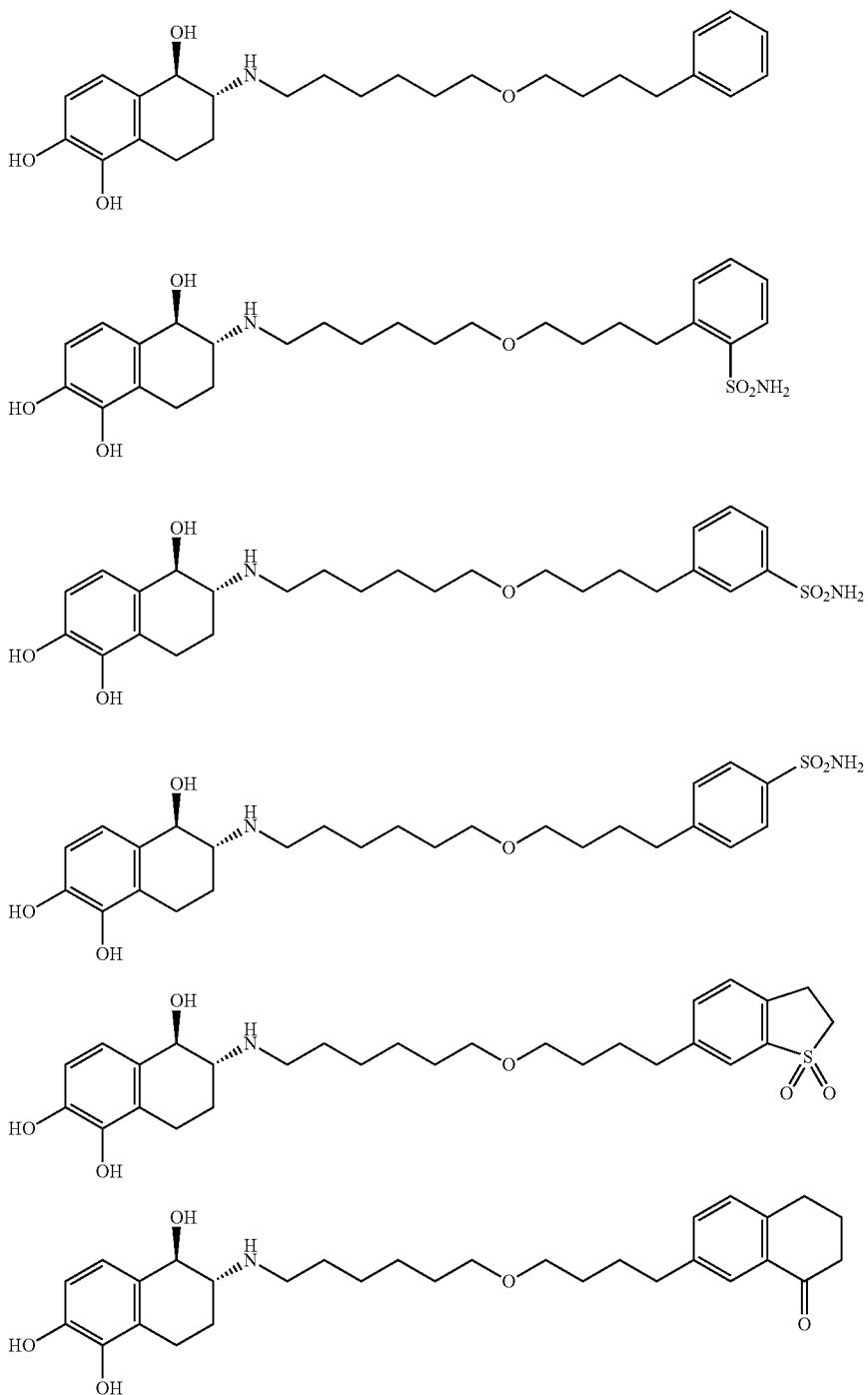

-continued
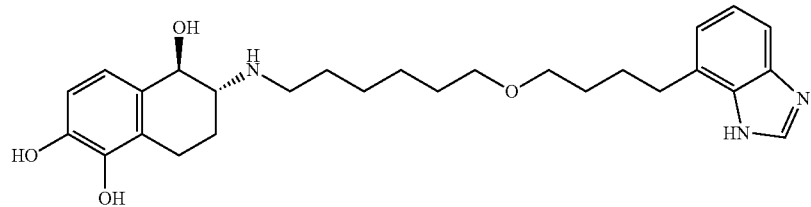
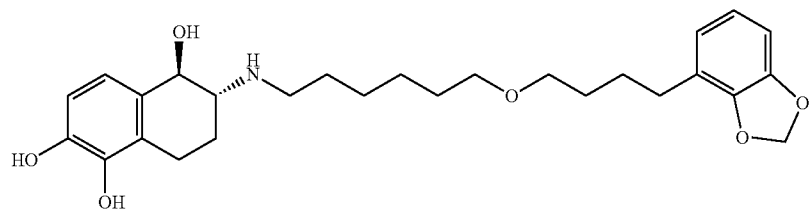
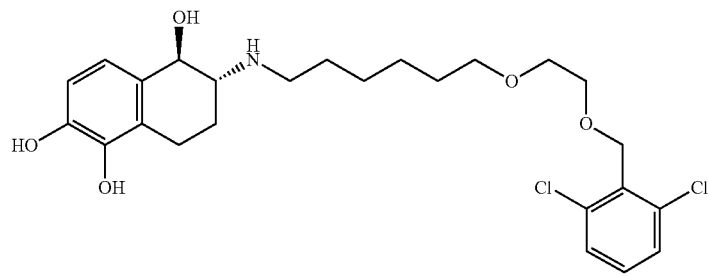
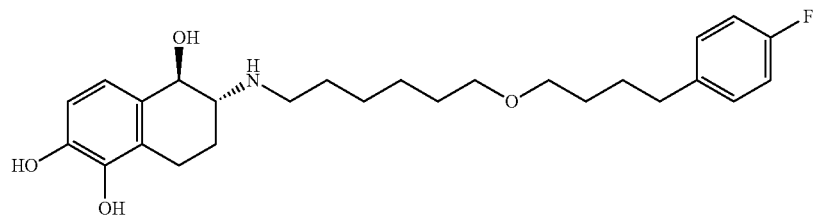
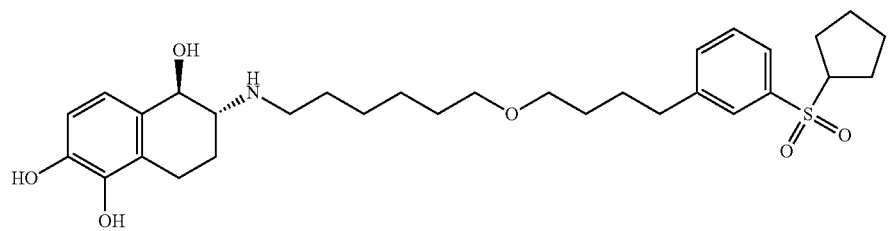
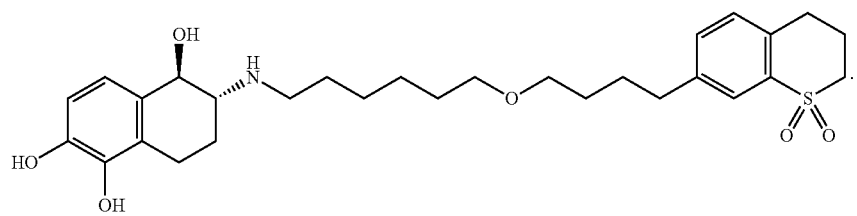

In some embodiments of formulae (V)-(Va), linker (L) is a covalent bond, and the compound has the structure:

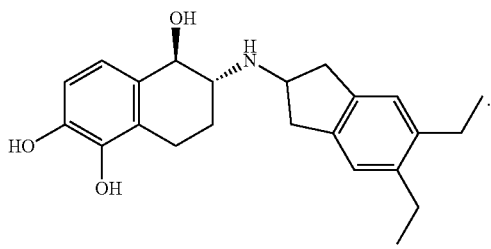

In some embodiments, the compound is a (S,S)-trans diastereomer of formula (IV):

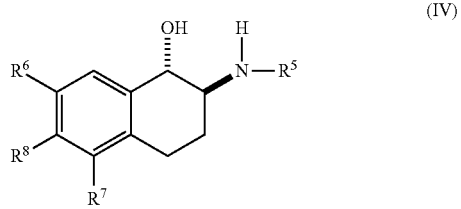

wherein

R⁵ is selected from hydrogen, alkyl, substituted alkyl heterocycle and substituted heterocycle;

R⁶-R⁸ are independently selected from hydrogen, hydroxyl, alkyl, substituted alkyl, halogen, alkoxy, substituted alkoxy, substituted amino and amino, with the proviso that at least two of R⁶-R⁸ are not hydrogen.

In certain embodiments of formula (IV), R⁵ is selected from linear lower alkyl, branched lower alkyl, cycloalkyl, substituted linear lower alkyl, substituted branched lower alkyl and substituted cycloalkyl. In some cases of formula (IV), R⁵ is alkyl, e.g., lower alkyl or unsubstituted linear lower alkyl such as methyl, ethyl or propyl. In some cases of formula (IV), R⁵ is substituted alkyl, e.g., substituted lower alkyl such as —CH₂OH or a branched lower alkyl such as isopropyl. In some embodiments of formula (IV), R⁵ is selected from methyl, ethyl, n-propyl, isopropyl, cyclopropyl, cyclobutyl, cyclopentyl, cyclohexyl, butyl, isobutyl and tert-butyl. In some embodiments of formula (IV), R⁵ is hydrogen. In some embodiments of formula (IV), R⁵ is methyl. In some embodiments of formula (IV), R⁵ is ethyl. In some embodiments of formula (IV), R⁵ is isopropyl. In some embodiments of formula (IV), R⁵ is tert-butyl. In some embodiments of formula (IV), R⁵ is cyclopropyl or substituted cyclopropyl. In some embodiments of formula (IV), R⁵ is cyclobutyl or substituted cyclobutyl. In some embodiments of formula (IV), R⁵ is cyclopentyl or substituted cyclopentyl. In certain embodiments of formula (IV), R⁵ is selected from heterocycle, e.g., a saturated heterocycle, and substituted heterocycle. Heterocycles of interest include, but are not limited to, azetidine, oxetane, tetrahydrofuran, pyrrolidine, tetrahydropyran and piperidine, which heterocycles can be unsubstituted or substituted. In certain embodiments of formula (IV), R⁵ is oxetane.

In certain embodiments of formula (IV), R⁶ is hydrogen. In some embodiments of formula (IV), R⁶ is hydroxyl. In some embodiments of formula (IV), R⁶ is CH₂OH. In certain embodiments of formula (IV), R⁷ is hydrogen. In some embodiments of formula (IV), R⁷ is hydroxyl. In some embodiments of formula (IV), R⁷ is CH₂OH. In certain embodiments of formula (IV), R⁸ is hydrogen. In some embodiments of formula (IV), R⁸ is hydroxyl. In some embodiments of formula (IV), R⁸ is CH₂OH.

In certain embodiments of formula (IV), R⁶ is hydrogen, and R⁷ and R⁸ are independently selected from hydroxy and CH₂OH. In certain embodiments of formula (IV), R⁶ is hydrogen, and R⁷ is CH₂OH and R⁸ is hydroxy. In certain embodiments of formula (IV), R⁶ is hydrogen, and R⁷ and R⁸ are each hydroxy. In certain embodiments of formula (IV), R⁸ is hydrogen, and R⁶ and R⁸ are independently selected from hydroxy and CH₂OH.

Aspects of the present disclosure include a β2AR selective compound (e.g., as described herein), salts thereof (e.g., pharmaceutically acceptable salts), and/or solvate, hydrate and/or prodrug forms thereof. It will be appreciated that all permutations of salts, solvates, hydrates, and prodrugs are meant to be encompassed by the present disclosure.

In some embodiments, the subject β2AR selective compound (e.g., as described herein), or a prodrug form thereof, are provided in the form of a pharmaceutically acceptable salt. Compounds containing an amine or nitrogen containing heteroaryl group may be basic in nature and accordingly may react with any number of inorganic and organic acids to form pharmaceutically acceptable acid addition salts. Acids commonly employed to form such salts include inorganic acids such as hydrochloric, hydrobromic, hydriodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-I,4-dioate, hexyne-I,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycollate, maleate, tartrate, methanesulfonate, propanesulfonates, naphthalene-1-sulfonate, naphthalene-2-sulfonate, mandelate, hippurate, gluconate, lactobionate, and the like salts. In certain specific embodiments, pharmaceutically acceptable acid addition salts include those formed with mineral acids such as hydrochloric acid and hydrobromic acid, and those formed with organic acids such as fumaric acid and maleic acid.

In some embodiments, the subject β2AR selective compound is provided in a prodrug form. "Prodrug" refers to a derivative of an active agent that requires a transformation within the body to release the active agent. In certain embodiments, the transformation is an enzymatic transformation. Prodrugs are frequently, although not necessarily, pharmacologically inactive until converted to the active agent. "Promoiety" refers to a form of protecting group that, when used to mask a functional group within an active agent, converts the active agent into a prodrug. In some cases, the promoiety will be attached to the drug via bond(s) that are cleaved by enzymatic or non-enzymatic means in vivo. Any convenient prodrug forms of the subject compounds can be prepared, e.g., according to the strategies and methods described by Rautio et al. ("Prodrugs: design and clinical applications", Nature Reviews Drug Discovery 7, 255-270 (February 2008)). In some cases, the promoiety is attached to a hydroxy group of the subject compounds. In certain cases, the promoiety is an acyl or substituted acyl group. In certain cases, the promoiety is an alkyl or substituted alkyl group, e.g., that forms an ester functional group when attached to a carboxylic acid group of the subject compounds.

In some embodiments, the subject β2AR selective compound, prodrugs, or salts thereof is provided in the form of a solvate (e.g., a hydrate). The term "solvate" as used herein refers to a complex or aggregate formed by one or more molecules of a solute, e.g. a prodrug or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

Pharmaceutical Preparations

Also provided are pharmaceutical preparations. Pharmaceutical preparations are compositions that include a β2AR selective compound (e.g., as described herein) (either alone or in the presence of one or more additional active agents) present in a pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a β2AR selective compound is formulated for administration to a mammal. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used.

When administered to a mammal, the compound and compositions of the present disclosure and pharmaceutically acceptable vehicles, excipients, or diluents may be sterile. In some instances, an aqueous medium is employed as a vehicle when the subject compound is administered intravenously, such as water, saline solutions, and aqueous dextrose and glycerol solutions.

Pharmaceutical compositions can take the form of capsules, tablets, pills, pellets, lozenges, powders, granules, syrups, elixirs, solutions, suspensions, emulsions, suppositories, or sustained-release formulations thereof, or any other form suitable for administration to a mammal. In some instances, the pharmaceutical compositions are formulated for administration in accordance with routine procedures as a pharmaceutical composition adapted for oral or intravenous administration to humans. Examples of suitable pharmaceutical vehicles and methods for formulation thereof are described in Remington: The Science and Practice of Pharmacy, Alfonso R. Gennaro ed., Mack Publishing Co. Easton, Pa., 19th ed., 1995, Chapters 86, 87, 88, 91, and 92, incorporated herein by reference. The choice of excipient is determined in part by the compound, as well as by the particular method used to administer the composition. Accordingly, there is a wide variety of suitable formulations of the subject pharmaceutical compositions.

Administration of the subject compound may be systemic or local. In certain embodiments administration to a mammal will result in systemic release of the compound (for example, into the bloodstream). Methods of administration may include inhalation via nebulizer or inhaler, enteral routes, such as oral, buccal, sublingual, and rectal; topical administration, such as transdermal and intradermal; and parenteral administration. Suitable parenteral routes include injection via a hypodermic needle or catheter, for example, intravenous, intramuscular, subcutaneous, intradermal, intraperitoneal, intraarterial, intraventricular, intrathecal, and intracameral injection and non-injection routes, such as intravaginal rectal, or nasal administration. In certain embodiments, the compound and compositions of the present disclosure are administered subcutaneously. In certain embodiments, compound and compositions of the present disclosure are directly administered to a subject in need of treatment via nebulization. In certain embodiments, the compound and compositions of the present disclosure are administered orally. In certain embodiments, it may be desirable to administer the compound locally to the area in need of treatment. This may be achieved, for example, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

The subject compounds and compositions can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer, inhaler or an atomizer. In some cases, the subject compounds and compositions are formulated into a dry powder formulation suitable for inhalation. See e.g., U.S. Pat. No. 10,028,964 for description of dry powder formulation ingredients and formulations which can be adapted for use in the subject compositions, devices and methods.

The β2AR selective compound can be formulated into preparations for injection by dissolving, suspending or emulsifying the compound in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The β2AR selective compound may also be formulated for oral administration. For an oral pharmaceutical formulation, suitable excipients include pharmaceutical grades of carriers such as mannitol, lactose, glucose, sucrose, starch, cellulose, gelatin, magnesium stearate, sodium saccharine, and/or magnesium carbonate. For use in oral liquid formulations, the composition may be prepared as a solution, suspension, emulsion, or syrup, being supplied either in solid or liquid form suitable for hydration in an aqueous carrier, such as, for example, aqueous saline, aqueous dextrose, glycerol, or ethanol, preferably water or normal saline. If desired, the composition may also contain minor amounts of non-toxic auxiliary substances such as wetting agents, emulsifying agents, or buffers. In some embodiments, formulations suitable for oral administration can include (a) liquid solutions, such as an effective amount of the compound dissolved in diluents, such as water, or saline; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can include the active ingredient in a flavor, usually sucrose and acacia or tragacanth, as well as pastilles including the active ingredient in an inert base, such as gelatin and glycerin, or sucrose and acacia, emulsions, gels, and the like containing, in addition to the active ingredient, such excipients as are described herein.

In some embodiments, formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for topical administration may be presented as creams, gels, pastes, or foams, containing, in addition to the active ingredient, such carriers as are appropriate. In some embodiments, the topical formulation contains one or more components selected from a structuring agent, a thickener or gelling agent, and an emollient or lubricant. Frequently employed structuring agents include long chain alcohols, such as stearyl alcohol, and glyceryl ethers or esters and oligo(ethylene oxide) ethers or esters thereof. Thickeners and gelling agents include, for example, polymers of acrylic or methacrylic acid and esters thereof, polyacrylamides, and naturally occurring thickeners such as agar, carrageenan, gelatin, and guar gum. Examples of emollients include triglyceride esters, fatty acid esters and amides, waxes such as beeswax, spermaceti, or carnauba wax, phospholipids such as lecithin, and sterols and fatty acid esters thereof. The topical formulations may further include other components, e.g., astringents, fragrances, pigments, skin penetration enhancing agents, sunscreens (e.g., sunblocking agents), etc.

Unit dosage forms for oral or rectal administration such as syrups, elixirs, and suspensions may be provided wherein each dosage unit, for example, teaspoonful, tablespoonful, tablet or suppository, contains a predetermined amount of the subject compound or composition. Similarly, unit dosage forms for injection or intravenous administration may include the compound in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of the compound calculated in an amount sufficient to produce the desired effect in association with a pharmaceutically acceptable diluent, carrier or vehicle. The specifications for the novel unit dosage forms of the present disclosure depend on the compound and the effect to be achieved, and the pharmacodynamics associated with the compound in the host. In pharmaceutical dosage forms, the compound may be administered in the form of a free base, a pharmaceutically acceptable salt, or the compound may also be used alone or in appropriate association, as well as in combination, with other pharmaceutically active compounds.

Dose levels can vary as a function of the specific composition, the nature of the delivery vehicle, and the like. Desired dosages for the compound are readily determinable by a variety of means. The dose administered to an animal, particularly a human, in the context of the present disclosure should be sufficient to effect a prophylactic or therapeutic response in the animal over a reasonable time frame, e.g., as described in greater detail herein. Dosage will depend on a variety of factors including the strength of the compound employed, the condition of the animal, and the body weight of the animal, as well as the severity of the illness and the stage of the disease. The size of the dose will also be determined by the existence, nature, and extent of any adverse side-effects that might accompany the administration of the compound.

Methods of Selectively Activating β2AR

Aspects of the present disclosure include a method for selectively activating a beta-2 adrenergic receptor (β2AR) using a subject compound (e.g., as described herein). The β2AR, also known as ADRB2, is a cell membrane-spanning beta-adrenergic receptor that interacts with (binds) epinephrine, a hormone and neurotransmitter (ligand synonym, adrenaline) whose signaling, via a downstream L-type calcium channel interaction, mediates physiological responses such as smooth muscle relaxation and bronchodilation. The terms adrenergic receptor and adrenoceptor are used interchangeably herein. The terms beta-2 adrenergic receptor, β2 adrenoreceptor, β2AR, $β_2$-AR are used interchangeably herein.

Applicants have demonstrated that conformationally constrained analogs of catecholamine type compounds (e.g., isoprenaline, adrenaline, noradrenaline and the like) having a particular stereochemistry (e.g., as described herein) selectively bind to $β_2$-ARs over $β_1$-ARs and can provide for selective activation of $β_2$-ARs over $β_1$-ARs. In addition, Applicants discovered that the subject agonist compounds show significant bias for β-arrestin recruitment over G protein-promoted signaling in agonizing $β_2$-AR.

In some cases, this method can be applied to activate $β_2$-AR in a cell and (e.g., modulate downstream biological activity of a $β_2$-AR of interest) and finds use in a variety of therapeutic and research applications. Embodiments of the present disclosure include methods of activating a beta-2 adrenergic receptor in a cell.

The subject methods, compound and compositions may reduce or avoid the impact or activity of activation of a beta-1 adrenergic receptor in a cell. The impact or activity that is reduced by the subject compounds may vary, depending on the cell. As such, the method includes contacting a cell with a $β_2$-selective adrenergic receptor agonist compound to selectively bind a $β_2$-AR and activate a $β_2$-AR signaling pathway or activity in the cell.

The selectivity of a subject compound for $β_2$-AR over $β_1$-AR can be assessed using a binding assay to determine relative binding affinities, e.g., as described herein in the experimental section. In some cases, the subject compounds have a relative binding affinity that is 100-fold or more selective for $β_2$-AR over $β_1$-AR, such as 200-fold or more, 300-fold or more, 400-fold or more, 500-fold or more, 600-fold or more, 700-fold or more, 800-fold or more, 900-fold or more, 1000-fold or more, or even more for $β_2$-AR over $β_1$-AR.

Any convenient assays may be used to determine the binding to and/or activity of an adrenergic receptor of interest in a cell. The $\beta_2$-AR activity in a cell in response to a compound can be determined relative to a control, e.g., a cell not contacted with the subject compound, where the magnitude of activation may be 10% or more, such as 20% or more, 30% or more, 50% or more, 100% or more, 200% or more, 1000% or more, such as by 2-fold or more, by 5-fold or more, by 10-fold or more, by 20-fold or more, by 50-fold or more, by 100-fold or more, 300-fold or more, 1000-fold or more, or even more. In some instances of the method, the subject compound selectively enhances the activity of a $\beta_2$-AR in the cell, e.g., over other receptors such as a corresponding $\beta_1$-AR. By "enhances the activity" is meant that $\beta_2$-AR activity is increased relative to a control, e.g., a cell not contacted with the compound, by 10% or more, such as 20% or more, 30% or more, 50% or more, 100% or more, 200% or more, 1000% or more, such as by 2-fold or more, by 5-fold or more, by 10-fold or more, by 20-fold or more, by 50-fold or more, by 100-fold or more, 300-fold or more, 1000-fold or more, or even more. In some instances, an effective amount of a compound that finds use in the subject methods is an β2AR activating amount, i.e., an amount of the compound that activates the β2AR by 20% or more, such as 30% or more, 40% or more, 50% or more, 60% or more, 70% or more, 80% or more, 90% or more, 100% or more, 200% or more, 1000% or more, as compared to a control in the absence of the compound.

Any convenient assays may be utilized to directly or indirectly assess the level of activity $\beta_2$-AR pathway or a level of a downstream signaling molecule. In some cases, the recruitment of a β-arrestin (e.g., β-arrestin-2) by the AR of interest can be assessed, e.g., as described herein in the experimental section.

Any convenient cells and/or tissues that include a β2AR may be targeted for use in the subject methods. In some instances, the types of cells in which the compound exhibit activity are ones that include a β2AR. In some embodiments of the method, the cell is an animal cell or a yeast cell. In certain instances, the cell is a mammalian cell. Cells and tissues of interest include those of respiratory system (e.g., bronchioles), muscles (e.g., smooth muscle), eye, digestive system, and circulatory system (e.g., blood vessel cells).

In practicing methods according to certain embodiments, an effective amount of the compound is provided in the target cell or cells. In some instances, the effective amount of the compound is provided in the cell by contacting the cell with the compound. Contact of the cell with the compound may occur using any convenient protocol. The protocol may provide for in vitro or in vivo contact of the compound with the target cell, depending on the location of the target cell. In some instances, the cell is in vitro. In certain instances, the cell is in vivo. Contact may or may not include entry of the compound into the cell. For example, where the target cell is an isolated cell, the compound may be introduced directly into the cell under cell culture conditions permissive of viability of the target cell. The choice of method is generally dependent on the type of cell being contacted and the nature of the compound, and the circumstances under which the transformation is taking place (e.g., in vitro, ex vivo, or in vivo).

Alternatively, where the target cell or cells are part of a multicellular organism, the subject compound may be administered to the organism or subject in a manner such that the compound is able to contact the target cell(s), e.g., via an in vivo or ex vivo protocol. By "in vivo," it is meant in the target construct is administered to a living body of an animal. By "ex vivo" it is meant that cells or organs are modified outside of the body. Such cells or organs are in some cases returned to a living body.

Methods of Treatment

The β2AR selective compounds of the present disclosure find use in treatment of a condition or disease in a subject in which modulation of the activity of a β2 adrenergic receptor is desirable (e.g., as described herein). Aspects of the method include administering to a subject in need thereof a therapeutically effective amount of a β2AR selective compounds to treat the subject. By "a therapeutically effective amount" is meant the concentration of a compound that is sufficient to elicit the desired biological effect (e.g., treatment of the condition or disease). By "treatment" is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease; and/or (iii) relief, that is, causing the regression of clinical symptoms.

A variety of bronchoconstrictive diseases and conditions can be treated using the subject methods. Bronchoconstriction refers to a reduction in the caliber of a bronchus or bronchi. As used herein, undesired and/or uncontrolled bronchoconstriction refers to bronchoconstriction that results in or from a pathological symptom or condition. Examples of diseases or conditions which may be treated with compounds of the invention include, but are not limited to: asthma including bronchial asthma and asthma attacks, bronchial asthma, exercise-induced bronchoconstriction and chronic obstructive pulmonary disease (COPD). In some instances, the subject compounds have a bronchodilator effect. Standard physiological, pharmacological and biochemical procedures are available for testing the compositions provided herein to identify those that possess bronchodilatory activity. In vitro and in vivo assays that may be used to evaluate bronchodilatory activity are well known to those of skill in the art. See also, e.g., U.S. Pat. Nos. 3,994,974, and 6,068,833;

In some embodiments, the subject method includes oral administration of a composition provided herein. In some embodiments, the subject method includes a parenteral administration route such as injection via a hypodermic needle or catheter of a composition provided herein. In certain embodiments, the composition is directly administered to a subject in need of such treatment via nebulization, e.g., without dilution or other modification of the composition prior to administration.

In the treatment of bronchoconstrictive diseases, sufficient amount of the inhaled drug should reach the local site of action in order to be efficacious. It is known that different delivery methods and delivery devices have different deposition characteristics. Consequently, under optimal inhalation conditions, doses from different delivery methods and delivery devices result in different delivered doses and different amounts deposited at the active site. The actual dose reaching the active site also depends upon the amount of drug particles included in the delivered dose and the inhalation characteristics of the patient. No correlation between the amount of drug administered by dry powder inhalers (DPIs) or metered dose inhalers (MDIs) and the actual amount that gets deposited at the active site has been established so far. Nor has a correlation been established between DPI or MDI dosages and nebulization dosages.

In some cases, the compositions provided herein are intended for administration to a subject in need of such treatment via nebulization. Nebulizers that nebulize liquid formulations containing no propellant are suitable for use with the compositions provided herein. The nebulizer and can be unit dose or multidose. Nebulizers are available from, e.g., Pari GmbH (Starnberg, Germany), DeVilbiss Healthcare (Heston, Middlesex, UK), Healthdyne, Vital Signs, Baxter, Allied Health Care, Invacare, Hudson, Omron, Bremed, AirSep, Luminscope, Medisana, Siemens, Aerogen, Mountain Medical, Aerosol Medical Ltd. (Colchester, Essex, UK), AFP Medical (Rugby, Warwnvickshire, UK), Bard Ltd. (Sunderland, UK), Carri-Med Ltd. (Dorking, UK), Plaem Nuiva (Brescia, Italy), Henleys Medical Supplies (London, UK), Intersurgical (Berkshire, UK), Lifecare Hospital Supplies (Leics, UK), Medic-Aid Ltd. (West Sussex, UK), Medix Ltd. (Essex, UK), Sinclair Medical Ltd. (Surrey, UK), and many others.

Nebulizers for use herein include, but are not limited to, jet nebulizers (optionally sold with compressors), ultrasonic nebulizers, and others. Exemplary jet nebulizers for use herein include Pari LC plus/ProNeb, Pari LC plus/ProNeb Turbo, Pari LC plus/Dura Neb 1000 & 2000, Pari LC plus/Walkhaler, Pari LC plus/Pari Master, Pari LC star, Omron CompAir XL Portable Nebulizer System (NE-C18 and JetAir Disposable nebulizer), Omron CompAir Elite Compressor Nebulizer System (NE-C21 and Elite Air Reusable Nebulizer), Pari LC Plus or Pari LC Star nebulizer with Proneb Ultra compressor, Pulmo-aide; Pulmo-aide LT, Pulmo-aide traveler, Invacare Passport, Inspiration Healthdyne 626, Pulmo-Neb Traverler, DeVilbiss 646, Whisper Jet, Acorn II, Misty-Neb, Allied aerosol, Schuco Home Care, Lexan Plasic Pocet Neb, SideStream Hand Held Neb, Mobil Mist, Up-Draft, Up-Draft II, T Up-Draft, ISO-NEB, AVA-NEB, Micro Mist, and PulmoMate. Exemplary ultrasonic nebulizers for use herein include MicroAir, UltraAir, Siemens Ultra Nebulizer 145, CompAir, Pulmosonic, Scout, 5003 Ultrasonic Neb, 5110 Ultrasonic Neb, 5004 Desk Ultrasonic Neb, Mystique Ultrasonic, Luminscope's Ultrasonic Nebulizer, Medisana Ultrasonic Nebulizer, Microstat Ultrasonic Nebulizer, and MABISMist Hand Held Ultrasonic Nebulizer. Other nebulizers for use herein include 5000 Electromagnetic Neb, 5001 Electromagnetic Neb 5002 Rotary Piston Neb, Lumineb I Piston Nebulizer 5500, AERONEB™ Portable Nebulizer System, AERO-DOSE™ Inhaler, AeroEclipse Breath Actuated Nebulizer, HALOLITE™ system (Profile Therapeutics), AKITA® systems (InaMed, Germany), Mystic system (BattellePharma), RESPIMAT® (Boehringer Ingelheim), AERX® (Aradigm), and E-FLOW™ (Pari).

Depending on the nebulizer used, the volume of the inhalation solution nebulized in one embodiment, is about 0.1 mL to 3 mL, or 0.1 mL to 3 mL. In another embodiment, the volume is about 2 mL, or 2 mL. In another embodiment, the volume is about 1 mL, or 1 mL. In another embodiment, the volume is about 0.5 mL, or 0.5 mL.

The formulations of the present disclosure can be used with any convenient inhaler device to deliver a therapeutic amount of the active compound in one or more actuations (shots or puffs) of the inhaler. In some cases, the inhaler is a dry powder inhaler. Dry powder inhalers (DPIs) can be divided into two basic types: i) single dose inhalers, for the administration of single subdivided doses of the active compound; each single dose is usually filled in a capsule; and ii) multidose inhalers pre-loaded with quantities of active compound sufficient for longer treatment cycles. Dry powder formulation is suitable for multidose DP's comprising a reservoir from which individual therapeutic dosages can be withdrawn on demand through actuation of the device, for example that described in WO 2004/012801. Other multi-dose devices that may be used are for instance the DISKUS™ of GlaxoSmithKline, the TURBOHALER™ of AstraZeneca, TWISTHALER™ of Schering and CLICK-HALER™ of Innovata. As marketed examples of single-dose devices, there may be mentioned ROTOHALER™ of GlaxoSmithKline and HANDIHALER™ of Boehringer Ingelheim.

In certain instances, the inhaler device is a pressurized metered dose inhaler (pMDI). A pMDI can include a canister which contains a liquid phase such as a propellant (which may also include low volatility co-solvents) in which the active pharmaceutical ingredient (API) is present either in solution or suspended in the form of micronised particles (either micrometers or nanometers in diameter). The propellants commonly used are hydrofluoroalkanes (HFA) such as HFA 134a (tetrafluorethane) and HFA 227ea (heptafluoropropane). Solvents of relatively low volatility e.g. ethanol, and/or formulation modifiers e.g. glycerol can be included in the formulations to enhance API solubility in the propellant to yield a solution formulation, or to modify the aerosol properties of the formulation. See e.g., U.S. Pat. No. 9,981,092.

In some embodiments, a subject compound or composition may be delivered by an autoinjector, i.e., a hand-held medical device that injects a measured dose (e.g., 0.1-0.5 mg) of a compound using autoinjector technology. Any convenient autoinjector devices can be adapted for use with the subject compounds and methods. An "automatic injection device" or "autoinjector" (used interchangeably herein) is intended to refer generally to a device that enables an individual (also referred to herein as a user or a patient) to self-administer a dosage of a liquid substance, such as a subject compound, including a formulation in liquid form, wherein the device differs from a standard syringe by the inclusion of a mechanism for automatically delivering the medication to the individual by injection when the mechanism is activated. These devices (loaded with epinephrine) are often used for the treatment of anaphylaxis and are commonly referred to as "Epipen", and can be adapted for use in the subject methods. When anaphylaxis is suspected, a solution containing the subject compound should be injected into muscle as soon as possible. The injection may be repeated every 5 to 15 minutes if there is insufficient response. An autoinjector may comprise: i. four latch mechanisms that hold the plunger secure, ii. loaded spring that drives the plunger and the needle (toward the right), iii. a plunger, iv. a solution of the subject compound and v. an outer body. When the outer body is retracted the needle is exposed and the latch mechanism is triggered. After triggering, the outer body springs back to cover the needle after use. The needle exits through a protective barrier when this is pressed against the skin.

The subject methods of treatment can provide for reduced side effects, e.g., undesirable side effects that are associated with activation of a beta-1 selective adrenergic receptor. The subject compounds can be highly selective activation of a target β2AR without significant undesirable activation of a β1AR. Common side effects that are shown with non-selective or less selective β2AR agonists include, but are not limited to, shakiness, headache, fast heart rate, dizziness, and feeling anxious, worsening bronchospasm, irregular heartbeat, low blood potassium levels. In some cases, β1AR activation can lead to hypertension, coronary heart disease, arrhythmias, myocardial infarction or ischemic heart diseases.

In certain embodiments, the method is an in vivo method that includes: administering to a subject in need thereof an effective amount of a subject compound that activates a β2AR to modify progression of a disease or condition of interest. In some cases, the term "treating" or "treatment" as used herein means the treating or treatment of a disease or medical condition in a patient, such as a mammal (such as a human) that includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

The methods for treatment, prevention, or amelioration of one or more symptoms of e.g., bronchoconstrictive disorders, in another embodiment, further include administering one or more of (a), (b), (c) or (d) as follows: (a) a β2-adrenoreceptor agonist; (b) a dopamine ($D_2$) receptor agonist; (c) a prophylactic therapeutic, such as a steroid; or (d) an anticholinergic agent; simultaneously with, prior to or subsequent to the composition provided herein.

The present disclosure also provides for a method of treating preterm labor in a subject in need of such treatment comprising administration of a therapeutically effective amount of a beta-2 selective adrenergic receptor agonist compound to the subject. The present disclosure further provides for a method of preventing premature labor in a subject susceptible thereto comprising administration of a labor-preventive amount of the compound to the subject. Further, the present disclosure also relates to a method of reducing the risk of premature labor in a subject at risk therefor. The present disclosure also provides for a method for stopping labor preparatory (i.e., prior) to Cesarean delivery in a subject in need of such treatment comprising administration of a therapeutically effective amount of a beta-2 selective adrenergic receptor agonist compound to the subject. Further, the present invention provides for compositions useful in the subject methods for treating pre-term labor and for stopping labor preparatory to Cesarean delivery.

The subject treated in the methods above is a pregnant female mammal, particularly a female human. The method may be employed in a pregnant female mammal who has begun to experience labor prematurely. Alternatively, the method may be employed in a pregnant female mammal with a history of premature labor, or a pregnant female whose pregnancy puts her at risk for premature labor by, for example, involving conditions that make premature labor more likely, including carrying multiple developing embryos, medical disorders such as serious cardiovascular or renal disease, severe anemia, cholestasis of pregnancy, marked hyperthyroidism and poorly controlled diabetes mellitus. Other factors known to correlate with the incidence of preterm labor include maternal age (the very young—under 20 years of age—and older women—over forty years of age—are predisposed);

social class (the incidence is higher among the socioeconomically deprived); weight (the malnourished are more often affected); height (women of short stature are prone); prior preterm labors; prior induced abortions; work habits (hard physical work increases the incidence); smoking; and certain pregnancy complications (such as hypertension, bacteriuria, and antepartum hemorrhage). Alternatively, the subject may be a pregnant female farm animal.

A subject in need of the present invention may also be identified as possessing high hormone levels of 3-alpha-diol glucuronide or dihydrotestosterone throughout pregnancy. Alternatively, the subject in need of the present invention may be identified as possessing inadequate hormone levels of progesterone throughout pregnancy. The term "preterm labor" shall mean expulsion from the uterus of a viable infant before the normal end of gestation, or more particularly, onset of labor with effacement and dilation of the cervix before the 37th week of gestation. It may or may not be associated with vaginal bleeding or rupture of the membranes. The term "Cesarean delivery" shall mean incision through the abdominal and uterine walls for delivery of a fetus.

As used herein, the terms "host", "subject", "individual" and "patient" are used interchangeably and refer to any mammal in need of such treatment according to the disclosed methods. Such mammals include, e.g., humans, ovines, bovines, equines, porcines, canines, felines, non-human primate, mice, and rats. In certain embodiments, the subject is a non-human mammal. In some embodiments, the subject is a farm animal. In other embodiments, the subject is a pet. In some embodiments, the subject is mammalian. In certain instances, the subject is human. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys).

The amount of compound administered can be determined using any convenient methods to be an amount sufficient to produce the desired effect in association with a pharmaceutically acceptable diluent, carrier or vehicle. The specifications for the unit dosage forms of the present disclosure will depend on the compound and the effect to be achieved, and the pharmacodynamics associated with the compound in the host.

In some embodiments, an effective amount of a subject compound is an amount that ranges from about 50 ng/ml to about 50 µg/ml (e.g., from about 50 ng/ml to about 40 µg/ml, from about 30 ng/ml to about 20 µg/ml, from about 50 ng/ml to about 10 µg/ml, from about 50 ng/ml to about 1 µg/ml, from about 50 ng/ml to about 800 ng/ml, from about 50 ng/ml to about 700 ng/ml, from about 50 ng/ml to about 600 ng/ml, from about 50 ng/ml to about 500 ng/ml, from about 50 ng/ml to about 400 ng/ml, from about 60 ng/ml to about 400 ng/ml, from about 70 ng/ml to about 300 ng/ml, from about 60 ng/ml to about 100 ng/ml, from about 65 ng/ml to about 85 ng/ml, from about 70 ng/ml to about 90 ng/ml, from about 200 ng/ml to about 900 ng/ml, from about 200 ng/ml to about 800 ng/ml, from about 200 ng/ml to about 700 ng/ml, from about 200 ng/ml to about 600 ng/ml, from about 200 ng/ml to about 500 ng/ml, from about 200 ng/ml to about 400 ng/ml, or from about 200 ng/ml to about 300 ng/ml).

In some embodiments, an effective amount of a subject compound is an amount that ranges from about 10 pg to about 100 mg, e.g., from about 10 pg to about 50 pg, from about 50 pg to about 150 pg, from about 150 pg to about 250 pg, from about 250 pg to about 500 pg, from about 500 pg to about 750 pg, from about 750 pg to about 1 ng, from about 1 ng to about 10 ng, from about 10 ng to about 50 ng, from about 50 ng to about 150 ng, from about 150 ng to about 250 ng, from about 250 ng to about 500 ng, from about 500 ng to about 750 ng, from about 750 ng to about 1 μg, from about 1 μg to about 10 μg, from about 10 μg to about 50 μg, from about 50 μg to about 150 μg, from about 150 μg to about 250 μg, from about 250 μg to about 500 μg, from about 500 μg to about 750 μg, from about 750 μg to about 1 mg, from about 1 mg to about 50 mg, from about 1 mg to about 100 mg, or from about 50 mg to about 100 mg. The amount can be a single dose amount or can be a total daily amount. The total daily amount can range from 10 pg to 100 mg, or can range from 100 mg to about 500 mg, or can range from 500 mg to about 1000 mg.

In some embodiments, a single dose of the subject compound is administered. In other embodiments, multiple doses of the subject compound are administered. Where multiple doses are administered over a period of time, the subject compound is administered twice daily (qid), daily (qd), every other day (qod), every third day, three times per week (tiw), or twice per week (biw) over a period of time. For example, a compound is administered qid, qd, qod, tiw, or biw over a period of from one day to about 2 years or more. For example, a compound is administered at any of the aforementioned frequencies for one week, two weeks, one month, two months, six months, one year, or two years, or more, depending on various factors. In some cases, the subject compound is a short-acting β2 agonists (SABA) and is administered accordingly, using any convenient method for SABA drugs, e.g., fenoterol. In some cases, the subject compound is a long-acting β2 agonists (LABA) and is administered accordingly, using any convenient method for LABA drugs, e.g., salmeterol.

Any of a variety of methods can be used to determine whether a treatment method is effective. Assessment of the effectiveness of the methods of treatment on the subject can include assessment of the subject before, during and/or after treatment, using any convenient methods. Aspects of the subject methods further include a step of assessing the therapeutic response of the subject to the treatment.

In some embodiments, the method includes assessing the condition of the subject, including diagnosing or assessing one or more symptoms of the subject which are associated with the disease or condition of interest being treated (e.g., as described herein). In some embodiments, the method includes obtaining a biological sample from the subject and assaying the sample, e.g., for the presence of an activity associated with the disease or condition of interest (e.g., as described herein). The sample can be a cellular sample. The assessment step(s) of the subject method can be performed at one or more times before, during and/or after administration of the subject compounds, using any convenient methods.

In some instances, the method delays occurrence of a symptom associated with the disease or condition. In certain instances, the method reduces the magnitude of a symptom associated with the disease (e.g., as described herein). The term "modify the progression" is employed to encompass both reduction in rate of progression (e.g., as manifested in the delay of the occurrence of one or more symptoms of the disease condition), as well as reversal of progression, including cure, of a disease condition (e.g., as manifested in the reduction of magnitude of one or more symptoms of the disease condition).

The above methods find use in a variety of different applications.

Combination Therapies

The subject compound can be administered to a subject alone or in combination with an additional, i.e., second, active agent. As such, in some cases, the subject method further comprises administering to the subject at least one additional compound. Any convenient agents may be utilized, including compounds useful for treating viral infections. The terms "agent," "compound," and "drug" are used interchangeably herein. For example, a subject compound can be administered alone or in conjunction with one or more other drugs, such as drugs employed in the treatment of a respiratory or bronchoconstrictive disease or condition. In some embodiments, the method further includes coadministering concomitantly or in sequence a second agent. Second active agents of interest include, but are not limited to any convenient drugs that find use against a bronchoconstrictive condition or disease, such as asthma.

Possible second agents of interest include, but are not limited to, β2-adrenoreceptor agonists such as, Albuterol ($\alpha^1$-(((1,1-dimethylethyl)amino)methyl)-4-hydroxy-1,3-benzenedimethanol); Bambuterol (dimethylcarbamic acid 5-(2-((1,1-dimethylethyl)amino)-1-hydroxyethyl)-1,3-phenylene ester); Bitolterol (4-methylbenzoic acid 4-(2-((1,1-dimethylethyl)amino)-1-hydroxy-yethyl)-1,2-phenylene ester); Broxaterol (3-bromo-α-(((1,1-dimethyle-thyl)amino)methyl)-5-isoxazolemethanol); Isoproterenol (4-(1-hydroxy-2-((1-methylethyl)amino)ethyl)-1,2-benzenediol); Trimetoquinol (1,2,3,4-tetrahydro-1-((3,4,5-trimethoxyphenyl)methyl)-6,7-isoquinolinediol); Clenbuterol (4-amino-3,5-dichloro-α-(((1,1-dimethylethyl)amino)methyl)benzenemethanol); Fenoterol (5-(1-hydroxy-2-((2-(4-hydroxyphenyl)-1-methylethyl)amino)ethyl)-1,3-benzenediol); Formoterol (2-hydroxy-5-((1RS)-1-hydroxy-2-(((1RS)-2-(p-methoxyphenyl)-1-methylethyl-)amino) ethyl)-formanilide); (R,R)-Formoterol; Desformoterol ((R,R) or (S,S)-3-amino-4-hydroxy-t-(((2-(4-methoxyphenyl)-1-methylethyl)amino)methyl)benzenemethanol); Hexoprenaline (4,4'-(1,6-hexanediyl)-bis(imino(-1-hydroxy-2,1-ethanediyl)))bis-1,2-benzenediol); Isoetharine (4-(1-hydroxy-2-((1-methylethyl)amino)butyl)-1,2-benzenediol); Isoprenaline (4-(1-hydroxy-2-((1-methylethyl)-amino)ethyl)-1,2-benzenediol-); Metaprotorenol (5-(1-hydroxy-2-((1-methylethyl)amino)ethyl)-1,3-benzene-diol); Picumeterol (4-amino-3,5-dichloro-α-(((6-(2-(2-pyridinyl) ethoxy)exyl)-amino)methyl)benzenemethanol); Pirbuterol ($\alpha^1$-(((1,1-dimethylethyl)amino)methyl)-3-hydroxy-2,6-pyridinemethanol); Procaterol (((R*,S*)-(±)-8-hydroxy-5-(1-hydroxy-2-((1-methylethyl)amino)butyl)-2(-1H)-quinolinone); Reproterol ((7-(3-((2-(3,5-dihydroxyphenyl)-2-hydroxyeth-yl)amino)-propyl)-3,7-dihydro-1,3-dimethyl-1H-purine-2,6-dione); Rimiterol (4-(hydroxy-2-piperidinylmethyl)-1,2-benzenediol); Salbutamol ((±)-$\alpha^1$-(((1,1-dimethylethyl)-amino)-methyl)-4-hydroxy-1,3-benzenedimethanol); (R)-Salbutamol; Salmeterol ((±)-4-hydroxy-$\alpha^1$-(((6-(4-phenylbutoxy)hexyl)amino)methyl)-1,3-benzenedimethanol); (R)-Salmeterol; Terbutaline (5-(2-((1,1-dimethylethyl)amino)-1-hydroxyethyl)-1,3-benzenediol); Tulobuterol (2-chloro-α-(((1,1-dimethylethyl)amino)-methyl)benzenemethanol); and TA-2005 (8-hydroxy-5-((1R)-1-hydroxy-2-(N-((1R)-2-(4-methoxyphenyl)-1-methylethyl)amino)ethyl)-carbostyril hydrochloride); Dopamine ($D_2$) receptor agonists such as Apomorphine ((r)-5,6,6a,7-tetrahydro-6-methyl-4H-dibenzo[de,g] quinoli-ne-10,11-diol); Bromocriptine ((5'α)-2-bromo-12'-hydroxy-2'-(1-methyl-lethyl)-5'-(2-methylpropyl) ergotaman-3',6',18-trione); Cabergoline ((8β)-N-(3-(dimethylamino)propyl)-N-((ethylamino)carbonyl)-6-(2-prop-enyl)ergoline-8-carboxamide); Lisuride (N'-((8a)-9, 10-didehydro-6-methylergolin-8-yl)-N,N-diethylurea); Pergolide ((8a)-8-((methylthio)methyl)-6-propylergoline); Levodopa (3-hydroxy-L-tryrosine); Pramipexole ((s)-4,5,6, 7-tetrahydro-N.sup.6-propyl-2,6-benzothiazolediamine); Quinpirole hydrochloride (trans-(−)-4aR-4,4a,5,6,7,8,8a,9-octahydro-5-pro-pyl-1H-pyrazolo[3,4-g]quinoline hydrochloride); Ropinirole (4-(2-(dipropylamino)ethyl)-1,3-dihydro-2H-indol-2-one); and Talipexole (5,6,7,8-tetrahydro-6-(2-propenyl)-4H-thiazolo[4,5-d]azepin-2-amine); and other dopamine $D_2$ receptor agonists disclosed in WO 99/36095.

The terms "co-administration" and "in combination with" include the administration of two or more therapeutic agents either simultaneously, concurrently or sequentially within no specific time limits. In one embodiment, the agents are present in the cell or in the subjects body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

"Concomitant administration" of a known therapeutic drug with a pharmaceutical composition of the present disclosure means administration of the compound and second agent at such time that both the known drug and the composition of the present invention will have a therapeutic effect. Such concomitant administration may involve concurrent (i.e. at the same time), prior, or subsequent administration of the drug with respect to the administration of a subject compound. Routes of administration of the two agents may vary, where representative routes of administration are described in greater detail below. A person of ordinary skill in the art would have no difficulty determining the appropriate timing, sequence and dosages of administration for particular drugs and the subject compound.

In some embodiments, the compounds (e.g., a subject compound and the at least one additional compound) are administered to the subject within twenty-four hours of each other, such as within 12 hours of each other, within 6 hours of each other, within 3 hours of each other, or within 1 hour of each other. In certain embodiments, the compounds are administered within 1 hour of each other. In certain embodiments, the compounds are administered substantially simultaneously. By administered substantially simultaneously is meant that the compounds are administered to the subject within about 10 minutes or less of each other, such as 5 minutes or less, or 1 minute or less of each other.

Also provided are pharmaceutical preparations of the subject compound and the second active agent. In pharmaceutical dosage forms, the compound may be administered in the form of a pharmaceutically acceptable salt, or the compound may also be used alone or in appropriate association, as well as in combination, with other pharmaceutically active compounds.

Dosage levels of the order of from about 0.01 mg to about 140 mg/kg of body weight per day are useful in representative embodiments, or alternatively about 0.5 mg to about 7 g per patient per day. Those of skill will readily appreciate that dose levels can vary as a function of the compound composition, the severity of the symptoms and the susceptibility of the subject to side effects. Dosages for a subject compound are readily determinable by those of skill in the art by a variety of means.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, such as 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

As such, unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may include the inhibitor(s) in a composition as a solution in sterile water, normal saline or another pharmaceutically acceptable carrier. The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular peptidomimetic compound employed and the effect to be achieved, and the pharmacodynamics associated with each compound in the host. Those of skill in the art will readily appreciate that dose levels can vary as a function of the specific compound, the nature of the delivery vehicle, and the like. Preferred dosages for a subject compound or agent are readily determinable by those of skill in the art by a variety of means.

Devices, Kits & Systems

Also provided are devices, kits and systems and that find use in practicing embodiments of the methods, such as those described as described above. Also provided herein are devices that are pre-loaded with the subject compositions for delivery of the subject compounds to a subject.

Any nebulizer is contemplated for use in the devices, kits and methods provided herein. In particular, the nebulizers for use herein nebulize liquid formulations, including the compositions provided herein, containing no propellant. The nebulizer may produce the nebulized mist by any method known to those of skill in the art, including, but not limited to, compressed air, ultrasonic waves, or vibration. The nebulizer may further have an internal baffle. The internal baffle, together with the housing of the nebulizer, selectively removes large droplets from the mist by impaction and allows the droplets to return to the reservoir. The line aerosol droplets thus produced are entrained into the lung by the inhaling air/oxygen.

Any inhaler (e.g., as described herein) is contemplated for use in the devices, kits and methods provided herein. In some cases, the inhaler device is a pressurized metered dose inhaler (pMDI) (e.g., as described herein). In some cases, the inhaler is a dry powder inhaler (e.g., as described herein).

An autoinjector, i.e., a hand-held medical device that injects a measured dose (e.g., 0.1-0.5 mg) of a compound using autoinjector technology (e.g., as described herein), is also contemplated for use in the devices, kits and methods provided herein. In some cases, a kit includes combinations of a compound or composition provided herein and a delivery device such as a nebulizer or syringe. The combinations can be packaged as kits, which optionally contain other components, including instructions for use of the nebulizer or syringe. The term kit can also refer to a packaged active agent or agents. The term system can refer to a collection of two or more different active agents, present in a single or disparate composition, or an active agent and a device that are brought together for the purpose of practicing the subject methods. In some embodiments, the subject system or kit includes a dose of a subject compound (e.g., as described herein) and a dose of a second active agent (e.g., as described herein) in amounts effective to treat a subject for a disease or condition of interest. Kits and systems for practicing the subject methods may include one or more pharmaceutical formulations. As such, in certain embodiments the kits may include a single pharmaceutical composition, present as one or more unit dosages, where the composition may include one or more active agents (e.g., as described herein). In some embodiments, the kit may include two or more separate pharmaceutical compositions, each containing a different active agent, at least one of which is a nucleoside compound (e.g., as described herein).

Also of interest are kits and systems finding use in the subject methods, e.g., as described above. Such kits and systems may include one or more components of the subject methods, nebulizer, syringe, etc. The various kit components may be present in the containers, e.g., sterile containers, where the components may be present in the same or different containers.

In addition to the above-mentioned components, a subject kits may further include instructions for using the components of the kit, e.g., to practice the subject method. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, Hard Disk Drive (HDD), portable flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

ADDITIONAL EMBODIMENTS

Additional embodiments are set forth in the following clauses.

Clause 1. A compound, of formula (II):

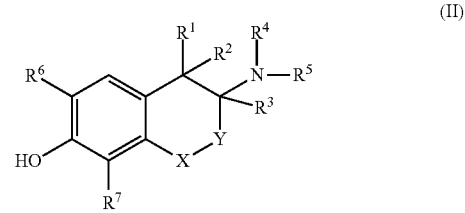

wherein:
$R^1$ and $R^2$ are independently hydrogen or hydroxyl;
$R^3$ is selected from hydrogen, alkyl and substituted alkyl;
$R^4$ and $R^5$ are independently selected from hydrogen, alkyl, substituted alkyl, aryl, substituted aryl, heteroaryl, substituted heteroaryl, heterocycle and substituted heterocycle, connected via an optional linker;
$R^6$ and $R^7$ are independently selected from hydrogen, hydroxyl, alkyl, substituted alkyl, halogen, alkoxy, substituted alkoxy, substituted amino and amino; and
X—Y is selected from —CH$_2$—, —CH$_2$CH$_2$—, —CH$_2$CH$_2$CH$_2$— and CH=CH;
that is stereoisomerically enriched in a (R,R)-trans diastereomer, or a pharmaceutically acceptable salt thereof.

Clause 2. The compound according to clause 1, wherein the compound is stereoisomerically pure (R,R)-trans diastereomer.

Clause 3. The compound according to any one of clauses 1-2, wherein:
$R^1$ is hydrogen and $R^2$ is hydroxyl;
$R^3$ is hydrogen;
$R^4$ and $R^5$ are independently selected from hydrogen, alkyl, substituted alkyl, aryl, substituted aryl, heteroaryl, substituted heteroaryl, heterocycle and substituted heterocycle;
$R^6$ is selected from hydrogen, hydroxyl, CH$_2$OH, halogen, substituted amino and amino
$R^7$ is selected from hydroxyl, CH$_2$OH, halogen, substituted amino and amino; and
X—Y is —CH$_2$CH$_2$—.

Clause 4. The compound according to any one of clauses 1-3, wherein:
$R^1$ is hydrogen and $R^2$ is hydroxyl;
$R^3$ and $R^4$ are each is hydrogen;
$R^5$ is alkyl or substituted alkyl;
$R^6$ is selected from hydrogen, hydroxyl, CH$_2$OH, halogen, substituted amino and amino
$R^7$ is selected from hydroxyl, CH$_2$OH, halogen, substituted amino and amino; and
X—Y is —CH$_2$CH$_2$—.

Clause 5. The compound according to any one of clauses 1-4, wherein $R^5$ is selected from linear lower alkyl, branched lower alkyl, cycloalkyl, substituted linear lower alkyl, substituted branched lower alkyl, substituted cycloalkyl, heterocycle and substituted heterocycle.

Clause 6. The compound according to any one of clauses 1-5, wherein $R^5$ is selected from methyl, ethyl, n-propyl, isopropyl, cyclopropyl, cyclobutyl, cyclopentyl, cyclohexyl, butyl, isobutyl, tert-butyl, and substituted versions thereof.

Clause 7. The compound according to any one of clauses 1-6, wherein $R^6$ is hydrogen.

Clause 8. The compound according to any one of clauses 1-6, wherein $R^7$ is hydroxyl.

Clause 9. The compound according to any one of clauses 1-8, wherein:

$R^1$ is hydrogen and $R^2$ is hydroxyl;

$R^3$, $R^4$ and $R^6$ are each is hydrogen;

$R^5$ is H, methyl, ethyl, isopropyl, cyclopropyl, cyclopentyl, tert-butyl, 2-fluoro-ethyl, 3-fluoro-propyl, (FCH$_2$)$_2$CH—, (CH$_3$OCH$_2$)$_2$CH—, neopentyl-, (CH$_3$)$_3$Si—CH$_2$—, oxetan-3-yl, cyclobutylmethyl, 2,2-difluoro-cyclobutylmethyl;

$R^7$ is selected from hydroxyl and CH$_2$OH; and

X—Y is —CH$_2$CH$_2$—.

Clause 10. The compound of clause 9, wherein $R^7$ is hydroxyl.

Clause 11. The compound of clause 9, wherein $R^7$ is CH$_2$OH.

Clause 12. The compound according to any one of clauses 1-11, wherein $R^5$ is hydrogen.

Clause 13. The compound according to any one of clauses 1-11, wherein $R^5$ is methyl. Clause 14. The compound according to any one of clauses 1-11, wherein $R^5$ is ethyl.

Clause 15. The compound according to any one of clauses 1-11, wherein $R^5$ is isopropyl.

Clause 16. The compound according to any one of clauses 1-11, wherein $R^5$ is tert-butyl. Clause 17. The compound according to any one of clauses 1-11, wherein $R^5$ is cyclopropyl.

Clause 18. The compound according to any one of clauses 1-11, wherein $R^5$ is cyclopentyl.

Clause 19. The compound according to any one of clauses 12-18, wherein the compound is a stereoisomerically pure (R,R)-trans diastereomer.

Clause 20. The compound of clause 19, having formula (Va):

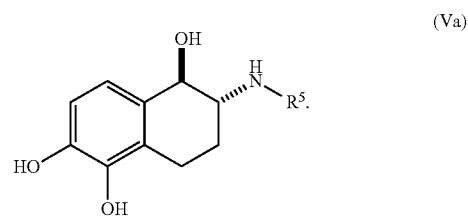

Clause 21. The compound of clause 20, wherein $R^5$ is H, alkyl or substituted alkyl. Clause 22. The compound of clause 20 or 21, wherein $R^5$ is selected from H, CH$_3$, isopropyl, cyclopentyl, 2-fluoro-ethyl, 3-fluoro-propyl, (FCH$_2$)$_2$CH—, (CH$_3$OCH$_2$)$_2$CH—, neopentyl-, (CH$_3$)$_3$Si—CH$_2$—, oxetan-3-yl, cyclobutylmethyl and 2,2-difluoro-cyclobutylmethyl. Clause 23. The compound of clause 20 or 21, wherein $R^5$ is -L-Ar, wherein L is a covalent bond or a linker, and Ar is selected from aryl, substituted aryl, heteroaryl and substituted heteroaryl.

Clause 24. The compound of clause 23, wherein Ar is phenyl or substituted phenyl.

Clause 25. The compound of clause 23 or 24, wherein the compound is selected from one of the following structures:

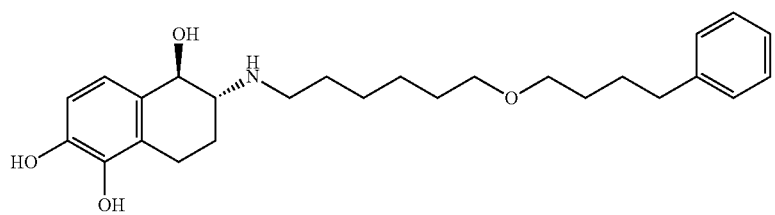

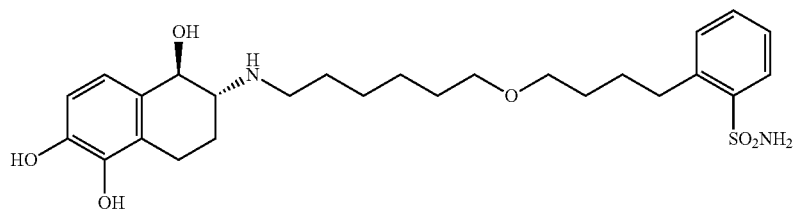

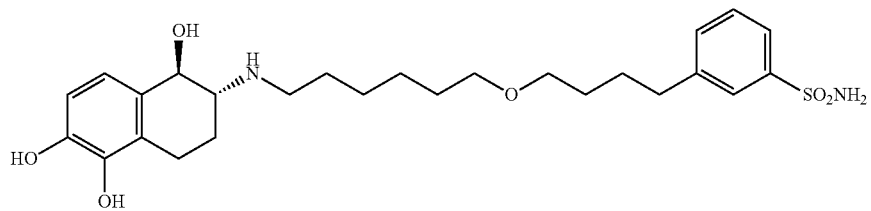

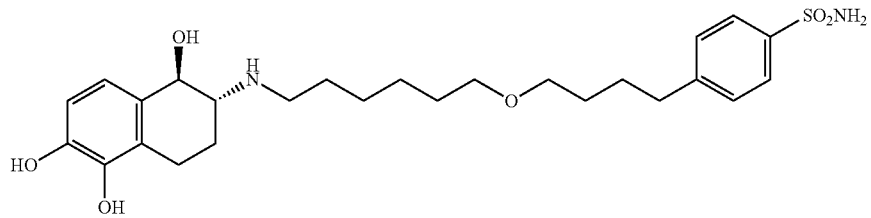

-continued
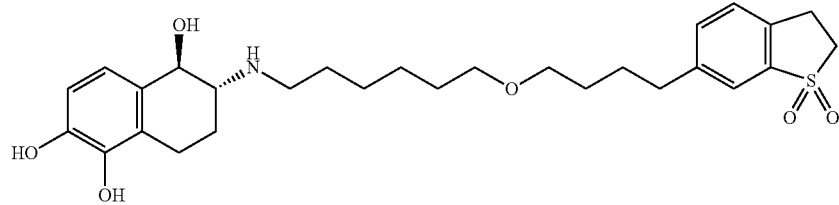
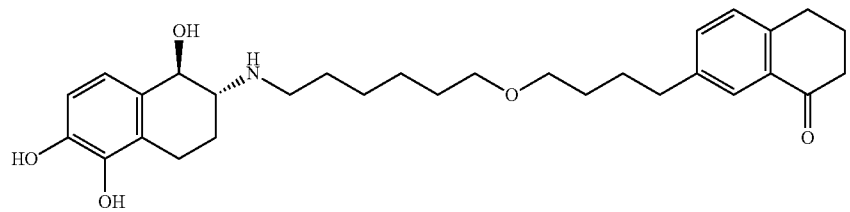
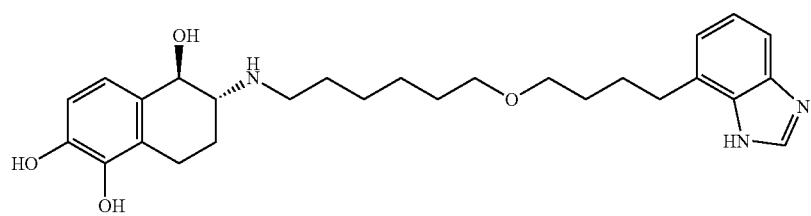
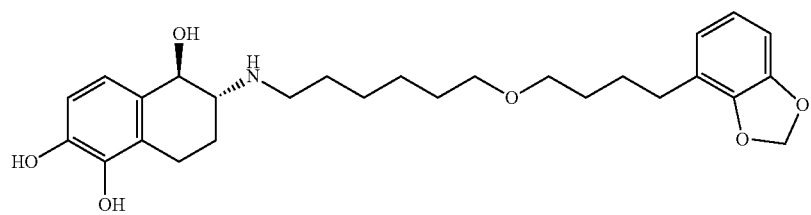
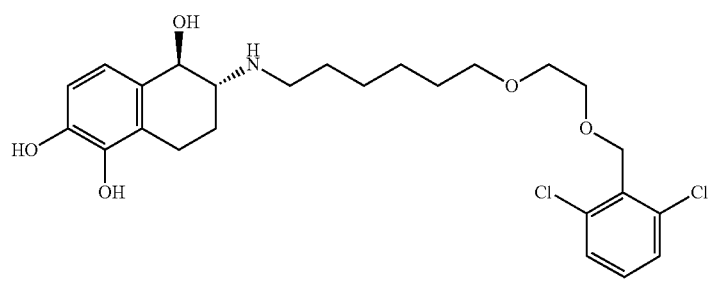
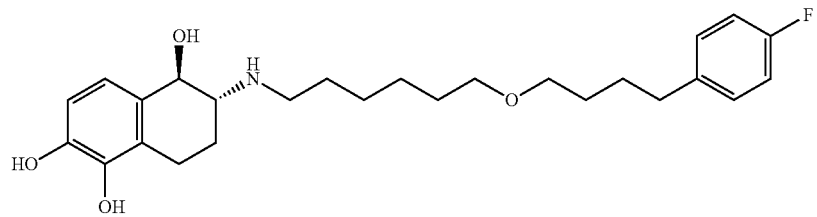
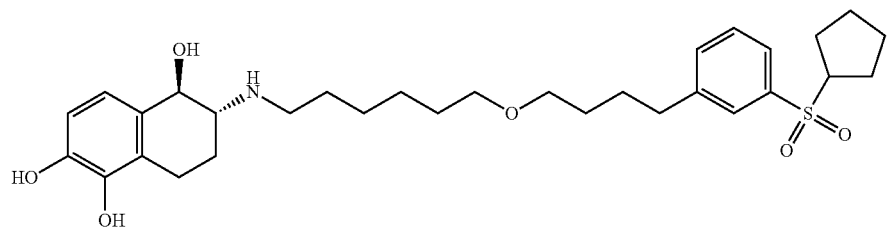

-continued

[chemical structures]

Clause 26. A pharmaceutical composition comprising:
a compound according to any one of clauses 1-25, or a pharmaceutically acceptable salt thereof; and
a pharmaceutically acceptable excipient.

Clause 27. A method of treating a bronchoconstrictive disease or condition or heart failure, the method comprising:
administering to a subject in need thereof an effective amount of a β2AR selective compound to ameliorate one or more symptoms associated with undesired and/or uncontrolled bronchoconstriction, or heart failure, in the subject.

Clause 28. The method according to clause 27, wherein the bronchoconstrictive disease or condition is bronchial asthma, exercise-induced bronchoconstriction and chronic obstructive pulmonary disease (COPD).

Clause 29. The method according to clause 28, wherein the disease or condition is an asthma attack.

Clause 30. The method according to any one of clauses 27-29, wherein the administering is performed via a nebulizer or an inhaler.

Clause 31. The method according to any one of clauses 27-29, wherein the administering is performed via injection, e.g., via an autoinjector.

Clause 32. The method according to any one of clauses 27-30, wherein the β2AR selective compound is a compound according to any one of clauses 1-25 or a pharmaceutical composition according to clause 26.

Clause 33. The method according to clause 32, wherein the administering includes administering a compound that is a stereoisomerically pure (R,R)-trans stereoisomer.

Clause 34. A method of selectively activating a β2AR in a cell, the method comprising:
contacting a cell comprising a β2AR with an effective amount of β2AR selective compound to selectively activate the β2AR in the cell.

Clause 35. The method according to clause 34, wherein the β2AR selective compound has 100-fold or greater selectivity for β2AR over β1AR.

Clause 36. The method according to clause 35, wherein the β2AR selective compound has 300-fold or greater selectivity for β2AR over β1AR.

Clause 37. The method according to clause 36, wherein the β2AR selective compound has 1000-fold or greater selectivity for β2AR over β1AR.

Clause 38. The method according to any one of clauses 34-37, wherein β2AR selective compound activates recruitment of β-arrestin recruitment over G protein-promoted signaling from the β2AR.

Clause 39. The method according to any one of clauses 34-38, wherein the β2AR selective compound is a compound according to any one of clauses 1-25.

Clause 40. The method according to clause 39, wherein the β2AR selective is a compound that is a stereoisomerically pure (R,R)-trans stereoisomer.

Clause 41. A delivery device that contains a composition comprising the compound according to any one of clauses 1-25.

Clause 42. The device of clause 41, wherein the device is an inhaler.

Clause 43. The device of clause 42, wherein the inhaler is a multidose inhaler or a dry powder inhaler.

Clause 44. The device of clause 41 or 42, wherein the inhaler is pre-loaded with a dry powder composition comprising the compound according to any one of clauses 1-19.

Clause 45. The device of clause 35, wherein the device is a nebulizer.

Clause 46. A method of treating pre-term labor, administering to a subject in need thereof an effective amount of a β2AR selective compound to ameliorate one or more symptoms associated with pre-term labor in the subject (e.g., uterine contractions).

Clause 47. The method according to clause 40, wherein the administering is performed via nebulizer or inhaler.

Clause 48. The method according to any one of clauses 46-47, wherein the administering is performed via injection.

Clause 49. The method according to any one of clauses 46-47, wherein the β2AR selective compound is a compound according to any one of clauses 1-25 or a pharmaceutical composition according to clause 26.

Clause 50. The method according to clause 49, wherein the administering includes administering a compound that is a stereoisomerically pure (R,R)-trans stereoisomer.

Clause 51. An autoinjector that contains a composition comprising the compound according to any one of clauses 1-25.

Clause 52. The autoinjector of clause 51, containing a single dose of the compound.

Clause 53. The autoinjector of clause 51, configured to inject a measured dose (e.g., 0.1-0.5 mg) of the compound into a subject when an injection mechanism is activated.

The following examples are offered by way of illustration and not by way of limitation.

EXAMPLES

Example 1: Design and Synthesis of Compounds

Introduction

The loss of a ligand's entropy upon receptor binding can be reduced by rigidization of its chemical structure. Thus, conformational restriction of receptor ligands confers an increase of potency, if the rigid ligand matches the bioactive conformation of the parent compound and the restricting chemical units do not cause repulsive interactions with the receptor. Conformational restriction may also induce selectivity for receptor subtypes or individual functional states of the target protein, because slightly different shapes of binding pockets may require an adaption of the ligand's conformation. Thus, conformational restriction of specific ligands is an effective means to generate subtype selectivity and signaling bias.

Targeting the pharmacologically important target $\beta_2$-AR, synthetically constrained receptor agonists we designed and prepared of the catecholamine type (isoprenaline, adrenaline, noradrenaline) into a bioactive conformation. A set of eight different isomers of ethylene bridged catecholamines was prepared. Whereas seven regio- and stereoisomers were more or less inactive, one isomer possesses superior $\beta_2$-AR binding affinity and potency. Most interestingly, exemplary compounds of interest "super-iso", "super-norepi" and especially "super-epi" exhibit high selectivity for $\beta_2$-AR over pi-AR (see Table 1 and 2), pointing towards distinct bioactive conformations of the endogenous agonists at the two highly homologous adrenoceptor subtypes. Moreover, the active compounds show significant bias for β-arrestin recruitment over G protein-promoted signaling. Structural insights into the receptor state and the binding poses of super-epi and super-iso are obtained by co-crystal structures of $\beta_2$-AR bound to exemplary compound Nb6B9.

General Synthesis Methods

Title compounds of the general formula 2 can be accessed following synthesis scheme 1. Detailed procedures and analytical data are provided below in the examples section.

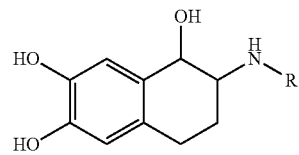

Title compounds of the general formula 3 can be accessed following synthesis scheme 2. Detailed procedures and analytical data are provided below in the examples section.

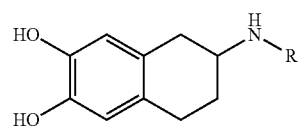

Title compounds of the general formula 4 can be accessed following synthesis scheme 3. Detailed procedures and analytical data are provided below in the examples section.

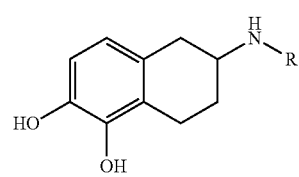

Title compounds of the general formula 4 can be accessed by adapting the synthesis scheme described herein.

Synthesis Scheme 1: Preparation of title compounds of the general formula 2.

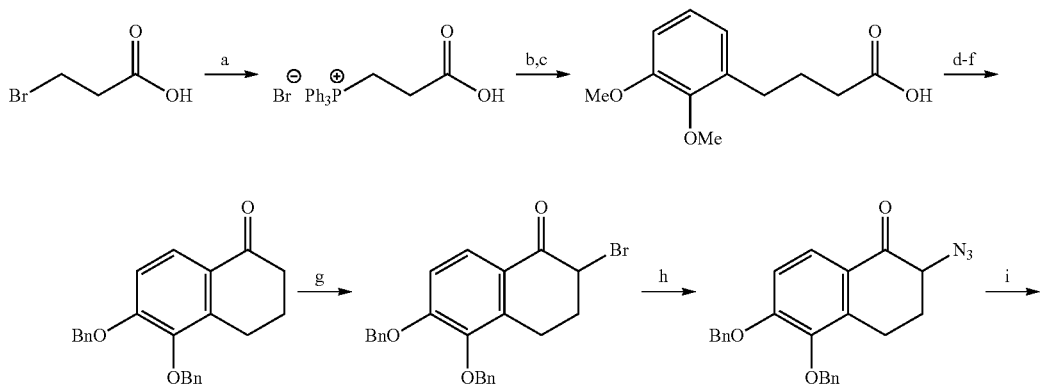

51

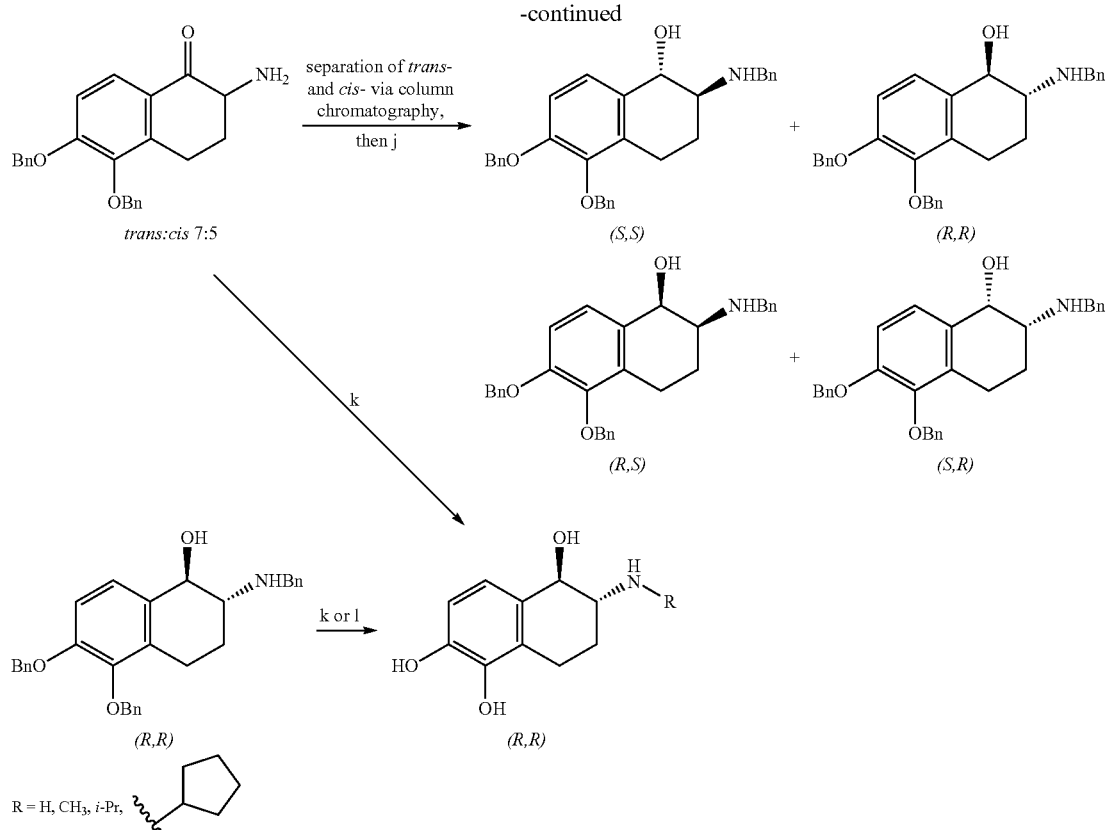

R = H, CH₃, i-Pr, [cyclopentylmethyl]

Reagents and conditions:
a) PPh₃, CH₃CN, reflux;
b) 2,3-dimethoxybenzaldehyde, KOtBu, CH₂Cl₂, 0° C. to r.t.;
c) 10% Pd/C, H₂, EtOH, r.t.;
d) PPA, 60° C., 30 min
e) AlCl₃, toluene, reflux;
f) BnBr, NaI, acetone, reflux, 16 h;
g) 1. Br₂, Et₂O, r.t.;
   2. HPO(OEt)₂, NEt₃, THF, r.t.
h) NaN₃, AcOH, DMF, 0° C.;
i) LiAlH₄, 1,2-DCE, r.t.;
j) PhCHO, NaBH(OAc)₃, 1,2-DCE, r.t.;
k) 1. CH₂O, acetone or pentanone, NaBH(OAc)₃, 1,2-DCE, r.t. and preparatve chiral separation;
   2. 10% Pd/C, H₂, EtOH, r.t.
l) 10% Pd/C, H₂, EtOH, r.t.

Sythesis Scheme 2.
Preparation of title compounds of the general formula 3.

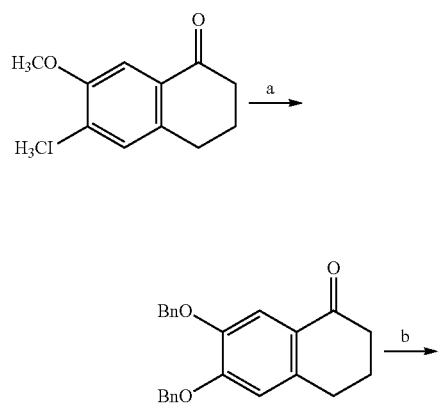

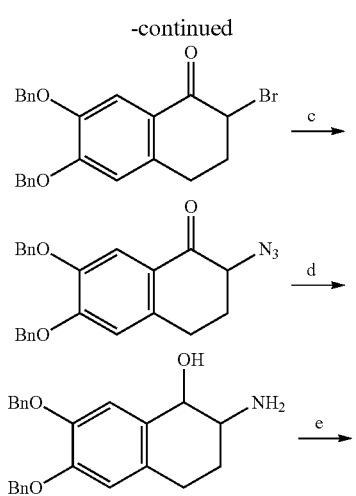

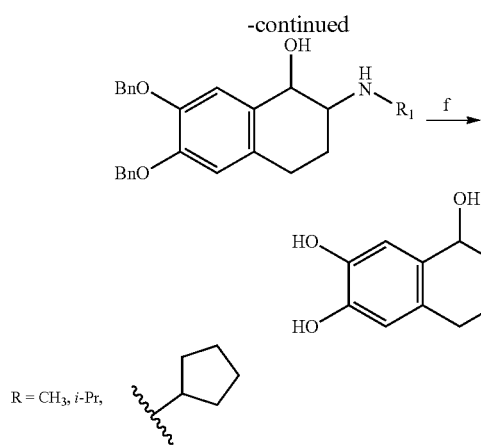

R = CH₃, i-Pr, [cyclopentyl]

Reagents and conditions:
a) 1. toluene, N₂, AlCl₃, reflux;
   2. Acetone, BnBr, K₂CO₃, reflux;
b) 1. Br₂, Et₂O, r.t.;
   2. HPO(OEt)₂, NEt₃, THF, r.t.
c) NaN₃, AcOH, DMF, 0° C.;
d) LiAlH₄, 1,2- DCE, r.t.;
e) 1. CH₂O, acetone or pentaone, NaBH(OAc)₃, 1,2-DCE, r.t. and preparative chiral separation
f) 10% Pd/C, H₂, EtOH, r.t.

Synthesis Scheme 3
Preparation of title componds of the general formula 4.

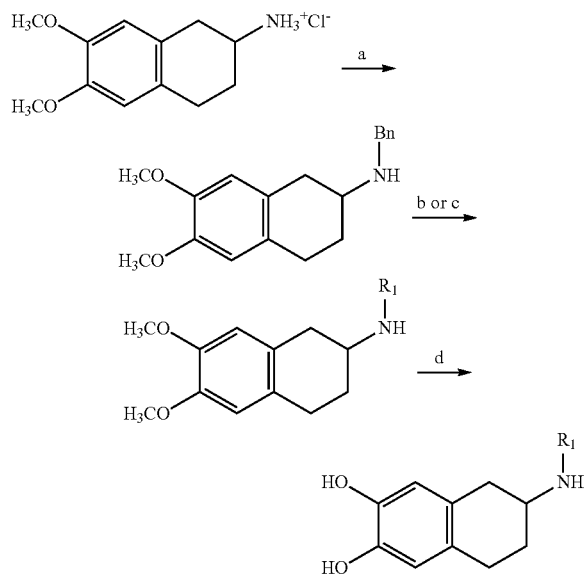

R = H, CH₃
Reagents and conditions:
a) PhCHO, NaBH(OAc)₃, 1,2-DCE, r.t.;
b) 1. Chiral preparative HPLC,
   2. 10% Pd/C, H₂, MeOH, r.t;
c) 1. CH₂O, NaBH(OAc)₃, 1,2-DCE, r.t.;
   2. 10% Pd/C, H₂, MeOH, r.t;
d) BBr₃, CH₂Cl₂, r.t.

The synthesis of exemplary compounds can be performed starting with chemical precursors, which are commercially available from common suppliers of fine chemicals, by name ACROS (via suppliers for fine chemicals like Fisher Scientific, Nidderau, Germany or VWR International, Darmstadt, Germany), Alfa Aeser (Karlsruhe, Germany), Activate Scientific (Rien, Germany), Sigma Aldrich (via Merck, Darmstadt, Germany), TCI Deutschland (Eschborn, Germany). All example compounds have been synthesized according to general procedures as described below:

General Procedure 1: Reductive Amination:

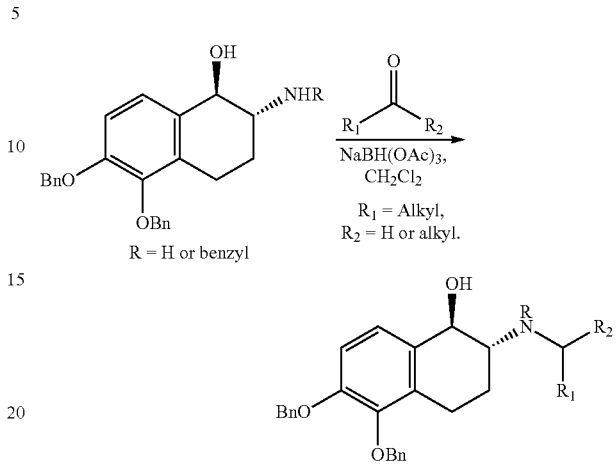

To a solution of enantiopure primary amine or secondary benzylamine (1 eq.) in anhydrous CH₂Cl₂ is added aldehyde/ketone (1-10 eq.) and the resulting solution stirred for 5 minutes. After addition of NaBH(OAc)₃ (3 eq.), the suspension is strongly stirred under inert gas atmosphere for 5 h. The mixture is then quenched with sat. NaHCO₃ solution and extracted thrice with CH₂Cl₂. The pooled organic layers are washed with brine, dried (MgSO₄) and rotary evaporated. The crude residue is either obtained in relatively pure form already or purified by silica flash chromatography using CH₂Cl₂/MeOH as eluent system.

General Procedure 2: Amide Coupling:

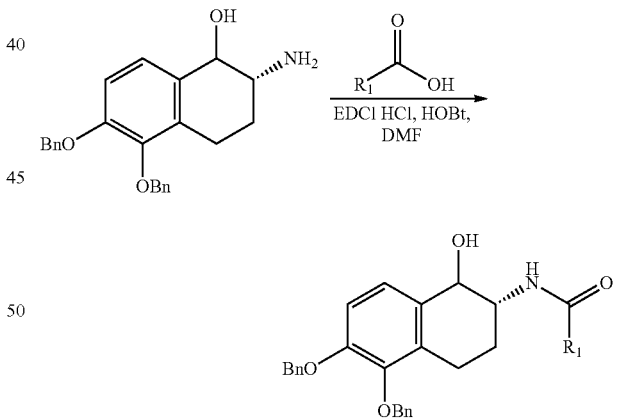

A mixture of enantiopure (R,R)-trans-aminoalcohol (1 eq.), carboxylic acid (0.9 eq.), 1-ethyl-3-(3-dimethylaminopropyl)carbodiimide (EDCI) HCl salt (1.25 eq.) and 1-hydroxybenzotriazole (HOBt) hydrate (1.25 eq.) in anhydrous DMF is stirred at room temperature for 5 h. After diluting with excess water and ethyl acetate, the organic layer is washed 2× with water, 1× with 0.1% acetic acid, 1× with sat. NaHCO₃ and brine. After drying over MgSO₄, the solvent is rotary evaporated and the crude carboxamide purified by flash chromatography on silica (isohexane/acetone or dichloromethane/MeOH).

General Procedure 3: Reduction of Carbonyl Amide Compounds:

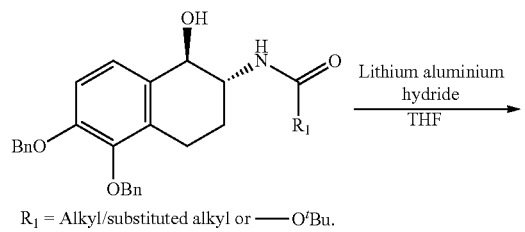

R₁ = Alkyl/substituted alkyl or ⎯⎯ OᵗBu.

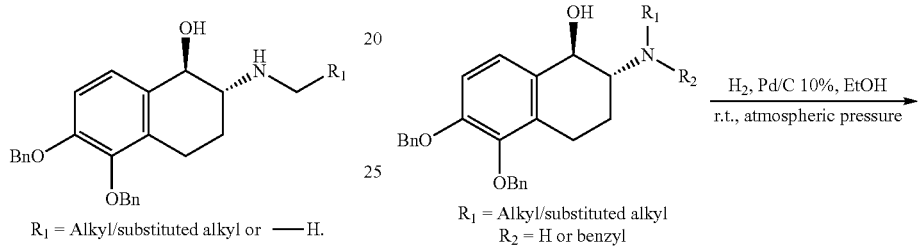

R₁ = Alkyl/substituted alkyl or ⎯⎯ H.

To a solution of (R,R)-trans-carbonyl compound (1 eq.) in anhydrous THF is carefully added 4 M lithium aluminium hydride (LAH) in Et₂O (3 eq.) and the mixture thereafter stirred at 60° C. in a sealed vial for 2 h. After quenching residual hydride with ice and extraction with CH₂Cl₂, the organic layers are pooled, washed with brine, dried (MgSO₄) and rotary evaporated. The crude product is purified by silica flash chromatography (CH₂Cl₂/MeOH).

General Procedure 4: N-Alkylation Reactions:

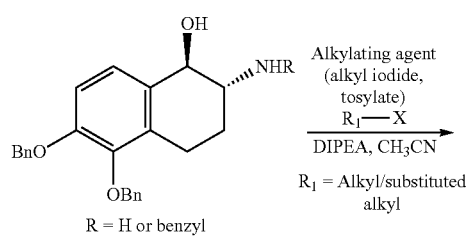

R = H or benzyl
R₁ = Alkyl/substituted alkyl

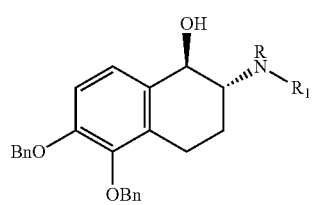

To a solution of enantiopure primary amine or secondary benzylamine (1 eq.) in acetonitrile is added Hünig's base (DIPEA, 1-2 eq.) and the desired alkylating agent (1-5 eq.). The mixture is heated to reflux in a sealed vial for 3 days. After diluting with water and CH₂Cl₂, the aqueous layer is extracted twice with CH₂Cl₂, the organic extracts pooled, washed with brine and dried with MgSO₄. The residue obtained by rotary evaporation is purified by silica gel chromatography (CH₂Cl₂/MeOH). Preparative HPLC can be used to obtain a pure product.

General Procedure 5: Protecting Group Removal:

Cleavage of benzyl ethers is accomplished by stirring a suspension of Bn-protected precursor (1 eq.) and Pd/C 10% (10 weight-%) in EtOH under H₂ atmosphere and light protection for 2 h. Then, the suspension is filtered through a syringe filter into excess of a precooled solution of 0.1% TFA in degassed water. The mixture is directly frozen, lyophilized and purified by prep. HPLC, if necessary. The catecholamines are therefore obtained as their trifluoroacetic acid (TFA) salts, that are handled under air- and light-avoiding conditions.

Example 2

Biological Activity of Compounds of Interest

The binding affinities of exemplary compounds of interest at β1AR and β2AR were evaluated in a binding assay.

TABLE 1

Binding affinities of the compounds towards α1, α2, β1 and β2 adrenoceptors.

| compound | R₁ | R₂ | R₃ | R₄ | Stereo-chemistry | β1-AR [³H]CGP12177 Kᵢ [nM] | β2-AR [³H]CGP12177 Kᵢ [nM] | α1A-AR [³H]prazosin Kᵢ [nM] | α2A-AR [³H]RX821002 Kᵢ [nM] |
|---|---|---|---|---|---|---|---|---|---|
| AS424A | H | OH | OH | i-Pr | (R,R)-trans | 2,100 | 32 | 60,000 | 71,000 |
| JS 3-97 | H | OH | OH | i-Pr | (S,S)-trans | >50,000 | 370 | | |
| AS424B | H | OH | OH | i-Pr | (R,S)-cis | 24,000 | 450 | | |
| JS 3-99 | H | OH | OH | i-Pr | (S,R)-cis | 49,000 | 1,900 | | |
| JS 3-89 | OH | H | OH | i-Pr | trans | >50,000 | >50,000 | | |
| JS 3-71 | OH | H | OH | i-Pr | cis | >50,000 | >50,000 | | |
| AS443 | H | OH | OH | CH₃ | (R,R)-trans | 38,000 | 140 | 17,000 | 13,000 |
| AS446 | H | OH | OH | H | (R,R)-trans | 16,000 | 680 | 18,000 | 15,000 |
| JS 3-51 | H | OH | OH | cyclopentyl | (S,S)-trans | 27,000 | 240 | | |
| JS 3-159 | H | OH | OH | cyclopentyl | (R,R)-trans | 7,100 | 25 | | |
| JS 3-65 | H | OH | OH | cyclopentyl | (S,R)-cis | >50,000 | 2,500 | | |
| JS 3-55 | H | OH | OH | cyclopentyl | (R,S)-cis | >50,000 | >20,000 | | |
| AS LM15 | OH | H | H | H | (S)-isomer | 31,000 | 20,000 | | |
| AS LM16 | OH | H | H | H | (R)-isomer | 83,000 | 76,000 | | |
| AS LM31 | OH | H | H | CH₃ | racemic mixture | 44,000 | 80,000 | | |
| AS LM33 | H | OH | H | CH₃ | racemic mixture | 90,000 | 46,000 | | |
| AS LM27 | H | OH | H | H | (−)-isomer | 46,000 | 7,600 | | |
| AS LM28 | H | OH | H | H | (+)-isomer | >100,000 | 29,000 | | |
| LM 75 | H | OH | OH | 3-F-propyl | (R,R)-trans | 7,500 | 97 | 23,000 | 18,000 |
| LM 80 | H | OH | OH | 2-F-ethyl | (R,R)-trans | 7,000 | 280 | >90,000 | 30,000 |
| LM 103 | H | OH | OH | (FCH₂)₂CH— | (R,R)-trans | 10,000 | 630 | >100,000 | 53,000 |
| LM 114 | H | OH | OH | (CH₃OCH₂)₂CH— | (R,R)-trans | 40,000-80,000 | 600-1,500 | 10,000-20,000 | 6,000-12,000 |
| LM 117 | H | OH | OH | neopentyl- | (R,R)-trans | 50,000->100,000 | 250-700 | 10,000-20,000 | 15,000-30,000 |
| LM 118 | H | OH | OH | (CH₃)₃Si—CH₂— | (R,R)-trans | 50,000->100,000 | 200-500 | 5,000-10,000 | 8,000-15000 |
| LM 113 | H | OH | OH | Oxetan-3-yl | (R,R)-trans | 50,000->100,000 | 600-1,500 | 60,000->100,000 | 25,000-45,000 |
| LM 110 | H | OH | OH | cyclobutylmethyl | (R,R)-trans | 51,000 | 170 | 4,000 | 9,900 |
| LM 112 | H | OH | OH | 2,2-difluoro-cyclobutylmethyl | (R,R)-trans | 5,000-12,000 | 25-70 | 5,000-8,000 | 8,000-15,000 |

Kᵢ values displayed in a range of nM are derived from screening experiments with a low number of repeats
The functional activity of exemplary compounds of interest in activating β1AR and β2AR were evaluated in an assay of β-arrestin-2 recruitment.

TABLE 2

Intrinsic activities of exemplary compounds for β-arrestin-2 recruitment at β1 and β2 adrenoceptors.

| compound | R₁ | R₂ | R₃ | R₄ | stereo-chemistry | β₁-AR EC₅₀ [nM] | β₁-AR E$_{max}$ [% norepinephrine] | β₂-AR EC₅₀ [nM] | β₂-AR E$_{max}$ [% norepinephrine] |
|---|---|---|---|---|---|---|---|---|---|
| noradrenaline | — | — | — | — | — | 160 | 100 | 7,200 | 100 |
| AS424A | H | OH | OH | i-Pr | (R,R)-trans | 1,200 | 82 | 24 | 103 |
| AS443 | H | OH | OH | CH3 | (R,R)-trans | 38,000 | 60 | 26 | 112 |
| AS446 | H | OH | OH | H | (R,R)-trans | 18,000 | 56 | 100 | 107 |
| JS 3-99 | H | OH | OH | i-Pr | (S,R)-cis | | | 1,200 | 100 |
| JS 3-87-2 | H | OH | OH | i-Pr | (R,S)-cis | | | 350 | 91 |

TABLE 2-continued

Intrinsic activities of exemplary compounds for β-arrestin-2 recruitment at β1 and β2 adrenoceptors.

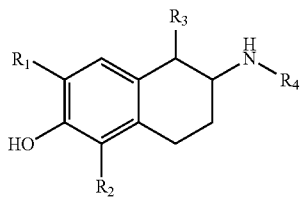

| compound | R₁ | R₂ | R₃ | R₄ | stereo-chemistry | β₁-AR EC₅₀ [nM] | β₁-AR E_max [% norepinephrine] | β₂-AR EC₅₀ [nM] | β₂-AR E_max [% norepinephrine] |
|---|---|---|---|---|---|---|---|---|---|
| JS 3-51 | H | OH | OH | cyclopentyl | (S,S)-trans | | | 120 | 93 |
| JS 3-159 | H | OH | OH | cyclopentyl | (R,R)-trans | | | 18 | 97 |
| AS LM15 | OH | H | H | H | (S)-isomer | n.d. | <5 | n.d. | <5 |
| AS LM16 | OH | H | H | H | (R)-isomer | n.d. | <5 | n.d. | <5 |
| AS LM31 | OH | H | H | CH₃ | racemic mixture | n.d. | <5 | 12,000 | 22 |
| AS LM33 | H | OH | H | CH₃ | racemic mixture | n.d. | <10 | 2,100 | 125 |
| AS LM27 | H | OH | H | H | (−)-isomer | n.d. | <5 | 2,100 | 84 |
| AS LM28 | H | OH | H | H | (+)-isomer | n.d. | <10 | 11,000 | 77 |
| LM 75 | H | OH | OH | 3-F-propyl | (R,R)-trans | 10,000 | 90 | 25 | 111 |
| LM 80 | H | OH | OH | 2-F-ethyl | (R,R)-trans | 3,000 | 81 | 66 | 110 |
| LM 103 | H | OH | OH | (FCH₂)₂CH— | (R,R)-trans | 12,000 | 18 | 640 | 109 |
| LM 114 | H | OH | OH | (CH₃OCH₂)₂CH— | (R,R)-trans | 30,000-60,000 | 35 | 500-1000 | 125 |
| LM 117 | H | OH | OH | neopentyl- | (R,R)-trans | 10,000-20,000 | 17 | 50-120 | 116 |
| LM 118 | H | OH | OH | (CH₃)₃Si—CH₂— | (R,R)-trans | 25,000-70,000 | 40 | 120-250 | 119 |
| LM 113 | H | OH | OH | Oxetan-3-yl | (R,R)-trans | >100,000 | 20 | 200-400 | 115 |
| LM 110 | H | OH | OH | cyclobutylmethyl | (R,R)-trans | 22,000 | 25 | 79 | 116 |
| LM 112 | H | OH | OH | 2,2-difluoro-cyclobutylmethyl | (R,R)-trans | 6,000-14,000 | 45 | 10-20 | 124 | n.d.: could not be determined because of lack of activity
EC50 values displayed in a range of nM are derived from screening experiments with a low number of repeats.
β-Arrestin recruitment assay Compounds can be evaluated in a β-Arrestin recruitment assay. FIG. 1A-1B shows representative dose-response curves of epinephrine (FIG. 1A) and exemplary compound AS 443 (FIG. 1B) determined by an arrestin recruitment assay expressing the subtype selectivity of exemplary compounds.

Example 3: Synthesis of Exemplary Compounds

Methods and Materials

All chemicals and solvents were purchased from Sigma Aldrich, Acros, Alfa Aesar, or Activate Scientific and were used without additional purification. Anhydrous solvents were of the highest commercially available grade and were stored over molecular sieves under a nitrogen atmosphere. Flash chromatography was performed on Merck silica gel 60 (40-63 μm) as stationary phase under positive pressure of dry nitrogen gas. TLC analyses were performed using Merck 60 F254 aluminum plates in combination with UV detection (254 nm). HR-MS was run on an AB Sciex Triple TOF660 SCiex, source type ESI, or on a Bruker maXis MS in the laboratory of the Chair of Organic Chemistry, Friedrich Alexander University Erlangen-Nuernberg, or on a Bruker maXis MS in the laboratory of the Chair of Bioinorganic Chemistry, Friedrich Alexander University Erlangen-Nuernberg. Mass detection was conducted with a Bruker Esquire 2000 ion trap mass spectrometer using APCI or ESI ionization source or with Bruker amaZon SL mass spectrometer in combination with a Agilent 1100 or Dionex Ultimate 3000 UHPLC system; respectively. Analytical HPLC was conducted on an Agilent 1200 HPLC system employing a DAD detector and a ZORBAX ECLIPSE XDB-C8 (4.6×150 mm, 5 μm) column with the following binary solvent systems: System 1: eluent, methanol/0.1% aq. formic acid, 10% methanol for 3 min, to 100% in 15 min, 100% for 6 min, to 10% in 3 min, then 10% for 3 min, flow rate 0.5 mL/min, λ=210 or 254 nm; System 2: CH₃CN/0.1% aq. formic acid, 10% CH₃CN for 3 min, to 100% in 15 min, 100% for 6 min, to 10% in 3 min, then 10% for 3 min, flow rate 0.5 mL/min, λ=210 or 254 nm. Chiral analytical HPLC was conducted on an Agilent 1200 HPLC system employing a DAD detector and a Daicel ICOOCE-SK041 (4.6×250 mm, 5 μm, flow rate 0.7 mL/min) column with the solvent systems as indicated. Preparative HPLC was performed on an Agilent 1100 Preparative Series, using a ZORBAX ECLIPSE XDB-C8 PrepHT (21.5×150 mm, 5 μm, flow rate 10 mL/min) column with the solvent systems as indicated. Chiral preparative HPLC was performed on a Daicel ICOOCG-PJ002 Semi-Prep (10 mm×250 mm, 5 μm, flow rate 7 mL/min) column with the solvent systems indicated. ¹H, and ¹³C spectra were recorded on a Bruker Avance 360, Avance 400 or a Bruker Avance 600 FT-NMR-Spectrometer. Chemical shifts were calculated as ppm relative to TMS (¹H) or solvent signal (¹³C) as internal standards.

Purification and Analytical Characterization

Intermediates and target compounds were mostly purified by chromatographic methods, usually by applying silica flash chromatography or preparative HPLC using chromatographic systems—mainly reversed phase columns—as described in the experimental section. The following columns were used:
Column 1: ZORBAX ECLIPSE 300SB-C18 PrepHT (150× 21.5 mm, 7 μm, 8-12 mL/min)

Column 2: ChiralPak IC (250×30 mm, 5 μm, 35 mL/min) for enantiomer separation.

The analytical characterization of the intermediates and final target molecules was performed by ¹H-NMR at 400 MHz or 600 MHz, ¹³C-NMR (usually DEPTQ experiments) at 150 MHz or 100 MHz and ¹⁹F-NMR at 565 MHz. Determination of chemical shifts was done in relation to the TMS signal or—if the former was not possible- to the solvent used. Additional analytics was done by mass spectrometry (ESI-MS) and by analytical HPLC applying two different chromatographic systems—being suitable for the polar target compounds—which are described below (system A, B).

System A: Water+0.3% trifluoroacetic acid and acetonitrile, 0.5 mL/min: 4% ACN→40% ACN in 26 min→25% ACN after 30 min→4% ACN after 36 min.

System B: Water+0.3% trifluoroacetic acid and methanol, 0.5 mL/min: 5% MeOH→50% MeOH in 26 min→30% MeOH after 30 min→5% MeOH after 36 min.

Synthesis of Embodiments and the Appropriate Precursors

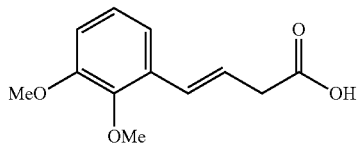 [SMILES: COc1cccc(/C=C/CC(=O)O)c1OC]

3-Bromopropanoic acid (25.4 g, 166 mmol) and triphenylphosphine (45.7 g, 174 mmol) were suspended in acetonitrile (125 mL) and were stirred at reflux for 5 h. After stirring for additional 12 h at room temperature, diethylether (200 mL) was added and the mixture was kept at −18° C. for 2 h. The formed precipitate was collected by suction filtration, washed with diethylether and dried in vacuo to obtain (2-carboxyethyl)triphenylphosphonium bromide (54.2 g, 79%) as a colorless powder. ¹H NMR (600 MHz, DMSO-d₆) δ 12.73 (br s, 1H), 7.94-7.88 (m, 3H), 7.87-7.81 (m, 6H), 7.81-7.73 (m, 6H), 3.87-3.78 (m, 2H), 2.62-2.55 (m, 2H).

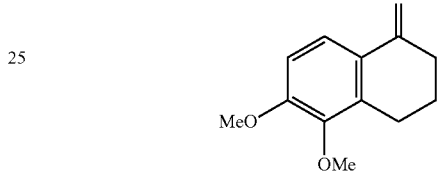

To a suspension of 2-carboxyethyl)triphenylphosphonium bromide (54.0 g, 130 mmol) in CH₂Cl₂ (160 mL) was added 2,3-dimethoxybenzaldehyde (18.0 g, 108 mmol) at 0° C. After portion wise addition of tert-BuOK (30.3 g, 270 mmol), the reaction mixture was stirred for 12 h at room temperature. It was quenched with water (240 mL), washed with CH₂Cl₂ and adjusted to pH 1. After extraction with diethylether (3×) the combined organic layers were washed with brine, dried (MgSO₄) and the solvent was rotary evaporated. The crude material was purified by silica gel chromatography (n-hexane/ethyl acetate, 3:1 v/v) to obtain (E)-4-(2,3-Dimethoxyphenyl)but-3-enoic acid (14.5 g, 60%) as a colorless solid; ¹H NMR (360 MHz, CDCl₃) δ 7.10 (dd, J=7.9, 1.4 Hz, 1H), 7.00 (t, J=8.0 Hz, 1H), 6.87-6.79 (m, 2H), 6.31 (dt, J=16.0, 7.2 Hz, 1H), 3.86 (s, 3H), 3.81 (s, 3H), 3.33 (dd, J=7.2, 1.4 Hz, 2H); ¹³C NMR (150 MHz, CDCl₃) δ 177.7, 153.1, 146.7, 131.0, 128.4, 124.2, 122.4, 118.3, 111.6, 61.1, 55.9, 38.5; LC/ESI-MS (m/z): 245.0 [M+Na]⁺.

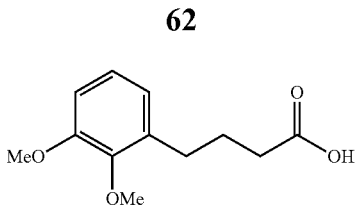

10% Pd/C (10 wt %) was added to a solution of (E)-4-(2,3-dimethoxyphenyl)but-3-enoic acid (8.32 g, 37.4 mmol) in ethanol (60 mL) and stirred under H₂ atmosphere for 4 h. After filtration through a pad of Celite, the filter cake was rinsed with ethanol and the solvent of the filtrate was removed to obtain 4-(2,3-dimethoxyphenyl)butanoic acid (8.38 g, quant.) as a colorless solid; ¹H NMR (600 MHz, CDCl₃) δ 6.99 (t, J=7.9 Hz, 1H), 6.81-6.77 (m, 2H), 3.87 (s, 3H), 3.83 (s, 3H), 2.74-2.68 (m, 2H), 2.40 (t, J=7.5 Hz, 2H), 2.00-1.90 (m, 2H); ¹³C NMR (150 MHz, CDCl₃) δ 180.0, 152.9, 147.3, 135.2, 124.0, 122.1, 110.6, 60.7, 55.8, 33.6, 29.2, 25.6; LC/ESI-MS (m/z): 247.0 [M+Na]⁺.

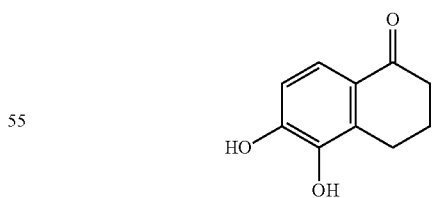

Polyphosphoric acid (170 g) was heated to 60° C. for 30 minutes and under mechanically stirring 4-(2,3-dimethoxyphenyl)butanoic acid (12.0 g, 53.5 mmol) was added portion wise over a period of 15 min. After stirring 30 minutes at 60° C. the reaction mixture was allowed to cool to room temperature and was carefully quenched with water (400 mL) under ice cooling causing a white precipitate, which was extracted with ethyl acetate (3×150 mL). The combined organic extracts were washed with brine, dried (MgSO₄) and the solvent was rotary evaporated. The crude material was recrystallized from n-hexane/ethanol to give 5,6-dimethoxy-3,4-dihydronaphthalen-1(2H)-one (10.3 g, 93%) as a light beige solid. ¹H NMR (360 MHz, CDCl₃) δ 7.85 (d, J=8.7 Hz, 1H), 6.87 (d, J=8.7 Hz, 1H), 3.92 (s, 3H), 3.81 (s, 3H), 2.95 (t, J=6.1 Hz, 2H), 2.58 (dd, J=7.2, 5.9 Hz, 2H), 2.15-2.04 (m, 2H); ¹³C NMR (151 MHz, CDCl₃) δ 197.6, 157.0, 145.5, 138.8, 126.8, 124.6, 110.2, 60.4, 55.9, 38.8, 23.4, 22.9; LC/ESI-MS (m/z): 207.0 [M+H]⁺.

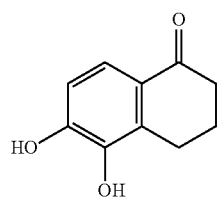 [SMILES: O=C1CCCc2c1ccc(O)c2O]

A solution of 5,6-dimethoxy-3,4-dihydronaphthalen-1(2H)-one (11.0 g, 53.4 mmol) in toluene (500 mL) was degassed with nitrogen for 15 min. After portion wise addition of anhydrous AlCl₃ (35.6 g, 267 mmol) the reaction mixture was stirred at reflux for 2 h. Then, it was allowed to cool to room temperature, poured over ice (600 g) and added 3 N HCl (80 mL). The suspension was stirred for 10 minutes to get a homogenous precipitate, which was collected by suction filtration, washed with cold water (100 mL) and dried in vacuo to obtain 5,6-dihydroxy-3,4-dihydronaphthalen-1(2H)-one (9.12 g, 96%) as a beige solid, which was used in the next step without further purification; $^1$H NMR (600 MHz, DMSO-$d_6$) δ 10.14 (s, 1H), 8.57 (s, 1H), 7.31 (d, J=8.4 Hz, 1H), 6.75 (d, J=8.4 Hz, 1H), 2.78 (t, J=6.1 Hz, 2H), 2.47-2.41 (m, 2H), 2.00-1.90 (m, 2H); $^{13}$C NMR (151 MHz, DMSO-$d_6$) δ 196.5, 149.9, 141.4, 132.3, 125.0, 113.2, 94.8, 38.2, 22.9, 22.5; LC/ESI-MS (m/z): 179.0 [M+H]+, 200.9 [M+Na]+.

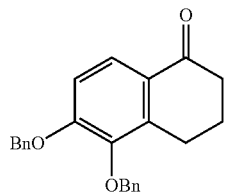 [SMILES: O=C1CCCc2c1ccc(OCc1ccccc1)c2OCc1ccccc1]

NaI (16.3 g, 109 mmol) was added to a solution of benzyl bromide (17.6 mL, 149 mmol) in acetone (480 mL) and the suspension was stirred 15 minutes at room temperature. $K_2CO_3$ (34.2 g, 248 mmol) and 5,6-dihydroxy-3,4-dihydronaphthalen-1(2H)-one (8.82 g, 49.5 mmol) were added and stirred at reflux for 16 h. After cooling to room temperature, water (600 mL) was added, and the product was extracted with ethyl acetate (2×300 mL), and the combined extracts were washed with brine, dried (MgSO$_4$) and solvents were rotary evaporated. The obtained brown solid was purified by dissolving it in hot ethanol (50 mL) followed by treatment with n-hexane (300 mL) and storage at −18° C. for 1 h. The formed crystals were collected by suction filtration, washed with n-hexane and dried in vacuo to obtain 5,6-dihydroxy-3,4-dihydronaphthalen-1(2H)-one (16.0 g, 90%) as a beige solid; $^1$H NMR (600 MHz, CDCl$_3$) δ 7.86 (d, J=8.7 Hz, 1H), 7.47 (br d, J=7.2 Hz, 2H), 7.43-7.32 (m, 8H), 6.99 (d, J=8.7 Hz, 1H), 5.22 (s, 2H), 5.03 (s, 2H), 2.88 (t, J=6.1 Hz, 2H), 2.60-2.52 (m, 2H), 2.07-1.98 (m, 2H); $^{13}$C NMR (90 MHz, CDCl$_3$) δ 197.6, 156.1, 144.5, 139.4, 137.5, 136.4, 128.8, 128.6, 128.5, 128.4, 128.3, 127.6, 127.1, 124.6, 111.7, 74.7, 70.8, 38.8, 23.9, 23.0; LC/ESI-MS (m/z): 359.2 [M+H]+.

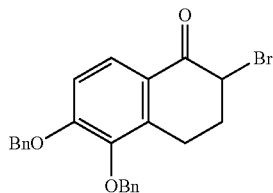

To a suspension of 5,6-bis(benzyloxy)-3,4-dihydronaphthalen-1(2H)-one AS430 (10.0 g, 27.9 mmol) in anhydrous diethyl ether (400 mL) was added dropwise bromine (2.86 mL, 55.8 mmol) over a period of 30 minutes causing the solution to turn red. After 1 h stirring at room temperature the reaction mixture was quenched by adding slowly an aq.ueous NaHCO$_3$ solution (250 mL) and the two layers were separated and the aq.ueous phase was extracted with diethyl ether (150 mL). The combined organic extracts were washed with 10% aq. Na$_2$S$_2$O$_3$ (150 mL), brine, dried (MgSO$_4$) and the solvent was rotary evaporated. The obtained crude mixture of the mono- and α,α-dibrominated tetralone was dissolved in anhydrous THF (75 mL) and cooled on ice. Diethyl phosphite (3.96 mL, 30.7 mmol) was added dropwise followed by addition of triethyl amine (4.28 mL, 30.7 mmol) in THF (20 mL) over a period of 20 minutes. After 8 h stirring at room temperature, water (300 mL) was added, and the product was extracted with ethyl acetate (2×200 mL). The combined organic extracts were washed with brine, dried (MgSO$_4$) and solvents were rotary evaporated. The crude product was purified by recrystallization (n-hexane/DCM, 4:1) and afforded an 5,6-bis(benzyloxy)-2-bromo-3,4-dihydronaphthalen-1(2H)-one as an off-white solid (8.86 g, 73% over 2 steps); $^1$H NMR (360 MHz, CDCl$_3$) δ 7.91 (d, J=8.8 Hz, 1H), 7.50-7.29 (m, 10H), 7.03 (d, J=8.8 Hz, 1H), 5.23 (s, 2H), 5.06 (s, 2H), 4.64 (t, J=4.2 Hz, 1H), 3.07-2.85 (m, 2H), 2.42-2.28 (m, 2H); $^{13}$C NMR (91 MHz, CDCl$_3$) δ 189.8, 156.7, 144.4, 138.1, 137.3, 136.1, 128.9, 128.62, 128.60, 128.5, 128.4, 127.6, 126.2, 124.0, 112.3, 74.7, 70.9, 50.4, 31.6, 20.7; LC/ESI-MS (m/z): 437.1 [M+H]+.

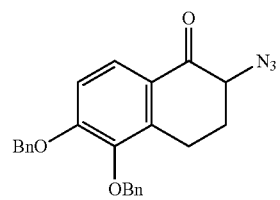 [SMILES: [N-]=[N+]=NC1CCc2c(ccc(OCc3ccccc3)c2OCc2ccccc2)C1=O]

To a solution of 5,6-bis(benzyloxy)-2-bromo-3,4-dihydronaphthalen-1(2H)-one AS434 (1.44 g, 3.29 mmol) in DMF (50 mL) was added glacial acetic acid (0.23 mL, 3.95 mmol) at 0° C., followed by dropwise addition of a solution of sodium azide (428 mg, 6.59 mmol) in water (3 mL). The reaction mixture was stirred at 0° C. for 4 h. After addition of water (50 mL), the product was extracted with DCM (3×40 mL). The combined organic extracts were washed with water, brine, dried (MgSO$_4$) and solvents were rotary evaporated. The obtained oil was then taken up in Et$_2$O (30 mL) and washed with water (3×50 mL), brine, dried and evaporated to dryness to reveal 2-azido-5,6-bis(benzyloxy)-3,4-dihydronaphthalen-1(2M-one (1.22 g, 93%) as a green solid, which was used in the next step without further purification; $^1$H NMR (360 MHz, CDCl$_3$) δ 7.88 (d, J=8.7 Hz, 1H), 7.49-7.29 (m, 10H), 7.02 (d, J=8.8 Hz, 1H), 5.23 (s, 2H), 5.07-4.97 (m, 2H), 4.12 (dd, J=12.1, 4.7 Hz, 1H), 3.14 (dt, J=17.6, 4.4 Hz, 1H), 2.75-2.62 (m, 1H), 2.25 (dq, J=13.4, 4.5 Hz, 1H), 2.04-1.85 (m, 1H); $^{13}$C NMR (91 MHz, CDCl$_3$) δ 192.8, 156.7, 144.5, 138.3, 137.3, 136.1, 128.9, 128.6, 128.6, 128.5, 128.4, 127.6, 125.4, 125.3, 112.4, 74.8, 71.0, 64.1, 28.9, 22.1; LC/ESI-MS (m/z): positive mode 400.2 [M+H]+.

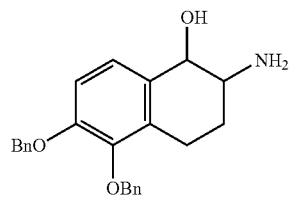 [SMILES: NC1CCc2c(ccc(OCc3ccccc3)c2OCc2ccccc2)C1O]

To a solution of the crude material of 2-azido-5,6-bis(benzyloxy)-3,4-dihydronaphthalen-1(2M-one (1.16 g, 2.90 mmol) in 1,2-dichloroethane (50 mL) was added lithium aluminium hydride (2.18 mL, 8.72 mmol, 4 M in diethyl ether) dropwise over a period of 30 minutes under $N_2$ atmosphere. The reaction mixture was stirred for 4 h at room temperature, then cooled on ice and quenched by careful addition of water (40 mL). The product was extracted with dichloromethane (2×20 mL), and the combined extracts were washed with brine, dried ($MgSO_4$) and solvents were rotary evaporated to obtain 2-amino-5,6-bis(benzyloxy)-1,2,3,4-tetrahydronaphthalen-1-ol (710 mg, 66%, trans:cis 7:5) as a green solid. Trans- and cis-2-amino-5,6-bis(benzyloxy)-1,2,3,4-tetrahydronaphthalen-1-ol were separated by silica gel chromatography (dichloromethane/methanol, 15:1 to 7:1 v/v) to yielded first the trans-isomer (404 mg, 37%) and then cis-isomer (306 mg, 28%) as a colorless solid; trans: $^1$H NMR (400 MHz, $CD_3OD$) δ 7.50-7.45 (m, 2H), 7.40-7.25 (m, 9H), 7.09 (d, J=8.7 Hz, 1H), 5.17 (s, 2H), 5.09-4.94 (m, 2H), 4.55 (d, J=9.3 Hz, 1H), 3.16 (ddd, J=12.3, 9.2, 3.3 Hz, 1H), 2.99 (ddd, J=17.8, 5.8, 2.9 Hz, 1H), 2.69 (ddd, J=17.7, 11.5, 6.0 Hz, 1H), 2.24-2.11 (m, 1H), 1.86-1.72 (m, 1H); $^{13}$C NMR (150 MHz, $CD_3OD$) δ 152.3, 146.0, 139.0, 138.5, 131.8, 130.9, 129.7, 129.6, 129.3, 129.12, 129.07, 128.9, 123.8, 114.1, 75.3, 71.9, 71.4, 55.5, 26.2, 23.5; cis: $^1$H NMR (400 MHz, $CD_3OD$) δ 7.51-7.46 (m, 2H), 7.40-7.28 (m, 9H), 7.15-7.07 (m, 1H), 5.18 (s, 2H), 5.04-4.98 (m, 2H), 4.69 (d, J=3.1 Hz, 1H), 3.39 (dt, J=12.3, 3.5 Hz, 1H), 3.09 (ddd, J=17.8, 5.7, 2.5 Hz, 1H), 2.61 (ddd, J=18.0, 11.7, 6.4 Hz, 1H), 2.04 (ddd, J=24.4, 12.3, 5.9 Hz, 1H), 1.97-1.88 (m, 1H); $^{13}$C NMR (150 MHz, $CD_3OD$) δ 151.5, 145.0, 137.1, 137.0, 129.6, 129.2, 128.2, 128.1, 127.9, 127.7, 127.6, 127.40, 126.0, 112.7, 73.9, 70.4, 65.5, 51.3, 22.0, 20.5; LC/ESI-MS (m/z): positive mode 376.2 $[M+H]^+$.

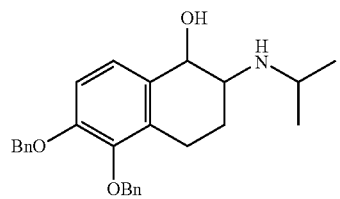 [SMILES: CC(C)NC1CCc2c(ccc(OCc3ccccc3)c2OCc2ccccc2)C1O]

To a solution of 2-amino-5,6-bis(benzyloxy)-1,2,3,4-tetrahydronaphthalen-1-ol (135 mg, 0.36 mmol) in 1,2-DCE (14 mL) were added acetone (1.75 mL) and $NaBH(OAc)_3$ (305 mg, 1.44 mmol). After the reaction mixture was stirred at room temperature for 2 h, it was quenched with water (25 mL) and extracted with DCM (3×20 mL). The combined extracts were washed with brine, dried ($MgSO_4$) and solvents were rotary evaporated. The diastereomeric mixture (ratio trans:cis ~7:5) was purified by semi-preparative chiral HPLC (Daicel IC SemiPrep column, 20% i-PrOH (0.1% EDA), 80% n-hexane, flow 7 mL/min, peaks eluted at 8.7 min, 13.2 min, 16.5 min) and first yielded pure (S,S)-5,6-bis(benzyloxy)-2-(isopropylamino)-1,2,3,4-tetrahydronaphthalen-1-ol (57.0 mg, 36%) a mixture of (R,R)- and (R,S)-5,6-bis(benzyloxy)-2-(isopropylamino)-1,2,3,4-tetrahydronaphthalen-1-ol (75.0 mg, 50%) and pure (S,R)-5,6-bis(benzyloxy)-2-(isopropylamino)-1,2,3,4-tetrahydronaphthalen-1-ol (20.0 mg, 14%); trans-isomer: $^1$H NMR (600 MHz, $CDCl_3$) δ 7.47 (d, J=7.3 Hz, 2H), 7.44-7.23 (m, 9H), 6.96 (d, J=8.5 Hz, 1H), 5.15 (s, 2H), 5.09-5.00 (m, 2H), 4.33 (d, J=8.6 Hz, 1H), 3.10-3.01 (m, 1H), 2.98 (ddd, J=17.7, 5.5, 3.3 Hz, 1H), 2.78-2.62 (m, 2H), 2.24-2.14 (m, 1H), 1.50-1.41 (m, 1H), 1.14 (d, J=6.3 Hz, 3H), 1.07 (d, J=6.1 Hz, 3H); $^{13}$C NMR (150 MHz, $CDCl_3$) δ 150.6, 145.2, 137.9, 137.1, 131.9, 130.6, 128.5, 128.3, 128.2, 127.8, 127.8, 127.4, 122.6, 112.6, 74.1, 72.8, 70.9, 57.7, 45.5, 26.1, 24.5, 23.1, 22.7; cis-isomer: $^1$H NMR (600 MHz, $CDCl_3$) δ 7.46 (br d, J=7.2 Hz, 2H), 7.44-7.29 (m, 8H), 7.19 (d, J=8.4 Hz, 1H), 6.95 (d, J=8.4 Hz, 1H), 5.15 (s, 2H), 5.08-4.99 (m, 2H), 4.56 (d, J=3.8 Hz, 1H), 3.05-2.92 (m, 3H), 2.69-2.59 (m, 1H), 1.92-1.72 (m, 1H), 1.69-1.58 (m, 1H), 1.12 (dd, J=6.7, 6.7 Hz, 6H); $^{13}$C NMR (90 MHz, $CDCl_3$) δ 151.2, 145.6, 138.1, 137.3, 131.2, 131.1, 128.7, 128.5, 128.4, 128.03, 128.00, 127.6, 126.4, 113.0, 74.3, 71.10, 67.07, 54.3, 46.0, 24.0, 23.9, 23.5, 22.6; LC/ESI-MS (m/z): positive mode 418.2 $[M+H]^+$.

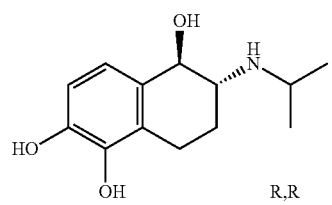

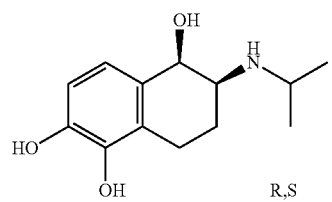

10% Pd/C (8.00 mg, 10 wt %) was added to a solution of a mixture of (R,R)- and (R,S)-5,6-bis(benzyloxy)-2-(isopropylamino)-1,2,3,4-tetrahydronaphthalen-1-ol (77 mg, 0.18 mmol) in ethanol (10 mL) and stirred under $H_2$ atmosphere for 1 h. After filtration of the Pd-catalyst through a syringe filter (0.2 μm), the solvent was rotary evaporated. Purification by preparative HPLC (acetonitrile in 0.1% aq. TFA, 5% to 20%) first yielded pure (R,R)-1,5,6-trihydroxy-N-isopropyl-1,2,3,4-tetrahydronaphthalen-2-aminium TFA (37.0 mg, 61%) and then (R,S)-1,5,6-trihydroxy-N-isopropyl-1,2,3,4-tetrahydronaphthalen-2-aminium TFA (8.00 mg, 13%); (R,R)-1,5,6-trihydroxy-N-isopropyl-1,2,3,4-tetrahydronaphthalen-2-aminium TFA: $^1$H NMR (600 MHz, $CD_3OD$) δ 6.91 (dd, J=8.4, 0.6 Hz, 1H), 6.74 (d, J=8.3 Hz, 1H), 4.62 (d, J=9.0 Hz, 1H), 3.76-3.69 (m, 1H), 3.27 (ddd, J=12.1, 9.1, 3.1 Hz, 1H), 3.02 (ddd, J=17.6, 5.6, 2.9 Hz, 1H), 2.73 (ddd, J=17.5, 11.6, 5.8 Hz, 1H), 2.34-2.30 (m, 1H), 1.81 (qd, J=12.0, 5.7 Hz, 1H), 1.43 (d, J=6.6 Hz, 3H), 1.38 (d, J=6.5 Hz, 3H); $^{13}$C NMR (150 MHz, $CD_3OD$) δ 143.2, 129.9, 123.7, 118.9, 114.6, 71.3, 60.2, 50.1, 24.6, 23.0, 19.9, 19.0; (R,R)-1,5,6-trihydroxy-N-isopropyl-1,2,3,4-tetrahydronaphthalen-2-aminium TFA: $^1$H NMR (600 MHz, MeOD) δ 6.75 (d, J=8.2 Hz, 1H), 6.73 (d, J=8.2 Hz, 1H), 4.76 (d, J=2.4 Hz, 1H), 3.70-3.63 (m, 1H), 3.50 (dt, J=12.7, 3.3 Hz, 1H), 3.09 (ddd, J=17.6, 5.7, 1.5 Hz, 1H), 2.67-2.59 (m, 1H), 2.12 (qd, J=12.5, 5.9 Hz, 1H), 2.04-1.96 (m, 1H), 1.49 (d, J=6.5 Hz, 3H), 1.38 (d, J=6.5 Hz, 3H); $^{13}$C NMR (150 MHz, $CD_3OD$) δ 146.0, 128.5, 124.0, 122.7, 114.6, 65.6, 56.7, 48.3, 23.2, 21.2, 20.1, 19.0; LC/ESI-MS (m/z): 238.0 [M+H]+; HRMS-ESI (m/z): [M+H]+: calcd. for $C_{13}H_{13}NO_3$: 238.1438, found: 238.1438.

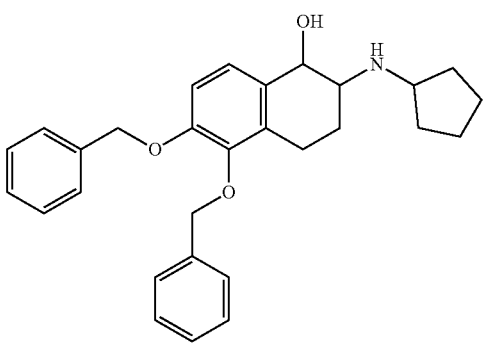 [SMILES: OC1c2ccc(OCc3ccccc3)c(OCc3ccccc3)c2CCC1NC1CCCC1]

2-amino-5,6-bis(benzyloxy)-1,2,3,4-tetrahydronaphthalen-1-ol (130 mg, 346 µmol) was taken in MeOH (10 mL), glacial AcOH (3 drops) and cyclopentanone (1 mL), and to the stirred solution was added NaBH(OAc)$_3$ (294 mg, 1.38 mmol). An additional portion of NaBH(OAc)$_3$ was added each day until complete consumption of starting material was detected by LCMS. After 3 d, the reaction was concentrated, then immediately purified by preparative HPLC (Waters, 0.1% TFA/MeCN, gradient 0% MeCN to 80% over 21 min, product eluted at 16.5 min). The product-containing eluents were then lyophilized to reveal 5,6-bis(benzyloxy)-2-(cyclopentylamino)-1,2,3,4-tetrahydronaphthalen-1-ol as the TFA salt as a white amorphous solid (123 mg, 65%), and the diastereomers were then further separated by chiral semi-preparative HPLC (ChiralPak IC Semi-Prep, 5 µm, 10×250 mm). Isocratic elution with 20% solvent A (0.1% ethylenediamine in propan-2-ol), 80% solvent B (hexane) over 11 min.) to give 4 products (m$_{P1}$=13 mg, eluted at t$_R$=5.6 min; m$_{P2}$=18 mg, eluted at t$_R$=6.8 min; m$_{P3}$=30 mg, eluted at t$_R$=8.1 min; m$_{P4}$=42 mg, eluted at t$_R$=9.1 min) as clear oils. Absolute stereochemistry was assigned according to mosher analyses. trans: $^1$H NMR (600 MHz, CDCl$_3$) δ 7.47-7.44 (m, 2H), 7.42-7.36 (m, 4H), 7.36-7.30 (m, 4H), 7.29-7.27 (m, 2H), 6.94 (d, J=8.6 Hz, 1H), 5.14 (s, 2H), 5.06-4.98 (m, 2H), 4.36 (d, J=8.9 Hz, 1H), 3.34 (p, J=6.6 Hz, 1H), 3.03-2.95 (m, 1H), 2.73-2.62 (m, 2H), 2.42-2.18 (m, 3H), 1.95-1.88 (m, 1H), 1.83-1.77 (m, 1H), 1.77-1.68 (m, 2H), 1.64-1.52 (m, 2H), 1.52-1.43 (m, 1H), 1.43-1.34 (m, 2H). $^{13}$C NMR (91 MHz, CDCl$_3$) δ 150.8, 145.5, 138.1, 137.3, 132.0, 130.7, 128.7, 128.5, 128.4, 128.0, 128.0, 127.6, 122.7, 113.0, 74.3, 72.8, 71.1, 59.5, 56.8, 34.3, 33.0, 25.9, 24.0, 23.9, 23.4. cis: $^1$H NMR (600 MHz, CDCl$_3$) δ 7.46 (dd, J=7.8, 0.9 Hz, 2H), 7.42-7.35 (m, 4H), 7.35-7.30 (m, 4H), 7.18 (d, J=8.5 Hz, 1H), 6.94 (d, J=8.5 Hz, 1H), 5.15 (s, 2H), 5.05 (d, J=10.9 Hz, 1H), 5.00 (d, J=10.9 Hz, 1H), 4.63 (d, J=3.8 Hz, 1H), 3.36-3.26 (m, 1H), 3.02-2.91 (m, 2H), 2.66-2.58 (m, 2H), 1.96-1.85 (m, 3H), 1.76-1.66 (m, 3H), 1.62-1.51 (m, 2H), 1.47-1.40 (m, 1H), 1.36 (dd, J=12.7, 8.0 Hz, 1H), 1.22 (d, J=6.1 Hz, 1H). $^{13}$C NMR (151 MHz, CDCl$_3$) δ 151.3, 145.6, 138.1, 137.2, 131.0, 130.7, 128.7, 128.5, 128.4, 128.1, 128.0, 127.6, 126.4, 113.0, 74.3, 71.1, 66.7, 57.2, 56.0, 33.4, 23.9, 23.3, 22.6. (m/z): [M+H]$^+$ 444.6.

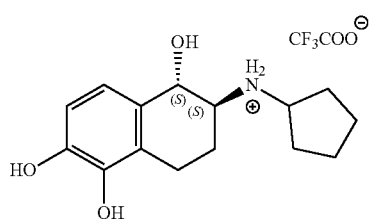

(1 S,2S)-5,6-bis(benzyloxy)-2-(cyclopentylamino)-1,2,3,4-tetrahydronaphthalen-1-ol (15 mg, 34 µmol) was taken in MeOH (5 mL) and the solution was degassed and atmosphere replaced with nitrogen three times. Then Pd/C (10%, 3.6 mg, 3.4 µmol) was added, and the atmosphere replaced with hydrogen. After 2 h stirring at RT, the reaction was filtered through a syringe 0.2 µm filter, and the crude product was purified by preparative HPLC (5-30% MeCN in water+ 0.1% TFA over 15 min), to yield (1 S,2S)-6-(cyclopentylamino)-5,6,7,8-tetrahydronaphthalene-1,2,5-triol trifluoroacetate as a white amorphous solid (6 mg, 67%). $^1$H NMR (600 MHz, MeOD) δ 6.90 (d, J=8.4 Hz, 1H), 6.74 (d, J=8.3 Hz, 1H), 4.61 (d, J=8.7 Hz, 1H), 3.88 (p, J=7.6 Hz, 1H), 3.20 (ddd, J=11.8, 8.8, 3.1 Hz, 1H), 3.00 (ddd, J=17.6, 5.6, 3.5 Hz, 1H), 2.77-2.69 (m, 1H), 2.42-2.35 (m, 1H), 2.25-2.10 (m, 2H), 1.88-1.61 (m, 7H). $^{13}$C NMR (151 MHz, MeOD) δ 145.2, 143.2, 129.7, 123.7, 119.2, 114.6, 71.0, 61.8, 58.4, 31.0, 30.8, 25.0, 24.9, 24.3, 22.9. HRMS (m/z): [M+H]$^+$ calcd for C$_{15}$H$_{22}$NO$_3$, 264.1594; found, 264.1598.

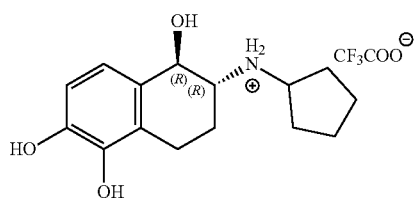

(1R,2R)-6-(Cyclopentylamino)-5,6,7,8-tetrahydronaphthalene-1,2,5-triol trifluoroacetate (6 mg, 51%) was prepared as described for (1S,2S)-6-(cyclopentylamino)-5,6,7,8-tetrahydronaphthalene-1,2,5-triol, starting from (1R,2R)-5,6-bis(benzyloxy)-2-(cyclopentylamino)-1,2,3,4-tetrahydronaphthalen-1-ol (20 mg, 45 µmol). $^1$H NMR (360 MHz, MeOD) δ 6.90 (dd, J=1.0, 8.4 Hz, 1H), 6.73 (d, J=8.4 Hz, 1H), 4.62 (d, J=8.8 Hz, 1H), 3.89 (p, J=7.5 Hz, 1H), 3.21 (ddd, J=3.2, 8.7, 11.8 Hz, 1H), 3.00 (ddd, J=3.6, 5.9, 17.7 Hz, 1H), 2.72 (ddd, J=5.9, 11.1, 17.4 Hz, 1H), 2.39 (ddt, J=3.3, 6.2, 12.8 Hz, 1H), 2.16 (q, J=7.1, 8.2 Hz, 2H), 1.96-1.59 (m, 6H).

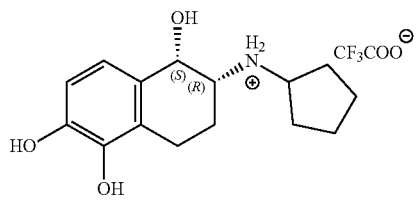

(1 S,2R)-6-(Cyclopentylamino)-5,6,7,8-tetrahydronaphthalene-1,2,5-triol trifluoroacetate (8 mg, 90%) was prepared as described for (1S,2S)-6-(cyclopentylamino)-5,6,7,8-tetrahydronaphthalene-1,2,5-triol, starting from (1 S,2R)-5,6-bis(benzyloxy)-2-(cyclopentylamino)-1,2,3,4-tetrahydronaphthalen-1-ol. $^1$H NMR (600 MHz, MeOD) δ 6.75 (d, J=8.2 Hz, 1H), 6.73 (d, J=8.2 Hz, 1H), 4.79 (d, J=2.8 Hz, 1H), 3.82 (p, J=7.7 Hz, 1H), 3.40 (dt, J=12.1, 3.7 Hz, 1H), 3.09 (ddd, J=17.6, 5.5, 2.0 Hz, 1H), 2.68-2.58 (m, 1H), 2.22-2.03 (m, 4H), 1.89-1.80 (m, 2H), 1.75-1.64 (m, 4H). $^{13}$C NMR (151 MHz, MeOD) δ 145.9, 128.5, 124.0, 122.6, 114.6, 65.8, 58.6, 57.1, 31.1, 30.6, 25.0, 24.9, 23.2, 21.0.

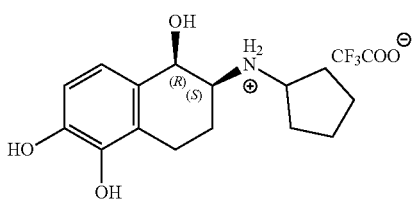

Starting from (1R,2S)-5,6-bis(benzyloxy)-2-(cyclopentylamino)-1,2,3,4-tetrahydronaphthalen-1-ol (20 mg, 45 µmol), and following the same procedure as described for the enantiomer, (1R,2S)-6-(cyclopentylamino)-5,6,7,8-tetrahydronaphthalene-1,2,5-triol trifluoroacetate was afforded as a white amorphous solid (11 mg, 93%). $^1$H NMR (600 MHz, MeOD) δ 6.75 (d, J=8.2 Hz, 1H), 6.73 (d, J=8.2 Hz, 1H), 4.79 (d, J=2.8 Hz, 1H), 3.82 (p, J=7.7 Hz, 1H), 3.40 (dt, J=12.1, 3.7 Hz, 1H), 3.09 (ddd, J=17.6, 5.5, 2.0 Hz, 1H), 2.68-2.58 (m, 1H), 2.22-2.03 (m, 4H), 1.89-1.80 (m, 2H), 1.75-1.64 (m, 4H). $^{13}$C NMR (151 MHz, MeOD) δ 145.9, 128.5, 124.0, 122.6, 114.6, 65.8, 58.6, 57.1, 31.1, 30.6, 25.0, 24.9, 23.2, 21.0.

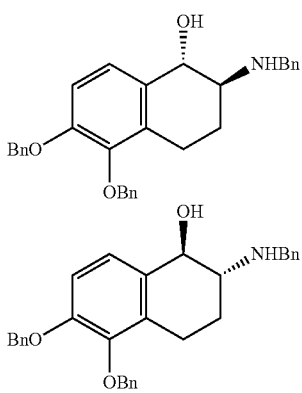

To a solution of trans-2-amino-5,6-bis(benzyloxy)-1,2,3,4-tetrahydronaphthalen-1-ol (315 mg, 0.85 mmol) in 1,2-DCE (20 mL) and MeOH (0.5 mL) were added benzaldehyde (86 µL, 0.85 mmol) and NaBH(OAc)$_3$ (723 mg, 3.42 mmol). After the reaction mixture was stirred at room temperature for 3 h, it was quenched with 5% aq. NaHCO$_3$ (25 mL) and extracted with DCM (3×20 mL). The combined extracts were washed with brine, dried (MgSO$_4$) and solvents were rotary evaporated. The crude material was purified by flash chromatography (dichloromethane/methanol, 20:1 v/v) to obtain trans-2-(benzylamino)-5,6-bis(benzyloxy)-1,2,3,4-tetrahydronaphthalen-1-ol (310 mg, 78%) as a colorless solid. The two enantiomers were separated by semi-preparative chiral HPLC (Daicel IC SemiPrep column, acetonitrile (0.1% EDA), flow 7 mL/min, peaks eluted at 2.9 and 3.9 min) and first yielded pure (S,S)-2-(benzylamino)-5,6-bis(benzyloxy)-1,2,3,4-tetrahydronaphthalen-1-ol (129 mg, 42%) and pure (R,R)-2-(benzylamino)-5,6-bis(benzyloxy)-1,2,3,4-tetrahydronaphthalen-1-ol (131 mg, 42%); $^1$H NMR (600 MHz, CDCl$_3$) δ 7.47-7.42 (m, 2H), 7.41-7.28 (m, 12H), 7.25-7.22 (m, 3H), 6.92 (d, J=8.6 Hz, 1H), 5.13 (s, 2H), 5.00 (s, 2H), 4.41 (d, J=8.5 Hz, 1H), 4.00 (d, J=13.1 Hz, 1H), 3.79 (d, J=13.1 Hz, 1H), 3.00-2.92 (m, 1H), 2.72-2.59 (m, 2H), 2.27-2.18 (m, 1H), 1.54-1.45 (m, 1H); $^{13}$C NMR (100 MHz, CDCl$_3$) δ 150.7, 145.3, 140.4, 137.9, 137.1, 131.9, 130.8, 128.52, 128.48, 128.3, 128.2, 128.1, 127.89, 127.87, 127.4, 127.1, 122.7, 112.7, 74.2, 72.9, 70.9, 59.9, 50.9, 25.4, 22.9; LC/ESI-MS (m/z): positive mode 466.2 [M+H]$^+$.

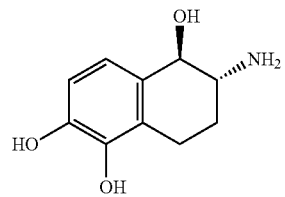 [SMILES: N[C@@H]1CCc2c(ccc(O)c2O)[C@H]1O]

10% Pd/C (2.00 mg, 10 wt %) was added to a solution of (R,S)-2-(Benzylamino)-5,6-bis(benzyloxy)-1,2,3,4-tetrahydronaphthalen-1-ol (20.0 mg, 43.0 µmol) in ethanol (4 mL) and stirred under H$_2$ atmosphere for 16 h. After filtration of the Pd-catalyst through a syringe filter (0.2 µm), the solvent was rotary evaporated. Purification by preparative HPLC (2% acetonitrile in 0.1% aq. TFA, peak eluted at 4.1 min) yielded (5R,6R)-6-amino-5,6,7,8-tetrahydronaphthalene-1,2,5-triol×TFA (11.9 mg, 95%) as a light purple solid; $^1$H NMR (600 MHz, CD$_3$OD) δ 6.88 (d, J=8.3 Hz, 1H), 6.72 (d, J=8.3 Hz, 1H), 4.54 (d, J=9.0 Hz, 1H), 3.19 (ddd, J=12.0, 9.0, 3.2 Hz, 1H), 2.97 (ddd, J=17.7, 5.9, 3.0 Hz, 1H), 2.72 (ddd, J=17.5, 11.3, 6.1 Hz, 1H), 2.27-2.20 (m, 1H), 1.85 (ddd, J=24.4, 11.7, 6.0 Hz, 1H); $^{13}$C NMR (150 MHz, CD$_3$OD) δ 145.2, 143.2, 129.8, 123.6, 118.8, 114.5, 71.6, 55.7, 26.0, 22.8; LC/ESI-MS (m/z): positive mode 196.0 [M+H]+; HRMS-ESI (m/z): [M+H]+: calcd. for C$_{10}$H$_{13}$NO$_3$: 196.0968, found: 196.0969. HPLC

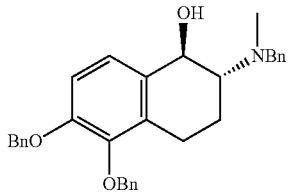 [SMILES: CN(Cc1ccccc1)[C@@H]1CCc2c(ccc(OCc3ccccc3)c2OCc2ccccc2)[C@H]1O]

To a solution of (R,S)-2-(Benzylamino)-5,6-bis(benzyloxy)-1,2,3,4-tetrahydronaphthalen-1-ol (65.0 mg, 0.14 mmol) in 1,2-DCE (7 mL) and MeOH (1 mL) were added formaldehyde (52 µL, 0.70 mmol, aq. 37 wt %) and NaBH(OAc)$_3$ (118 mg, 0.56 mmol). After the reaction mixture was stirred at room temperature for 1 h, it was quenched with 5% aq. NaHCO$_3$ (10 mL) and extracted with DCM (3×8 mL). The combined extracts were washed with brine, dried (MgSO$_4$) and solvents were rotary evaporated to obtain (1R,2R)-2-(benzyl(methyl)amino)-5,6-bis(benzyloxy)-1,2,3,4-tetrahydronaphthalen-1-ol (72.8 mg, quant.) as a colorless solid, which was used in the next step without further purification; $^1$H NMR (600 MHz, CDCl$_3$) δ 7.47-7.42 (m, 2H), 7.41-7.29 (m, 13H), 7.28-7.23 (m, 1H), 6.94 (d, J=8.6 Hz, 1H), 5.13 (s, 2H), 5.00 (s, 2H), 4.65 (d, J=9.6 Hz, 1H), 3.86-3.67 (m, 1H), 3.51 (d, J=12.9 Hz, 1H), 3.08 (ddd, J=17.4, 5.5, 1.7 Hz, 1H), 2.79-2.65 (m, 1H), 2.65-2.53 (m, 1H), 2.27 (s, 3H), 2.04 (ddd, J=8.4, 6.0, 3.0 Hz, 1H), 1.56 (qd, J=12.4, 5.8 Hz, 2H); $^{13}$C NMR (100 MHz, CDCl$_3$) δ 150.4, 145.3, 137.9, 137.2, 132.2, 123.0, 128.8, 128.49, 128.45, 128.3, 128.2, 127.8, 127.4, 127.2, 122.3, 112.8, 74.2, 70.9, 68.7, 65.8, 58.2, 36.6, 24.1, 18.3, one carbon not visible; LC/ESI-MS (m/z): 480.3 [M+H]$^+$.

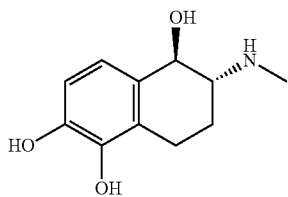

10% Pd/C (6.50 mg, 10 wt %) was added to a solution of (1R,2R)-2-(benzyl(methyl)amino)-5,6-bis(benzyloxy)-1,2,3,4-tetrahydronaphthalen-1-ol (65.0 mg, 135 μmol) in ethanol (10 mL) and stirred under $H_2$ atmosphere for 4 h. After filtration of the Pd-catalyst through a syringe filter (0.2 μm), the solvent was rotary evaporated. Purification by preparative HPLC (3% acetonitrile in 0.1% aq.TFA, peak eluted at 3.5 min) yielded (5R,6R)-6-(methylamino)-5,6,7,8-tetrahydronaphthalene-1,2,5-triol×TFA (33.1 mg, 74%) as a colorless solid; $^1$H NMR (600 MHz, $CD_3OD$) δ 6.88 (d, J=8.4 Hz, 1H), 6.73 (d, J=8.3 Hz, 1H), 4.63 (d, J=9.0 Hz, 1H), 3.15 (ddd, J=11.9, 9.0, 3.1 Hz, 1H), 2.99 (ddd, J=17.7, 5.8, 3.3 Hz, 1H), 2.79 (s, 3H), 2.72 (ddd, J=17.5, 11.1, 6.1 Hz, 1H), 2.39-4.33 (m, 1H), 1.86-1.77 (m, 1H); $^{13}$C NMR (150 MHz, $CD_3OD$) δ 145.2, 143.2, 129.6, 123.5, 118.9, 114.6, 70.5, 63.3, 31.1, 23.2, 22.8; LC/ESI-MS (m/z): 210.0 [M+H]+; HRMS-ESI (m/z): [M+H]+: calcd. for $C_{11}H_{15}NO_3$: 210.1125, found: 210.1123.

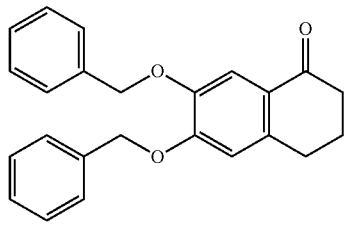 [SMILES: O=C1CCCc2cc(OCc3ccccc3)c(OCc3ccccc3)cc21]

6,7-Dimethoxy-1-tetralone (2.18 g, 10.6 mmol) was taken in toluene (60 mL), and nitrogen was bubbled through the solution for 15 min. Then $AlCl_3$ (7.05 g, 52.9 mmol) was added, and the yellow solution heated to reflux. Within 1 h the reaction had turned black in colour and a precipitate had emerged. The heat was removed, and the reaction continued stirring at RT overnight. After 16 h, the reaction was cooled on ice, then water (20 mL) and 2 M HCl (20 mL) were added with stirring. After 15 min on ice, the precipitate was collected by filtration and washed with water. The solid was then taken in MeOH (30 mL) and filtered through a sintered filter, then the filtrate evaporated to dryness, and the remaining orange solid was taken in acetone (60 mL), and to the red solution was added benzyl bromide (3.02 mL, 25.4 mmol), potassium carbonate (5.86 g, 42.4 mmol) and sodium iodide (254 mg, 1.69 mmol), and the reaction heated to reflux. After 16 h, the inorganic solids were removed by filtration through sinter, and washed with acetone (40 mL). The filtrate was evaporated to dryness, then the product purified by recrystallization from DCM/Hex to give 6,7-bis(benzyloxy)-3,4-dihydronaphthalen-1(2H)-one as pale yellow needles (2.02 g, 53%). $^1$H NMR (600 MHz, $CDCl_3$) δ 7.64 (s, 1H), 7.50-7.43 (m, 4H), 7.41-7.29 (m, 6H), 6.74 (s, 1H), 5.22 (s, 2H), 5.19 (s, 2H), 2.85 (t, J=6.1 Hz, 2H), 2.61-2.55 (m, 2H), 2.14-2.06 (m, 2H). $^{13}$C NMR (151 MHz, $CDCl_3$) δ 197.3, 153.5, 147.7, 139.7, 137.1, 136.6, 128.7, 128.6, 128.1, 128.0, 127.5, 127.2, 126.4, 113.0, 111.8, 71.1, 70.9, 38.7, 29.6, 23.7.

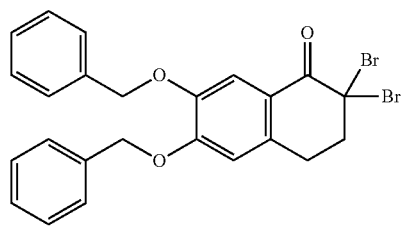 [SMILES: O=C1c2cc(OCc3ccccc3)c(OCc3ccccc3)cc2CCC1(Br)Br]

6,7-bis(benzyloxy)-3,4-dihydronaphthalen-1(2H)-one (2.00 g, 5.58 mmol) was taken in $Et_2O$ (30 mL) and DCM (30 mL), and to the stirred solution at RT was dropwise added a solution of $Br_2$ (572 μL, 11.16 mmol) in $Et_2O$ (30 mL). After 5 min, TLC (2:1 Hex/EtOAc) showed complete consumption of starting material. Then 50% $NaHCO_3$ solution (20 mL) was slowly added, and the product extracted with DCM (2×30 mL). The combined organic extracts were washed with $Na_2S_2O_3$ (10% aq sol, 30 mL), brine, dried and evaporated to give a brown oil. 6,7-Bis(benzyloxy)-2,2-dibromo-3,4-dihydronaphthalen-1(2H)-one was purified by recrystallization (DCM/Hex) to give white fluffy needles (2.26 g, 93%). $^1$H NMR (360 MHz, $CDCl_3$) δ 7.96 (d, J=184.2 Hz, 1H), 7.50-7.28 (m, 10H), 6.71 (s, 1H), 5.23 (s, 2H), 5.19 (s, 2H), 3.07-3.00 (m, 2H), 3.00-2.94 (m, 2H). $^{13}$C NMR (91 MHz, $CDCl_3$) δ 183.4, 154.6, 148.6, 137.6, 136.7, 136.2, 128.8, 128.7, 128.3, 128.2, 127.5, 127.2, 120.5, 113.8, 112.4, 77.4, 71.2, 71.0, 67.5, 53.6, 46.5, 31.7, 29.3, 22.8, 14.3.

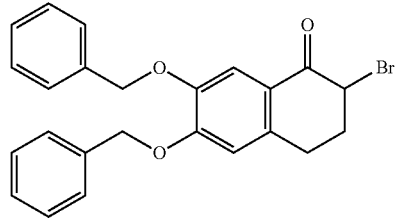 [SMILES: [N-]=[N+]=NC1CCc2cc(OCc3ccccc3)c(OCc3ccccc3)cc2C1=O]

6,7-bis(benzyloxy)-2,2-dibromo-3,4-dihydronaphthalen-1(2H)-one (2.70 g, 5.23 mmol) was taken in dry THF (20 mL) and cooled on ice with stirring. To the solution was dropwise added a solution of diethyl phosphite (743 μL, 5.75 mmol) and triethylamine (802 μL, 5.75 mmol) in THF (10 mL). After 3 d, water (30 mL) was added, and the product extracted with EtOAc (3×40 mL). The combined organic extracts were washed with brine, dried and evaporated, and the product purified by recrystallization (DCM/Hex) to give 6,7-bis(benzyloxy)-2,2-dibromo-3,4-dihydronaphthalen-1(2H)-one as pale orange needles (1.51 g, 66%). $^1$H NMR (360 MHz, $CDCl_3$) δ 7.66 (s, 1H), 7.49-7.27 (m, 10H), 6.75 (s, 1H), 5.23 (s, 2H), 5.18 (s, 2H), 4.67 (t, J=4.2 Hz, 1H), 3.21 (ddd, J=16.4, 9.8, 4.9 Hz, 1H), 2.77 (dt, J=16.9, 4.3 Hz, 1H), 2.53-2.36 (m, 2H). $^{13}$C NMR (91 MHz, $CDCl_3$) δ 189.4, 154.1, 148.0, 138.2, 136.6, 136.2, 128.6, 128.5, 128.0, 127.9, 127.3, 127.0, 123.2, 112.4, 112.4, 70.9, 70.7, 50.2, 32.2, 25.8.

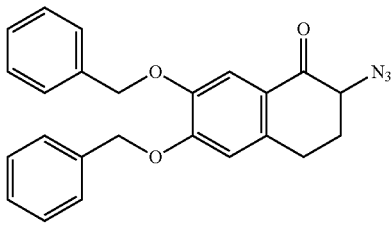

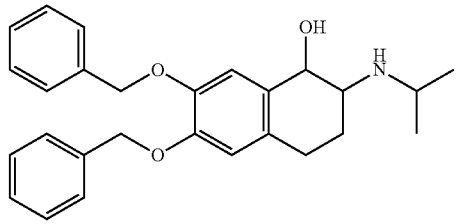

6,7-Bis(benzyloxy)-2-bromo-3,4-dihydronaphthalen-1(2H)-one (1.78 g, 4.07 mmol) was taken in dry DMF (30 mL) and to the stirred solution was added glacial acetic acid (279 µL, 4.88 mmol), followed by dropwise addition of a solution of sodium azide (529 mg, 8.14 mmol) in water (2 mL) at RT. After 1 h, water (50 mL) was added, and the product was extracted with DCM. The combined organic extracts were washed with brine, dried and concentrated in vacuo. The oil was then taken up in $Et_2O$ (30 mL) and washed with water (3×50 mL), brine, dried and evaporated to dryness to give 2-azido-6,7-bis(benzyloxy)-3,4-dihydronaphthalen-1(2H)-one as a brown oil (1.46 g, 90%). $^1$H NMR (360 MHz, $CDCl_3$) δ 7.63 (s, 1H), 7.50-7.29 (m, 10H), 6.71 (s, 1H), 5.22 (s, 2H), 5.19 (s, 2H), 4.15 (dd, J=11.7, 4.7 Hz, 1H), 2.93 (dd, J=7.7, 4.7 Hz, 2H), 2.36-2.23 (m, 1H), 2.14-2.02 (m, 1H). $^{13}$C NMR (91 MHz, $CDCl_3$) δ 192.6, 154.2, 148.1, 138.7, 136.8, 136.3, 128.8, 128.7, 128.3, 128.1, 127.5, 127.2, 124.6, 112.6, 112.0, 71.1, 70.9, 64.0, 29.7, 27.4.

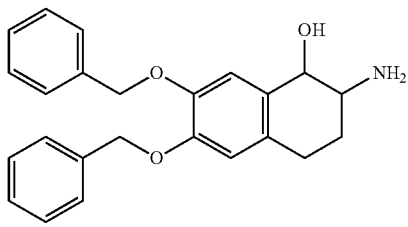 [SMILES: NC1CCc2cc(OCc3ccccc3)c(OCc3ccccc3)cc2C1O]

2-Azido-6,7-bis(benzyloxy)-3,4-dihydronaphthalen-1(2H)-one (440 mg, 1.10 mmol) was taken in 1,2-dichloroethane (20 mL) at r.t., and to the stirred solution was dropwise added $LiAlH_4$ 1 M in THF (4.41 mL, 4.41 mmol, 4 eq.) causing the colour to change from dark brown to light yellow. After 16 h, water (5 mL) was slowly added dropwise, which caused a white precipitate to form and the mixture to turn green. The mixture was then diluted with DCM (20 mL), and extracted twice with DCM (2×20 mL). The combined organic extracts were then washed with brine, dried and evaporated to give 2-amino-6,7-bis(benzyloxy)-1,2,3,4-tetrahydronaphthalen-1-ol in a cis-trans ratio of 4:1 as a green oil (325 mg, 76%). cis: $^1$H NMR (600 MHz, $CDCl_3$) δ 7.47-7.43 (m, 4H), 7.39-7.33 (m, 4H), 7.33-7.29 (m, 2H), 7.04 (s, 1H), 6.68 (s, 1H), 5.19-5.11 (m, 5H), 4.44 (d, J=3.7 Hz, 1H), 3.12 (dt, J=3.4, 10.8 Hz, 1H), 2.77 (dt, J=5.2, 16.9 Hz, 1H), 2.70 (ddd, J=6.0, 9.9, 16.6 Hz, 1H), 1.92-1.83 (m, 1H), 1.76-1.67 (m, 1H). trans: $^1$H NMR (600 MHz, $CDCl_3$) δ 7.42 (t, J=6.5 Hz, 6H), 7.36-7.25 (m, 6H), 7.18 (s, 1H), 6.60 (s, 1H), 5.14-5.03 (m, 4H), 4.42 (d, J=8.6 Hz, 1H), 2.97 (t, J=8.7 Hz, 1H), 2.78 (ddd, J=5.7, 11.6, 17.0 Hz, 1H), 2.70-2.61 (m, 1H), 2.06-1.99 (m, 2H), 1.77-1.64 (m, 1H). (m/z): [M+H]$^+$ 358.2.

2-amino-6,7-bis(benzyloxy)-1,2,3,4-tetrahydronaphthalen-1-ol (80 mg, 213 µmol) was taken in 1,2-DCE (10 mL) in a dried flask, and to the solution was added acetone (1 mL), followed by $NaBH(OAc)_3$ (181 mg, 852 µmol) at RT. After 4 d, the reaction was diluted with DCM (20 mL) and washed with 1 M $K_2CO_3$ (2×20 mL), brine, dried and evaporated to give a brown solid (85 mg, 96%). The crude was then purified by preparative HPLC (Solvent A: 0.1% TFA/$H_2O$, Solvent B: MeCN; gradient 5-80% Solvent B over 17 min, product eluted at 13.9 min), and the product containing fractions were combined and lyophilized to give a white solid (120 mg, 89%). The diastereomeric pairs were then further purified by semi-preparative chiral HPLC (ChiralPak IC Semi-Prep, 5 µm, 10×250 mm, isocratic elution with 100% solvent B (0.1% EDA/MeCN) resulted in elution of 4 peaks at $t_R$=3.8 min, 4.1 min, 4.4 min and 4.8 min). trans: $^1$H NMR (600 MHz, $CDCl_3$) δ 7.49-7.40 (m, 4H), 7.39-7.27 (m, 7H), 7.19 (s, 1H), 6.64 (s, 1H), 5.18-5.09 (m, 4H), 4.46 (d, J=8.8 Hz, 1H), 3.25-3.17 (m, 1H), 3.00 (br s, 1H), 2.88-2.73 (m, 3H), 2.23-2.18 (m, 1H), 1.68-1.58 (m, 1H), 1.21 (d, J=6.3 Hz, 3H), 1.14 (d, J=6.2 Hz, 3H). $^{13}$C NMR (91 MHz, $CDCl_3$) δ 148.5, 148.1, 137.6, 137.5, 130.7, 128.6, 128.6, 128.1, 127.9, 127.8, 127.6, 127.4, 114.9, 113.2, 71.9, 71.5 (d), 58.9, 46.9, 27.9, 26.0, 23.0, 21.4. cis: $^1$H NMR (600 MHz, $CDCl_3$) δ 7.49-7.41 (m, 4H), 7.39-7.34 (m, 4H), 7.32-7.28 (m, 2H), 7.07 (s, 1H), 6.68 (s, 1H), 5.20-5.10 (m, 4H), 4.50 (d, J=4.0 Hz, 1H), 3.02 (tt, J=7.4, 4.9 Hz, 2H), 2.80-2.69 (m, 3H), 2.42 (br s, 1H), 1.97-1.84 (m, 1H), 1.70-1.62 (m, 1H), 1.12 (dd, J=6.3, 3.7 Hz, 6H). $^{13}$C NMR (91 MHz, $CDCl_3$) δ 148.9, 147.9, 137.6, 137.5, 130.1, 129.2, 128.6, 128.6, 127.8, 127.8, 127.5, 127.4, 116.6, 115.0, 71.5, 71.5, 67.0, 54.5, 46.0, 27.4, 24.5, 23.8, 23.5. (m/z): [M+H]$^+$ 400.3

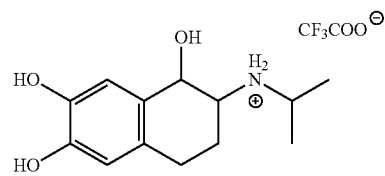

cis-6,7-bis(benzyloxy)-2-(isopropylamino)-1,2,3,4-tetrahydronaphthalen-1-ol (12 mg, 29 µmol) was taken in MeOH (8 mL) and to the solution was added 10% Pd/C (3 mg, 2.8 µmol) and the atmosphere changed to $H_2$. After 16 h, the orange solution was filtered through a syringe filter and the solvent evaporated. The product was then purified by preparative HPLC to give cis-2-(isopropylamino)-1,2,3,4-tetrahydronaphthalene-1,6,7-triol trifluoroacetate as a yellow oil (1 mg, 15%). $^1$H NMR (600 MHz, MeOD) δ 6.79 (s, 1H), 6.56 (s, 1H), 4.69 (d, J=2.9 Hz, 1H), 3.68-3.62 (m, 1H), 3.50 (dt, J=12.7, 3.3 Hz, 1H), 2.86-2.73 (m, 2H), 2.17-2.06 (m, 1H), 1.97-1.88 (m, 1H), 1.38 (dd, J=11.2, 6.5 Hz, 6H). HRMS (m/z): [M+H]$^+$ calcd for $C_{13}H_{20}NO_3$, 238.1438; found, 238.1439.

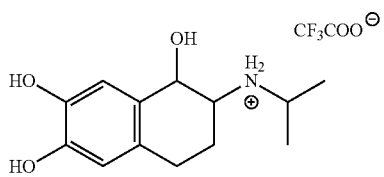

trans-2-(Isopropylamino)-1,2,3,4-tetrahydronaphthalene-1,6,7-triol trifluoroacetate was prepared as a clear oil (1.06 mg) as described for the cis-diastereomer starting from trans-6,7-bis(benzyloxy)-2-(isopropylamino)-1,2,3,4-tetrahydronaphthalen-1-ol. $^1$H NMR (600 MHz, MeOD) δ 6.96 (s, 1H), 6.53 (s, 1H), 4.57 (d, J=8.7 Hz, 1H), 3.71 (dt, J=13.0, 6.4 Hz, 1H), 3.26 (ddd, J=12.1, 8.9, 3.2 Hz, 1H), 2.86 (ddd, J=16.8, 11.8, 5.2 Hz, 1H), 2.77 (ddd, J=16.6, 5.1, 3.2 Hz, 1H), 2.32-2.23 (m, 1H), 1.82 (qd, J=12.2, 5.5 Hz, 1H), 1.82 (qd, J=12.2, 5.5 Hz, 1H), 1.42 (d, J=6.5 Hz, 3H), 1.37 (d, J=6.5 Hz, 3H).

tert-butyl-((1R,2R)-5,6-bis(benzyloxy)-1-hydroxy-1,2,3,4-tetrahydronaphthalen-2-yl)carbamate (LM-85)

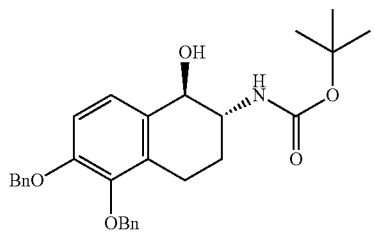

A cis/trans-mixture of LM-51/AS-413 (4.00 g, 10.6 mmol) was dissolved in 100 mL of anhydrous $CH_2Cl_2$. After addition of DIPEA (3.62 mL, 21.3 mmol), Boc-anhydride (4.65 g, 21.3 mmol) was added under a stream of nitrogen and the reaction mixture thereafter stirred over night. It was rotary evaporated and the residue purified by flash column chromatography (isohexane/acetone 5:1 4 isohexane/acetone 2:1), giving rise to fractions enriched with the trans-isomer. The corresponding fractions were partially rotary evaporated, favoring precipitation of the trans-compound. After isolation and recrystallization (toluene/isohexane 2:1) of the trans-isomers, 3.01 g (60%) of a white powder were obtained.

The enantiomers of pure trans-compound were separated on chiral, preparative HPLC (ChiralPakIC) with pure acetonitrile as an eluent, giving first pure (R,R)-enantiomer and secondly pure (S,S)-enantiomer of LM-85.

$[α]_{23}^D$+49.8 (c=0.46 in $CHCl_3$) for R,R-enantiomer
47.7 (c=0.73 in $CHCl_3$) for S,S-enantiomer
ESI-MS m/z 498.04 [M+Na]$^+$
$^1$H NMR (600 MHz, $CDCl_3$) δ 7.45 (d, J=7.3 Hz, 2H), 7.40-7.36 (m, 4H), 7.35-7.30 (m, 4H), 7.24 (d, J=8.5 Hz, 1H), 6.95 (d, J=8.6 Hz, 1H), 5.14 (s, 2H), 5.05 (d, J=11.0 Hz, 1H), 5.00 (d, J=11.0 Hz, 1H), 4.64 (br s, 1H), 4.52 (d, J=7.1 Hz, 1H), 3.80-3.73 (m, 1H), 2.82 (dt, J=17.7, 5.5 Hz, 1H), 2.76-2.70 (m, 1H), 2.12-2.05 (m, 1H), 1.70-1.63 (m, 1H), 1.46 (s, 9H).
$^{13}$C NMR (151 MHz, $CDCl_3$) δ 156.81, 151.01, 145.23, 137.91, 137.16, 131.17, 130.63, 128.69, 128.48, 128.10, 128.08, 127.56, 124.26, 113.05, 80.15, 74.40, 73.42, 71.04, 53.52, 28.52, 25.79, 22.10. (Carbonyl signal not visible).

(1R,2R)-5,6-bis(benzyloxy)-2-(methylamino)-1,2,3,4-tetrahydronaphthalen-1-ol (LM-83)

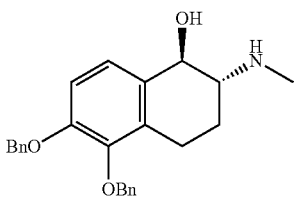 [SMILES: CN[C@@H]1CCc2c(ccc(OCc3ccccc3)c2OCc2ccccc2)[C@H]1O]

This intermediate was prepared by subjecting compound (R,R)-LM-85 to general procedure 3 and purifying the crude product by a silica pad ($CH_2Cl_2$/MeOH 50:1→$CH_2Cl_2$/MeOH 9:1+0.1% $NH_3$ 25%) to give 75% of white powder.
$[α]_{23}^D$+14.1 (c=0.47 in $CHCl_3$)
$^1$H NMR (600 MHz, MeOD) δ 7.48 (d, J=7.3 Hz, 2H), 7.38-7.34 (m, 4H), 7.34-7.28 (m, 4H), 7.22 (d, J=8.6 Hz, 1H), 7.03 (d, J=8.6 Hz, 1H), 5.15 (s, J=6.7 Hz, 2H), 4.99 (d, J=10.8 Hz, 1H), 4.97 (d, J=10.8 Hz, 1H), 4.40 (d, J=7.9 Hz, 1H), 2.86 (dt, J=17.6, 5.1 Hz, 1H), 2.65-2.58 (m, 2H), 2.46 (s, 3H), 2.16-2.09 (m, 1H), 1.55-1.46 (dtd, J=13.2, 10.2, 5.6 Hz, 1H).

(5R,6R)-6-(methylamino)-5,6,7,8-tetrahydronaphthalene-1,2,5-triol (AS-443/LM-54)

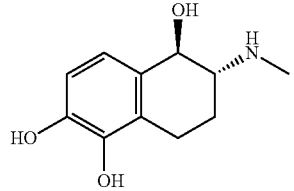

AS-443/LM-54 was prepared in an alternative approach (using LM-83) according to general procedure 5 and the crude TFA salt was purified by prep. HPLC (0.1% TFA in water, acetonitrile, 3% acetonitrile→10% acetonitrile in 10 min., 12.00 mL/min. flowrate, peak eluted at 5.0 min) to give a 45% yield of (5R,6R)-6-(methylamino)-5,6,7,8-tetrahydronaphthalene-1,2,5-triol. For analytical data, see compound AS-443.

(1R,2R)-2-amino-5,6-bis(benzyloxy)-1,2,3,4-tetrahydronaphthalen-1-ol (LM-51)

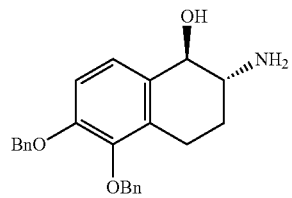

Enantiomerically pure (R,R)-LM-85 (150 mg, 0.32 mmol) was suspended in 2.5 mL THF and treated with 1M TBAF-solution in THF (1.28 mL, 1.28 mmol, 4 eq.). The resulting mixture was refluxed at 90° C. for 4 hours. It was then taken up in water and extracted thrice with $CH_2Cl_2$. The combined organic layers were extensively washed with water to remove the main part of remaining TBAF, dried over $MgSO_4$ and rotary evaporated. The resulting beige solid was obtained in quantitative yield and acceptable purity and therefore used without further purification. The removal of the Boc protecting group was proven to proceed without affecting the enantiopurity of the educt. For analytical data, see data for AS-413 trans.

(1R,2R)-2-(benzyl(3-fluoropropyl)amino)-5,6-bis(benzyloxy)-1,2,3,4-tetrahydronaphthalen-1-ol (LM-70)

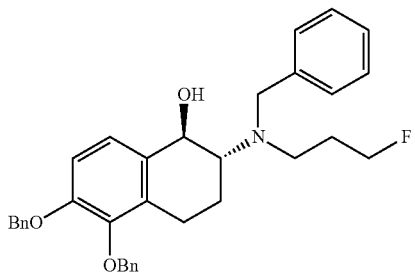 [SMILES: O[C@@H]1c2ccc(OCc3ccccc3)c(OCc3ccccc3)c2CC[C@H]1N(CCCF)Cc1ccccc1]

(R,R)-LM-70 was prepared from (R,R)-AS-438 according to general procedure 4 using 2 eq. of DIPEA and 5 eq. of 1-fluoro-3-iodopropane as an alkylating agent. The reaction yielded 73% of (1R,2R)-2-(benzyl(3-fluoropropyl)amino)-5,6-bis(benzyloxy)-1,2,3,4-tetrahydronaphthalen-1-ol in analytical purity.

ESI-MS m/z 526.23 [M+H]$^+$
$[\alpha]_{22}^D$ −20.2 (c=0.22 in $CH_3OH$)
$^1$H NMR (600 MHz, $CDCl_3$) δ 7.45 (d, J=7.2 Hz, 2H), 7.42-7.30 (m, 12H), 7.29 (d, J=8.7 Hz, 1H), 7.27-7.23 (m, 1H), 6.93 (d, J=8.6 Hz, 1H), 5.15-5.09 (m, 2H), 5.01 (d, J=11.0 Hz, 1H), 4.99 (d, J=11.0 Hz), 4.64 (d, J=9.9 Hz, 1H), 4.53-4.46 (m, 1H), 4.45-4.38 (m, 1H), 3.92 (d, J=13.6 Hz, 1H), 3.47 (d, J=13.7 Hz, 1H), 3.09 (ddd, J=17.5, 5.5, 1.7 Hz, 1H), 2.81 (dt, J=13.3, 7.9 Hz, 1H), 2.72 (ddd, J=12.4, 10.0, 2.6 Hz, 1H), 2.65-2.60 (m, 1H), 2.61-2.54 (m, 1H), 2.12-2.05 (m, 1H), 1.95-1.77 (m, 1H), 1.58 (qd, J=12.4, 5.6 Hz, 1H).
$^{13}$C NMR (151 MHz, $CDCl_3$) δ 150.57, 145.40, 139.52, 138.11, 137.31, 132.25, 130.23, 128.89, 128.71, 128.65, 128.46, 128.38, 128.00, 127.99, 127.57, 127.42, 122.67, 113.03, 82.50 (d, $^1$J ($\underline{C}H_2$—F)=164.8 Hz), 74.33, 71.11, 68.35, 63.22, 54.50, 46.06 (d, $^3$J ($\underline{C}H_2CH_2CH_2$—F)=4.6 Hz), 29.76 (d, $^2$J ($\underline{C}H_2$—$CH_2$—F)=19.4 Hz), 24.47, 19.29.
19F NMR (565 MHz, $CDCl_3$): δ −220.34 (m).

(5R,6R)-6-((3-fluoropropyl)amino)-5,6,7,8-tetrahydronaphthalene-1,2,5-triol (LM-75)

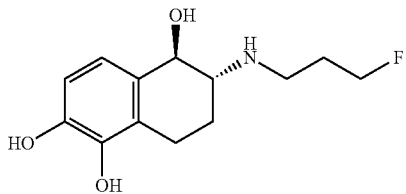 [SMILES: Oc1ccc2c(c1O)CC[C@@H](NCCCF)[C@@H]2O]

(R,R)-LM-75 was prepared from LM-70 according to general procedure 5 and the crude TFA salt was purified by prep. HPLC (0.1% TFA in water, acetonitrile, 5% acetonitrile→20% acetonitrile in 10 min., 8.00 mL/min. flowrate, peak eluted at 7.0 min) to give a 73% yield of product.

ESI-MS m/z 255.95 [M+H]$^+$
$^1$H NMR (600 MHz, MeOD) δ 6.90 (d, J=8.3 Hz, 1H), 6.74 (d, J=8.3 Hz, 1H), 4.67 (d, J=8.9 Hz, 1H), 4.60 (dt, J=47.1, 5.5 Hz, 2H), 3.42-3.29 (m, 2H), 3.25 (ddd, J=11.9, 9.0, 3.0 Hz, 1H), 3.01 (ddd, J=17.6, 5.5, 3.3 Hz, 1H), 2.74 (ddd, J=17.4, 11.2, 5.9 Hz, 1H), 2.40-2.35 (m, 1H), 2.25-2.06 (m, 2H), 1.85 (qd, J=11.8, 5.9 Hz, 1H).
$^{13}$C NMR (151 MHz, MeOD) δ 145.25, 143.23, 129.71, 123.52, 118.93, 114.62, 82.27 (d, $^1$J ($\underline{C}H_2$—F)=164.5 Hz), 70.66, 62.37, 43.51 (d, $^3$J ($\underline{C}H_2$—$CH_2$—$CH_2$—F)=4.9 Hz), 28.38 (d, $^2$J ($\underline{C}H_2$—$CH_2$—F)=20.1 Hz), 23.88, 22.87.

(1R,2R)-5,6-bis(benzyloxy)-2-((2-fluoroethyl)amino)-1,2,3,4-tetrahydronaphthalen-1-ol (LM-78 TFA Salt)

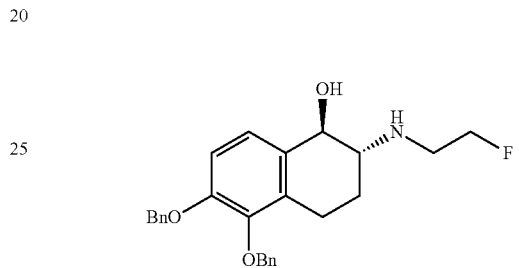

(R,R)-LM-78 was prepared from LM-51 according to general procedure 4 using 1 eq. of DIPEA and 1 eq. of 2-fluoroethyltosylate as an alkylating agent. Flash chromatography ($CH_2Cl_2$→$CH_2Cl_2$/MeOH 200:1→$CH_2Cl_2$/MeOH 30:1) and subsequent preparative HPLC gave (R,R)-LM-78-TFA salt in 8% yield as a colorless, crystalline solid.

$[\alpha]_{23}^D$ +12.4 (c=0.78 in $CH_3OH$)
ESI-MS m/z 422.05 [M+H]$^+$
$^1$H NMR (400 MHz, MeOD) δ 7.51-7.47 (m, 2H), 7.41-7.26 (m, 9H), 7.10 (d, J=8.7 Hz, 1H), 5.18 (s, 2H), 5.03 (d, J=10.8 Hz, 1H), 4.99 (d, J=10.8 Hz, 1H), 4.88-4.71 (m, 2H), 4.72 (d, J=8.5 Hz, 1H), 3.57 (dt, J=26.9, 4.6 Hz, 2H), 3.30-3.23 (m, 1H), 3.03 (ddd, J=17.7, 5.4, 2.9 Hz, 1H), 2.70 (ddd, J=17.5, 11.6, 5.7 Hz, 1H), 2.33-2.27 (m, 1H), 1.79 (qd, J=12.1, 5.7 Hz, 1H).
$^{13}$C NMR (151 MHz, MeOD) δ 152.31, 145.95, 139.00, 138.46, 131.83, 130.83, 129.66, 129.57, 129.35, 129.13, 129.08, 128.85, 123.86, 114.23, 80.44 (d, $^1$J ($\underline{C}H_2$—F)=167.6 Hz), 75.37, 71.88, 70.40, 62.50, 46.75 (d, $^2$J ($\underline{C}H_2$—$CH_2$—F)=19.9 Hz), 24.17, 23.62.
$^{19}$F NMR (565 MHz, MeOD) δ −75.23 (s, 3F), −224.37 (tt, J=47.2, 26.6 Hz, 1F).

(5R,6R)-6-((2-fluoroethyl)amino)-5,6,7,8-tetrahydronaphthalene-1,2,5-triol (LM-80)

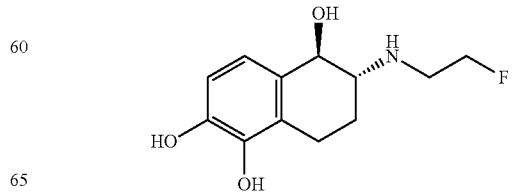

(R,R)-LM-80 was prepared from LM-78 according to general procedure 5 and the resulting TFA salt was purified by prep. HPLC (0.1% TFA in water, acetonitrile, 5% acetonitrile→20% acetonitrile in 10 min., 12.0 mL flowrate, peak eluted at 5.5 min) to give a 55% yield of grey powder.
ESI-MS m/z 241.82 [M+H]+

(1R,2R)-5,6-bis(benzyloxy)-2-((1,3-difluoropropan-2-yl)amino)-1,2,3,4-tetrahydronaphthalen-1-ol (LM-101)

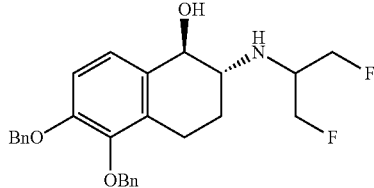 [SMILES: O[C@@H]1c2ccc(OCc3ccccc3)c(OCc3ccccc3)c2CC[C@H]1NC(CF)CF]

This product was obtained by applying procedure 1 to primary aminoalcohol LM-51 and difluoroacetone (3 eq.) under the described conditions. After purification by column chromatography (CH$_2$Cl$_2$→CH$_2$Cl$_2$/MeOH 200:1→CH$_2$Cl$_2$/MeOH 100:1), 73% of LM-101 as a yellow oil were obtained.

[α]$_{22}^{D}$ +8.8 (c=0.73 in CH$_2$Cl$_2$)
ESI-MS m/z 454.09 [M+H]+
$^1$H NMR (400 MHz, CDCl$_3$) δ 7.46 (dd, J=7.7, 1.0 Hz, 2H), 7.42-7.30 (m, 8H), 7.26 (d, J=8.5 Hz, 1H), 6.94 (d, J=8.6 Hz, 1H), 5.30 (s, 1H), 5.14 (s, 2H), 5.01 (s, 2H), 4.62-4.50 (m, 2H), 4.50-4.40 (m, 2H), 4.38 (d, J=8.5 Hz, 1H), 3.35-3.20 (m, 1H), 2.96 (ddd, J=17.8, 5.6, 3.6 Hz, 1H), 2.74 (ddd, J=11.2, 8.6, 3.0 Hz, 1H), 2.67 (ddd, J=17.4, 11.0, 6.1 Hz, 1H), 2.16-2.08 (m, 1H), 1.60-1.48 (m, 1H).
$^{13}$C NMR (151 MHz, CDCl$_3$) δ 150.90, 145.39, 137.98, 137.18, 131.54, 130.74, 128.68, 128.48, 128.41, 128.07, 128.06, 127.58, 122.85, 112.90, 82.87 (dd, $^1$J=167.6 Hz, $^3$J=5.6 Hz, NH—CH(CH$_2$F)CH$_2$F), 81.74 (dd, $^1$J=168.3 Hz, $^3$J=5.5 Hz, NH—CH(CH$_2$F)CH$_2$F), 74.36, 73.34, 71.06, 59.15, 55.12 (t, $^2$J=19.7 Hz, NH—CH(CH$_2$F)CH$_2$F), 26.67, 23.01.
$^{19}$F NMR (565 MHz, CDCl$_3$) δ −230.30 (td, J=47.2, 17.7 Hz), −230.64 (td, J=47.0, 18.3 Hz).

(5R,6R)-6-((1,3-difluoropropan-2-yl)amino)-5,6,7,8-tetrahydronaphthalene-1,2,5-triol (LM-103)

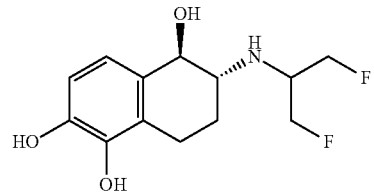 [SMILES: Oc1ccc2c(c1O)CC[C@@H](NC(CF)CF)[C@@H]2O]

LM-103 was prepared from LM-101 according to general procedure 5 and the crude TFA salt was purified by prep. HPLC (0.1% TFA in water, acetonitrile, 5% acetonitrile→15% acetonitrile in 10 min., 12.0 mL flowrate, peak eluted at 6.0 min) to give a 31% yield of product as a white powder.
ESI-MS m/z 273.92 [M+H]+

$^1$H NMR (600 MHz, MeOD) δ 6.91 (d, J=8.4 Hz, 1H), 6.74 (d, J=8.4 Hz, 1H), 4.99-4.94 (m, 1H), 4.91-4.86 (m, 2H), 4.82-4.76 (m, 1H), 4.74 (d, J=9.1 Hz, 1H), 4.31-4.19 (m, 1H), 3.45 (ddd, J=12.3, 9.2, 3.1 Hz, 1H), 3.04 (ddd, J=17.5, 5.6, 2.7 Hz, 1H), 2.72 (ddd, J=17.6, 11.8, 5.7 Hz, 1H), 2.41-2.33 (m, 1H), 1.89 (qd, J=12.3, 5.7 Hz, 1H).
$^{13}$C NMR (151 MHz, MeOD) δ 145.20, 143.13, 129.94, 123.63, 118.83, 114.65, 80.80 (dd, $^1$J=171.0 Hz, $^3$J=6.8 Hz, NH—CH(CH$_2$F)CH$_2$F), 80.60 (dd, $^1$J=171.2 Hz, $^3$J=6.9 Hz, NH—CH(CH$_2$F)CH$_2$F), 71.32, 62.02, 57.66 (t, $^2$J=19.4 Hz, NH—CH(CH$_2$F)CH$_2$F), 24.96, 23.15.

N-((1R,2R)-5,6-bis(benzyloxy)-1-hydroxy-1,2,3,4-tetrahydronaphthalen-2-yl)cyclobutanecarboxamide (LM-104)

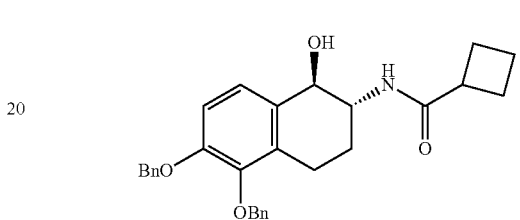

(R,R)-aminoalcohol and cyclobutyl-carboxylic acid were reacted according to procedure 2. After purification by silica gel chromatography (CH$_2$Cl$_2$→CH$_2$Cl$_2$/MeOH 100:1) a bright white solid of (R,R)-LM-104 was obtained in 65% yield.

[α]$_{23}^{D}$+69.9 (c=0.75 in CHCl$_3$)
ESI-MS m/z 480.11 [M+Na]+
$^1$H NMR (600 MHz, CDCl$_3$) δ 7.45 (d, J=7.3 Hz, 1H), 7.40-7.36 (m, 4H), 7.34-7.30 (m, 4H), 7.26 (d, J=8.5 Hz, 1H), 6.95 (d, J=8.6 Hz, 1H), 5.47 (d, J=6.6 Hz, 1H), 5.14 (s, 2H), 5.05 (d, J=11.0 Hz, 1H), 4.98 (d, J=10.9 Hz, 1H), 4.52 (d, J=7.6 Hz, 1H), 4.03-3.97 (m, 1H), 3.01 (p, J=8.4 Hz, 1H), 2.89 (dt, J=17.6, 5.0 Hz, 1H), 2.75-2.68 (m, 1H), 2.33-2.24 (m, 2H), 2.19-2.12 (m, 2H), 2.08-2.02 (m, 1H), 2.01-1.92 (m, 1H), 1.91-1.84 (m, 1H), 1.67 (dtd, J=12.8, 10.4, 5.6 Hz, 1H).
$^{13}$C NMR (151 MHz, CDCl$_3$) δ 176.75, 150.92, 145.13, 137.93, 137.16, 131.41, 130.35, 128.69, 128.48, 128.47, 128.09, 128.08, 127.57, 124.05, 113.10, 74.44, 73.78, 71.04, 53.26, 40.02, 26.21, 25.58, 25.49, 22.48, 18.24.

N-((1R,2R)-5,6-bis(benzyloxy)-1-hydroxy-1,2,3,4-tetrahydronaphthalen-2-yl)-3,3-difluorocyclobutane-1-carboxamide (LM-106)

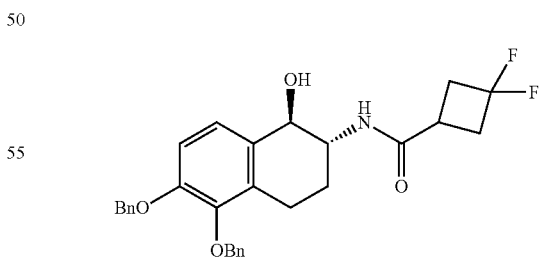

(R,R)-aminoalcohol and 3,3-difluorocyclobutyl-carboxylic acid were reacted according to procedure 2. After purification by silica gel chromatography (CH$_2$Cl$_2$→CH$_2$Cl$_2$/MeOH 100:1) an slightly orange solid was obtained in 75% yield.
[α]$_{23}^{D}$+43.4 (c=0.59 in CHCl$_3$)
ESI-MS m/z 516.09 [M+Na]+

¹H NMR (400 MHz, CDCl₃) δ 7.47-7.44 (m, 2H), 7.40-7.36 (m, 4H), 7.35-7.31 (m, 4H), 7.23 (d, J=8.7 Hz, 1H), 6.95 (d, J=8.6 Hz, 1H), 5.59 (d, J=7.0 Hz, 1H), 5.15 (s, 2H), 5.06 (d, J=10.9 Hz, 1H), 4.99 (d, J=10.9 Hz, 1H), 4.51 (d, J=7.4 Hz, 1H), 4.09-3.97 (m, 1H), 2.97-2.81 (m, 3H), 2.80-2.63 (m, 4H), 2.15-2.05 (m, 1H), 1.76-1.58 (m, 2H).

(1R,2R)-5,6-bis(benzyloxy)-2-((cyclobutylmethyl)amino)-1,2,3,4-tetrahydronaphthalen-1-ol (LM-107)

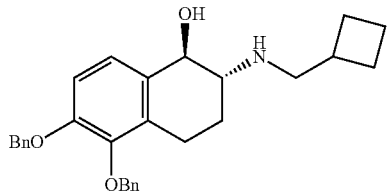 [SMILES: O[C@@H]1c2ccc(OCc3ccccc3)c(OCc3ccccc3)c2CC[C@H]1NCC1CCC1]

This intermediate was prepared by subjecting compound LM-104 to general procedure 3 and purifying the crude product by silica flash chromatography (CH₂Cl₂→CH₂Cl₂/MeOH 200:1→CH₂Cl₂/MeOH 50:1) to give 13.7 mg (61%) of white powder.

[α]₂₄^D +8.8 (c=0.69 in CHCl₃)
ESI-MS m/z 444.13 [M+H]⁺
¹H NMR (600 MHz, CDCl₃) δ 7.45 (d, J=7.2 Hz, 2H), 7.40 (d, J=6.5 Hz, 2H), 7.37 (t, J=7.4 Hz, 2H), 7.35-7.30 (m, 4H), 7.26 (d, J=8.5 Hz, 1H), 6.93 (d, J=8.5 Hz, 1H), 5.13 (s, 2H), 5.01 (s, 2H), 4.37 (d, J=8.7 Hz, 1H), 2.96 (ddd, J=17.6, 5.4, 3.2 Hz, 1H), 2.85 (dd, J=11.4, 7.4 Hz, 1H), 2.68-2.56 (m, 3H), 2.52-2.43 (m, 1H), 2.19-2.14 (m, 1H), 2.12-2.05 (m, 2H), 1.97-1.82 (m, 2H), 1.72-1.65 (m, 2H), 1.50-1.42 (m, 1H), 1.26 (br s, 1H).
¹³C NMR (151 MHz, CDCl₃) δ 150.76, 145.41, 138.07, 137.27, 132.17, 130.93, 128.66, 128.46, 128.38, 128.03, 128.00, 127.58, 122.73, 112.82, 74.31, 72.84, 71.07, 60.86, 52.97, 35.97, 26.53, 26.45, 25.79, 23.22, 18.74.

(1R,2R)-5,6-bis(benzyloxy)-2-(((3,3-difluorocyclobutyl)methyl)amino)-1,2,3,4-tetrahydronaphthalen-1-ol (LM-108)

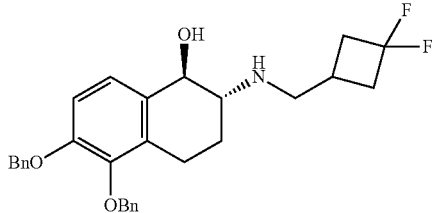 [SMILES: O[C@@H]1c2ccc(OCc3ccccc3)c(OCc3ccccc3)c2CC[C@H]1NCC1CC(F)(F)C1]

This intermediate was prepared by subjecting compound LM-106 to general procedure 3 and purifying the crude product by silica flash chromatography (CH₂Cl₂→CH₂Cl₂/MeOH 200:1→CH₂Cl₂/MeOH 100:1) to give 6.00 mg (21%) of yellow oil.

[α]₂₄^D +12.0 (c=0.60 in CHCl₃)
ESI-MS m/z 480.13 [M+H]⁺
¹H NMR (600 MHz, CDCl₃) δ 7.45 (d, J=7.2 Hz, 2H), 7.41-7.36 (m, 4H), 7.35-7.30 (m, 4H), 7.25 (d, J=8.6 Hz, 1H), 6.94 (d, J=8.6 Hz, 1H), 5.13 (s, 2H), 5.02 (s, 2H), 4.37 (d, J=8.6 Hz, 1H), 3.00-2.90 (m, 2H), 2.75-2.63 (m, 4H), 2.63-2.58 (m, 1H), 2.31-2.21 (m, 3H), 2.18-2.13 (m, 1H), 1.50-1.43 (m, 1H), 1.27 (br s, 1H).
¹³C NMR (151 MHz, CDCl₃) δ 150.84, 145.39, 138.01, 137.20, 131.79, 130.81, 128.67, 128.47, 128.39, 128.06, 128.04, 127.58, 122.76, 120.48 (dd, ¹J=283.2, 275.8 Hz, CF₂), 112.85, 74.33, 72.80, 71.05, 60.84, 51.69-51.67 (m, NH—CH₂), 39.15 (t, ²J=22.6 Hz, 2×CH₂CF₂), 25.77, 23.49 (dd, ³J=11.2, 7.2 Hz, NH—CH₂—CH), 23.08.
¹⁹F NMR (565 MHz, CDCl₃) δ −83.53 (m), −93.55 (m).

(5R,6R)-6-((cyclobutylmethyl)amino)-5,6,7,8-tetrahydronaphthalene-1,2,5-triol (LM-110)

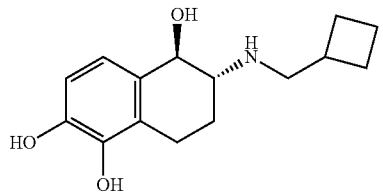 [SMILES: Oc1ccc2c(c1O)CC[C@@H](NCC1CCC1)[C@@H]2O]

LM-110 was prepared from LM-107 according to general procedure 5 and the resulting TFA salt—already showing sufficient purity—was obtained in 68% yield.
ESI-MS m/z 263.95 [M+H]⁺
¹H NMR (600 MHz, MeOD) δ 6.89 (d, J=8.4 Hz, 1H), 6.73 (d, J=8.3 Hz, 1H), 4.66 (d, J=9.0 Hz, 1H), 3.23 (d, J=7.4 Hz, 2H), 3.17 (ddd, J=12.0, 9.1, 3.0 Hz, 1H), 3.00 (ddd, J=17.6, 5.5, 3.2 Hz, 1H), 2.77-2.65 (m, 2H), 2.37-2.31 (m, 1H), 2.26-2.19 (m, 2H), 2.07-1.99 (m, 1H), 1.98-1.92 (m, 1H), 1.91-1.80 (m, 3H).
¹³C NMR (151 MHz, MeOD) δ 145.21, 143.20, 129.82, 123.56, 118.92, 114.61, 70.42, 62.16, 51.24, 33.37, 27.30, 27.04, 23.93, 22.98, 19.05.

(5R,6R)-6-(((3,3-difluorocyclobutyl)methyl)amino)-5,6,7,8-tetrahydronaphthalene-1,2,5-triol (LM-112)

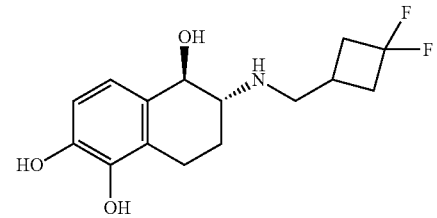 [SMILES: Oc1ccc2c(c1O)CC[C@@H](NCC1CC(F)(F)C1)[C@@H]2O]

LM-112 was prepared from LM-108 according to general procedure 5 and the resulting TFA salt purified by preparative HPLC (0.1% TFA in water, acetonitrile, 5% acetonitrile→25% acetonitrile in 10 min., 12.0 mL flowrate, peak eluted at 9.5 min) to give 39% yield of target compound.
ESI-MS m/z 299.98 [M+H]⁺
¹H NMR (600 MHz, MeOD) δ 6.90 (dd, J=8.4, 0.6 Hz, 1H), 6.74 (d, J=8.3 Hz, 1H), 4.68 (d, J=9.0 Hz, 1H), 3.41-3.33 (m, 2H), 3.22 (ddd, J=12.0, 9.0, 3.1 Hz, 1H), 3.01 (ddd, J=17.6, 5.7, 3.2 Hz, 1H), 2.87-2.78 (m, 2H), 2.73 (ddd, J=17.5, 11.3, 6.0 Hz, 1H), 2.61-2.53 (m, 1H), 2.52-2.43 (m, 2H), 2.38-2.33 (m, 1H), 1.85 (qd, J=12.0, 5.9 Hz, 1H).

¹³C NMR (151 MHz, MeOD) δ 145.25, 143.24, 129.71, 123.48, 118.86, 114.63, 70.48, 62.58, 50.52 (dd, ⁴J=3.6, 1.8 Hz, NH—CH₂), 39.98 (t, ²J=23.5 Hz, CH₂—CF₂), 39.94 (t, ²J=23.5 Hz, $\underline{C}$H₂—CF₂), 24.02, 22.96, 21.61 (dd, ³J=13.2, 6.4 Hz, NH—CH₂—$\underline{C}$H). [CF₂-carbon is not visible due to low intensity].

(1R,2R)-5,6-bis(benzyloxy)-2-(oxetan-3-ylamino)-1,2,3,4-tetrahydronaphthalen-1-ol (LM-105)

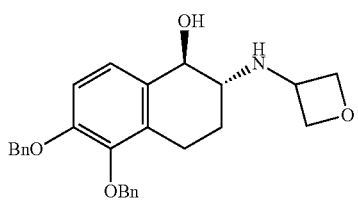 [SMILES: O[C@@H]1c2ccc(OCc3ccccc3)c(OCc3ccccc3)c2CC[C@H]1NC1COC1]

This product was obtained by applying procedure 1 to primary aminoalcohol and 3-oxetanone (2.5 eq.) under the described conditions. After purification by column chromatography (CH₂Cl₂→CH₂Cl₂/MeOH 50:1), 32% of LM-105 as a beige powder were obtained.

ESI-MS m/z 432.09 [M+H]⁺

¹H NMR (600 MHz, CDCl₃) δ 7.45 (d, J=7.3 Hz, 2H), 7.40-7.36 (m, 4H), 7.35-7.30 (m, 4H), 7.24 (d, J=8.5 Hz, 1H), 6.94 (d, J=8.5 Hz, 1H), 5.13 (s, 2H), 5.01 (s, 2H), 4.86 (t, J=6.7 Hz, 1H), 4.82 (t, J=6.7 Hz, 1H), 4.47 (d, J=6.1 Hz, 1H), 4.45 (d, J=6.1 Hz, 1H), 4.37 (d, J=8.3 Hz, 1H), 4.14 (p, J=6.6 Hz, 1H), 2.94-2.88 (m, 1H), 2.66-2.59 (m, 2H), 1.98-1.93 (m, 1H), 1.52-1.43 (m, 1H).

¹³C NMR (151 MHz, CDCl₃) δ 150.93, 145.36, 137.95, 137.14, 131.47, 130.71, 128.68, 128.48, 128.40, 128.08, 128.07, 127.57, 122.99, 112.92, 80.54, 80.32, 74.33, 72.78, 71.04, 59.60, 51.73, 26.37, 22.80.

(5R,6R)-6-(oxetan-3-ylamino)-5,6,7,8-tetrahydronaphthalene-1,2,5-triol (LM-113)

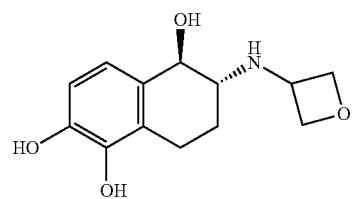 [SMILES: Oc1ccc2c(c1O)CC[C@@H](NC1COC1)[C@@H]2O]

LM-113 was prepared from LM-105 according to general procedure 5 and the crude TFA salt was purified by prep. HPLC (0.1% TFA in water, acetonitrile, 5% acetonitrile→15% acetonitrile in 10 min., 12.0 mL flowrate, peak eluted at 6.5 min) to give a 67% yield of product as a white powder.

ESI-MS m/z 251.93 [M+H]⁺

¹H NMR (600 MHz, MeOD) δ 6.89 (d, J=8.4 Hz, 1H), 6.73 (d, J=8.4 Hz, 1H), 4.94 (d, J=7.5 Hz, 1H), 4.91 (d, J=7.5 Hz, 1H), 4.81-4.78 (m, 1H), 4.77-4.74 (m, 1H), 4.74-4.70 (m, 1H), 4.64 (d, J=8.9 Hz, 1H), 3.21 (ddd, J=12.0, 8.9, 3.1 Hz, 1H), 2.99 (ddd, J=17.7, 5.7, 3.2 Hz, 1H), 2.71 (ddd, J=17.4, 11.2, 5.9 Hz, 1H), 2.23-2.17 (m, 1H), 1.83 (qd, J=11.9, 5.9 Hz, 1H).

¹³C NMR (151 MHz, MeOD) δ 145.26, 143.20, 129.55, 123.40, 118.99, 114.67, 75.28, 74.89, 70.62, 62.34, 52.05, 24.50, 22.84.

(1R,2R)-5,6-bis(benzyloxy)-2-((1,3-dimethoxypropan-2-yl)amino)-1,2,3,4-tetrahydronaphthalen-1-ol (LM-111)

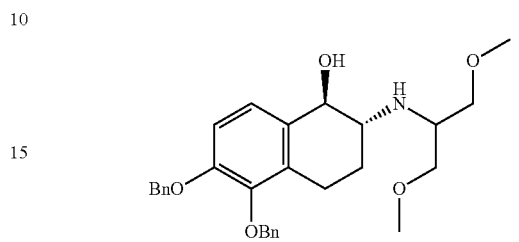

This product was obtained by applying procedure 1 to primary aminoalcohol and 1,3-dimethoxyacetone (2 eq.) under the described conditions. After purification by column chromatography (CH₂Cl₂→CH₂Cl₂/MeOH 200:1→CH₂Cl₂/MeOH 100:1), 16% of LM-111 as a yellow oil were obtained.

ESI-MS m/z 478.18 [M+H]⁺

¹H NMR (600 MHz, CDCl₃) δ 7.45 (d, J=7.4 Hz, 2H), 7.40 (d, J=6.8 Hz, 2H), 7.37 (t, J=7.4 Hz, 2H), 7.35-7.28 (m, 5H), 6.93 (d, J=8.6 Hz, 1H), 5.29 (s, 1H), 5.13 (s, 2H), 5.01 (s, 2H), 4.40 (d, J=8.9 Hz, 1H), 3.52-3.49 (m, 1H), 3.41-3.38 (m, 3H), 3.37 (s, 3H), 3.35 (s, 3H), 3.19-3.14 (m, 1H), 2.99 (ddd, J=17.6, 5.6, 2.4 Hz, 1H), 2.73-2.64 (m, 2H), 2.15-2.08 (m, 1H), 1.55 (qd, J=11.9, 5.8 Hz, 1H), 1.26 (br s, 1H).

¹³C NMR (151 MHz, CDCl₃) δ 150.64, 145.38, 138.09, 137.30, 132.11, 130.66, 128.63, 128.45, 128.37, 127.99, 127.98, 127.58, 122.63, 112.86, 74.30, 73.82, 73.47, 73.39, 71.07, 59.37, 59.25, 59.09, 55.09, 27.10, 23.69.

(5R,6R)-6-((1,3-dimethoxypropan-2-yl)amino)-5,6,7,8-tetrahydronaphthalene-1,2,5-triol (LM-114)

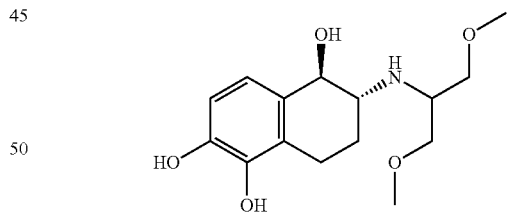

LM-114 was prepared from LM-111 according to general procedure 5 and the resulting TFA salt—already showing sufficient purity—was obtained in 51% yield.

ESI-MS m/z 298.03 [M+H]⁺

¹H NMR (600 MHz, MeOD) δ 6.90 (d, J=8.4 Hz, 1H), 6.74 (d, J=8.4 Hz, 1H), 4.71 (d, J=9.3 Hz, 1H), 3.93-3.86 (m, 1H), 3.76-3.65 (m, 4H), 3.44 (s, 3H), 3.42 (s, 3H), 3.40-3.36 (m, 1H), 3.02 (ddd, J=17.5, 5.5, 2.6 Hz, 1H), 2.70 (ddd, J=17.6, 11.8, 5.8 Hz, 1H), 2.38-2.33 (m, 1H), 1.87 (qd, J=12.3, 5.7 Hz, 1H).

¹³C NMR (151 MHz, MeOD) δ 145.17, 143.15, 129.96, 123.68, 118.81, 114.61, 71.05, 70.10, 69.68, 61.95, 59.53, 59.49, 57.90, 24.66, 23.17.

(1R,2R)-5,6-bis(benzyloxy)-2-(neopentylamino)-1,2,3,4-tetrahydronaphthalen-1-ol (LM-116)

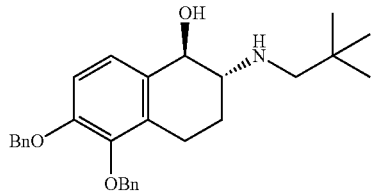 [SMILES: CC(C)(C)CN[C@@H]1CCc2c(ccc(OCc3ccccc3)c2OCc2ccccc2)[C@H]1O]

This product was obtained by applying procedure 1 to primary aminoalcohol and pivaldehyde (1 eq.) under the described conditions. After purification by column chromatography (CH$_2$Cl$_2$→CH$_2$Cl$_2$/MeOH 200:1→CH$_2$Cl$_2$/MeOH 30:1), 46% of LM-116 as a yellow oil were obtained.

ESI-MS m/z 446.19 [M+H]$^+$ $^1$H NMR (600 MHz, CDCl$_3$) δ 7.45 (d, J=7.5 Hz, 2H), 7.40 (t, J=6.7 Hz, 2H), 7.37 (d, J=7.5 Hz, 2H), 7.35-7.30 (m, 4H), 7.28 (d, J=8.5 Hz, 1H), 6.94 (d, J=8.5 Hz, 1H), 5.13 (s, 2H), 5.01 (s, 2H), 4.45 (d, J=8.7 Hz, 1H), 3.00 (ddd, J=17.7, 5.6, 2.6 Hz, 1H), 2.70 (d, J=11.5 Hz, 1H), 2.69-2.59 (m, 2H), 2.28 (d, J=11.5 Hz, 1H), 2.22-2.17 (m, 1H), 1.56-1.47 (m, 1H), 0.96 (s, 9H).

$^{13}$C NMR (151 MHz, CDCl$_3$) δ 150.70, 145.37, 138.06, 137.28, 131.97, 130.64, 128.65, 128.46, 128.39, 128.01, 128.00, 127.58, 122.58, 112.85, 74.32, 72.28, 71.06, 62.41, 58.98, 31.72, 27.78, 25.76, 23.44.

(5R,6R)-6-(neopentylamino)-5,6,7,8-tetrahydronaphthalene-1,2,5-triol (LM-117)

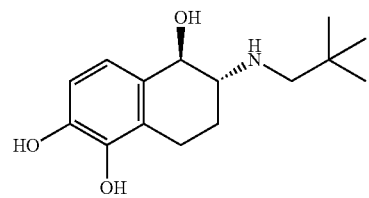 [SMILES: CC(C)(C)CN[C@@H]1CCc2c(ccc(O)c2O)[C@H]1O]

LM-117 was prepared from LM-116 according to general procedure 5 and the resulting TFA salt—already showing sufficient purity—was obtained in 85% yield.

ESI-MS m/z 266.03 [M+H]$^+$ $^1$H NMR (600 MHz, MeOD) δ 6.90 (d, J=8.4 Hz, 1H), 6.74 (d, J=8.4 Hz, 1H), 4.80 (d, J=9.7 Hz, 1H), 3.27 (ddd, J=12.6, 9.7, 3.0 Hz, 1H), 3.08-3.01 (m, 3H), 2.72 (ddd, J=17.6, 11.9, 5.9 Hz, 1H), 2.33-2.27 (m, 1H), 1.93 (qd, J=12.4, 5.8 Hz, 1H), 1.13 (s, 9H).

$^{13}$C NMR (151 MHz, MeOD) δ 145.12, 143.19, 130.13, 123.49, 118.58, 114.59, 69.42, 63.84, 56.63, 31.52, 27.33, 24.09, 23.48.

(1R,2R)-5,6-bis(benzyloxy)-2-(((trimethylsilyl)methyl)amino)-1,2,3,4-tetrahydronaphthalen-1-ol (LM-115)

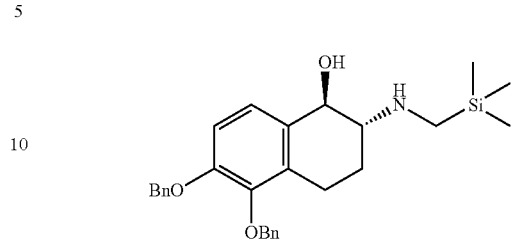

To a suspension of primary aminoalcohol (R,R)-LM-51 (1 eq.) and K$_2$CO$_3$ (3 eq.) in acetonitrile was added (trimethylsilyl)methyliodide (1 eq.). The reaction was then heated to reflux in a sealed vial for 3 days, followed by workup with water and CH$_2$Cl$_2$. The extracted CH$_2$Cl$_2$ portions were combined, washed with water and brine, dried (MgSO$_4$) and rotary evaporated. The residue was purified by silica flash chromatography (CH$_2$Cl$_2$→CH$_2$Cl$_2$/MeOH 100:1→CH$_2$Cl$_2$/MeOH 50:1) to give 34.0 mg (55%) of pure LM-115.

ESI-MS m/z 462.18 [M+H]$^+$ $^1$H NMR (400 MHz, CDCl$_3$) δ 7.47-7.43 (m, 2H), 7.42-7.30 (m, 8H), 7.27 (d, J=8.6 Hz, 1H), 6.93 (d, J=8.6 Hz, 1H), 5.13 (s, 2H), 5.01 (s, 2H), 4.50 (d, J=9.0 Hz, 1H), 3.48 (s, 1H), 3.01 (ddd, J=17.6, 5.5, 2.6 Hz, 1H), 2.68-2.56 (m, 1H), 2.40 (d, J=13.7 Hz, 1H), 2.27-2.19 (m, 1H), 2.01 (d, J=13.7 Hz, 1H), 1.54 (qd, J=12.0, 5.7 Hz, 1H), 0.11 (s, 9H).

$^{13}$C NMR (151 MHz, CDCl$_3$) δ 150.73, 145.32, 138.05, 137.27, 131.89, 130.72, 128.66, 128.47, 128.41, 128.03, 127.58, 122.69, 112.89, 74.35, 71.77, 71.07, 64.54, 50.96, 36.04, 24.49, 23.36, −2.33.

(5R,6R)-6-(((trimethylsilyl)methyl)amino)-5,6,7,8-tetrahydronaphthalene-1,2,5-triol (LM-118)

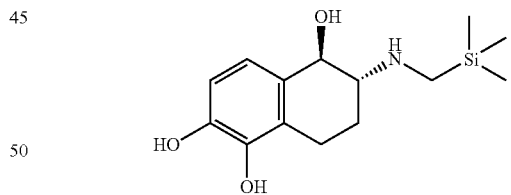

LM-118 was prepared from LM-115 according to general procedure 5 and the resulting TFA salt—already showing full analytical purity—was obtained in 79% yield.

ESI-MS m/z 282.03 [M+H]$^+$ $^1$H NMR (600 MHz, MeOD) δ 6.90 (d, J=8.3 Hz, 1H), 6.74 (d, J=8.3 Hz, 1H), 4.71 (d, J=9.2 Hz, 1H), 3.15 (ddd, J=12.2, 9.2, 3.1 Hz, 1H), 3.03 (ddd, J=17.6, 5.7, 2.8 Hz, 1H), 2.71 (ddd, J=17.6, 11.6, 6.0 Hz, 1H), 2.66 (d, J=14.9 Hz, 1H), 2.63 (d, J=14.8 Hz, 1H), 2.37-2.31 (m, 1H), 1.85 (qd, J=12.1, 5.8 Hz, 1H), 0.25 (s, 9H).

$^{13}$C NMR (151 MHz, MeOD) δ 145.19, 143.21, 129.91, 123.53, 118.81, 114.63, 69.97, 64.67, 34.77, 23.32, 23.12, −2.39.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of treating a bronchoconstrictive disease, the method comprising:
    administering to a subject in need thereof an effective amount of a β2AR selective compound to ameliorate one or more symptoms associated with undesired and/or uncontrolled bronchoconstriction in the subject, wherein administration is achieved via nebulization or inhalation of the β2AR selective compound, wherein the subject has a heart disease, wherein the β2AR selective compound has the structure:

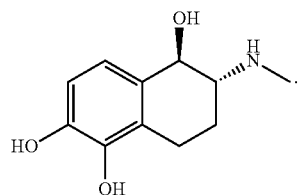

2. The method according to claim 1, wherein the bronchoconstrictive disease is selected from bronchial asthma, exercise-induced bronchoconstriction and chronic obstructive pulmonary disease (COPD).

3. The method according to claim 1, wherein the administration is achieved via nebulization of the β2AR selective compound.

4. The method according to claim 1, wherein the administration is achieved via inhalation of the β2AR selective compound.

* * * * *